United States Patent [19]
Marasco et al.

[11] Patent Number: 6,072,036
[45] Date of Patent: *Jun. 6, 2000

[54] METHOD OF INTRACELLULAR BINDING OF TARGET MOLECULES

[75] Inventors: Wayne A. Marasco, Wellesley; William A. Haseltine, Cambridge, both of Mass.

[73] Assignee: Dana-Farber Cancer Institute, Inc., Boston, Mass.

[*] Notice: This patent is subject to a terminal disclaimer.

[21] Appl. No.: 09/287,145

[22] Filed: Apr. 6, 1999

Related U.S. Application Data

[62] Division of application No. 08/438,190, May 9, 1995, Pat. No. 5,965,371, which is a continuation of application No. 08/045,274, Mar. 31, 1993, which is a continuation-in-part of application No. 07/916,939, Jul. 17, 1992.

[51] Int. Cl.[7] ........................................... C12P 21/08
[52] U.S. Cl. ..................... 530/387.3; 530/387.9; 530/388.35
[58] Field of Search .................. 530/387.1, 387.3–387.9, 530/388.1, 388.15, 388.21, 388.3, 388.35, 388.8–388.9, 389.4, 389.7, 390.1; 514/44; 424/93.2

[56] References Cited

FOREIGN PATENT DOCUMENTS

WO 92/05250  4/1992  WIPO.
WO 93/07286  4/1993  WIPO.
WO 93/12232  6/1993  WIPO.

OTHER PUBLICATIONS

Seetharam, et al., *J. Biol. Chem.*, 266(26):17376–17381 (1991).
Munro and Pelham, *Cell*, 48(5):899–907 (1987).
Chaudhary, et al., *Proc. Natl. Acad. Sci., USA*, 87(1):308–312 (1990).
Siomi, et al., *Cell*, 55(2):197–209 (1988).
Schultz, et al., *Biochem. Biophys. Res. Commun.*, 146(3):1234–1239 (1987).
Posner, *Journal of Immunology*, 146(12):4325–4332 (1991).
Brake, et al., *J. Virol.*, 64(2):962–965 (1990).
Spence, et al., *Bioconjugate Chem.*, 4(1):63–68 (1993).
Kreitman, et al., *Bioconjugate Chem.*, 4(2):112–120 (1993).
C. Nicolau, et al., *Proc. Natl. Acad. Sci.* 80:1068 (1983).
C.Y. Wang, et al., *Pro. Natl. Acad. Sci.* 84:7851 (1987).
Y. Kaneda, et al., *Science*, 243:375 (1989).
N. Benvenitsy, et al., *Proc. Natl. Acad. Sci.*, 83:9551 (1986).
P.L. Felgner, et al., *Nature*, 349:351 (1991).
R.F. Seldon, et al., *Science*, 236:714 (1987).
G.Y. Wu, et al., *J. Biol. Chem.*, 263:14621 (1988).
W.F. Anderson, et al., *Science*, 226:401 (1984).
S.A. Rosenberg, et al., *N. Eng. J. Med.*, 323:570 (1990).
D. Baltimore, et al., *Nature*, 335:395 (1988).
N. Sarver, et al., *Science*, 247:1222 (1990).
M. Poznansky, et al., *J. Virol.*, 65:532 (1991).
B.A. Sullenger, et al., *Cell*, 63:601 (1990).
J. Lisziewicz, et al., *VII International Conf. AIDS*, 2:28 (1991).
Buoounocore, et al., *Nature*, 345:625–628 (1990).

(List continued on next page.)

*Primary Examiner*—Jeffrey Stucker
*Attorney, Agent, or Firm*—Ronald I. Eisenstein; David S. Resnick; Nixon Peabody LLP

[57] ABSTRACT

The present invention relates to a method by which one can target an undesired target molecule or target antigen, preferably a protein. The method comprises the intracellular expression of an antibody capable of binding to the target. A DNA sequence is delivered to a cell, the DNA sequence contains a sufficient number of nucleotides coding for the portion of an antibody capable of binding to the target operably linked to a promoter that will permit expression of the antibody in the cell(s) of interest. The antibody is then expressed intracellularly and binds to the target, thereby disrupting the target from its normal actions.

5 Claims, 17 Drawing Sheets

OTHER PUBLICATIONS

J. Haseloff, et al., *Nature*, 334:585–591 (1988).
A.R. VanderKrol, et al., *BioTechniques*, 6:958–976 (1988).
M.H. Malim, et al., *Cell*, 58:205–214 (1989).
D. Trono, et al., *Cell*, 59:113–120 (1989).
L. Riechmann, et al., *J. Mol. Biol.*, 203:825–828 (1988).
J.R. Carlson, et al., *Molecular and Cellular Biology*, 8:2638–2648 (1988).
S. Biocca, et al., *The EMBO Journal*, 9:101–108 (1990).
P. Piccioli, et al., *Proc. Natl. Acad. Sci.*, 88:5611–5615 (1991).
Faraji–Shaden, *Medical Hypothesis*, 32:81–84 (1990).
Norley, et al., *Immunobiol.*, 184:193–207 (1992).
T. Werge, et al., *FBS*, 274:193–198 (1990).
Biocca et al., *Cytotechnology*, 5:S49–50 (1991).
Hiatt, *Nature*, 344:469–470 (1990).
Benvenuto et al., *Plant Molecular Biology*, 17:865–74 (1991).
Hiatta et al., *Nature*, 342:76–77 (1989).
Spense et al., *Bioconjugate Chem.*, 4:63–68 (1993).
Palker, *Antiviral Chem. Chemother.*, 3:1271–139 (1992).
Orlandi et al., *Proc. Natl. Acad. of Science, USA*, 86(10):3833–3837 (1989).
Piccioli et al., *Proc. Natl. Acad. of Science, USA*, 88(13):5611–5615 (1991).
Biocca et al., *EMBO*, 9(1):101–108 (1990).
Werge et al., *FEBS*, 274(1–2):193–198 (1990).
Biocca et al., Third European Congress on Cell Biology, Firenze, Italy, Sep. 2–7, 1990, *Cell Biology International Reports*, vol. 14, p. 217, Abstract No. P555 (1990).
Clapham et al., *Proc. Natl. Acad. of Sciences of the USA*, 81(9):2886–2889 (1984).
Ruscetti et al., *International Conference of AIDS*, vol. 5, Abstract No. T.C.P. 33, p. 572 (1989).
Ashley et al., *Medical Virology*, p. 387 (1982).
Huston et al., *Proc. Natl. Acad. of Science of the USA*, 85(16):5879–83 (1988).
Feng et al., *Nature*, 334:165–167 (1988).
Hiatt et al., *Nature*, 342:76–78 (1989).
Mazanec et al., Meeting of the Federation of American Societies for Experimental Biology (FASEB), Part 1, Anaheim, California, USA, Apr. 5–9, 1992. *FASEB Federation of American Societies for Experimental Biology*, vol. 6, No. 4, Abstract No. A1228 (1992).

METHOD OF INTRACELLULAR BINDING OF TARGET MOLECULES

This application is a divisional of application Ser. No. 08/438,190, filed May 9, 1995 U.S. Pat. No. 5,965,371 which is a continuation of Ser. No. 08/045,274, filed Mar. 31, 1993, which is a CIP of Ser. No. 07/916,939, filed Jul. 17, 1992.

The present invention is directed to a method for intracellular binding of specific molecules, preferably proteins. More specfically, this method involves the intracellular expression and subsequent use of antibodies specific for a desired molecule.

Various abnormalities appear to be the result of the undesired expression of a particular molecule such as a protein. For example, many tumors are believed to be the result of the overexpression of cellular oncogenes, such as neu, myc, abl, etc. Other malignancies are believed to be the result of expression of an altered receptor. Certain illnesses are caused by the undesired cellular expression of viral proteins. For example, the human immunodeficiency virus (HIV) uses mammalian cells for the preparation of viral encoded proteins including structrual proteins and regulatory enzymes. Human T-cell Leukemia virus type 1 or 2, (HTLV-1 or 2) produce tumors in infected individuals as a result of viral expression. Such viral encoded proteins can result in the assembly of virions which can in turn infect other cells.

Therapeutic strategies have included the development of drugs to target the undesired proteins, means of intercellular blocking of such proteins, for example, soluble CD4, and the use of drugs which will selectively kill cells expressing the undesired proteins.

Another method of treatment that has been suggested is the transfer of genetic materials into cell. For example, by receptor mediated gene delivery, transkaryotic implantation and viral shuttle vectors such as retroviral gene transfer. In such methods, broadly referred to as gene therapy, cells which are either deficient in a protein or produce a dysfunctional protein are hoped to be mended by introducing into the cell DNA coding for the normal gene product.

In vivo gene expression has been reported following direct injection of non-infectious, non-oncogenic plasma DNA encapsulated in lyposomes [Nicolau, C., et al., *Proc. Natl. Acad. Sci.* 80:1068 (1983)] immunoliposomes [Wang, C. Y., et al., *Proc. Natl. Acad. Sci* 84:7851 (1987)] and in a liposome/red blood cell membrane hybrid [Kaneda, Y., et al. *Science* 243:375 (1989)]. Expression from a variety of calcium phosphate-precipitated gene sequences has been reported following direct intraperitoneal injection [Benvenitsy, N., et al. *Proc. Natl. Acad. Sci* 83:9551 (1986); Felgner, P. L., et al., *Nature* 349:351 (1991)] or following transkaryotic implementation [Seldon, R. F., et al. *Science* 242:714 (1987)]. In vivo gene targeting has also been accomplished by receptor mediated gene delivery in which a complex between an asialoorosomucoid/polysine conjugate and plasmid receptor genes have been used to target expression exclusively to the liver, following intravenous administration [Wu, G. Y., et al., *J. Biol. Chem.* 263:14621 (1988)]. Retroviral gene transfer is reported to offer high efficiency of infection, stable integration and expression in most cells [Anderson, W. F., *Science* 226:401 (1984)]. In vivo gene therapy has been initiated in patients with ADA deficiency who have had reinfused into their blood, autologous lymphocytes carrying the ADA gene and in cancer patients with advanced melanoma who have had reinfused tumor infiltrating lymphocytes (TIL) which carry the gene for tumor necrosis factor (TNF) [Rosenberg, S. A., et al., *N. Eng. J. Med.* 323:570 (1990) all of these articles are specifically incorporated herein by reference].

Gene modification of cells which continually express a viral inhibitor and result in the inhibition of viral infection have been proposed and referred to as intracellular immunization. [Baltimore, D., *Nature* 335:395–196 (1988)]. Towards this goal, several approaches have been tested including HIV-1 specific ribozymes [Sarver, N., et al. *Science* 227:1222 (1990)], antisense RNA [Posnansky, M., et al., *J. Virol.* 65:532 (1991)], tar decoys [Sullenger, B. A., et al., *Cell* 63:601 (1990); Lisziewicz, J., et al., *VII Internat'l. Conf. AIDS* 2:28 (1991)], dominant negative mutants and others. [Buonocorel, et al., *Nature* 345:625–628 (1990); Hasseloff, J., et al. *Nature* 334:585–591 (1988); VanderKrol, A. R., et al., *BioTechniques* 6:958–976 (1988); Malim, M. H., et al., *Cell* 58:205–214 (1989); and Trono, D., et al., *Cell* 59:113–120 (1989)]. A major impediment to the development of effective gene inhibition protocols using such antisense RNA or ribozymes is the ability to achieve a high level of expression of the inhibitor encoding DNA template in the transformed cells and this may also be a potential problem for using dominant negative mutants because of the competitive nature of the inhibition.

It would be desirable to have a method which can be used to achieve a high level of expression of an inhibitor to the desired molecule.

It would be desirable to have a method which can specifically target these undesired molecules and which has wide applicability.

It would be desirable to have a method which does not introduce cytotoxic chemicals into a cell.

It would be desirable to have a method which provides a ready means of targeting undesired proteins.

SUMMARY OF THE INVENTION

We have now discovered a method by which one can target an undesired molecule (sometimes referred to as a target molecule or target antigen), preferably a protein. This method comprises the intracellular expression of an antibody capable of binding to the target. A DNA sequence containing a sufficient number of nucleotides coding for the portion of an antibody capable of binding to the target operably linked to a promoter that will permit expression of the antibody in the cell(s) of interest (antibody cassette) is delivered to a cell. Thereafter, the antibody is expressed intracellulary and binds to the target, thereby disrupting the target from its normal actions. In one preferred embodiment, the "antibody gene" of the antibody cassette would utilize a cDNA encoding heavy chain variable ($V_H$) and light chain variable ($V_L$) domains of an antibody which can be connected at the DNA level by an appropriate oligonucleotide as a bridge of the two variable domains, which on translation, form a single polypeptide (referred to as a single chain variable fragment (sFv)) capable of binding to a target such as a protein. The antibody gene does not encode an operable secretory sequence and thus the expressed antibody remains within the cell. In certain preferred embodiments, a nucleotide sequence encoding an intracellular localization leader is also used.

Preferred cell targets are retrovirally infected cells such as HIV infected cells, where the targets are the virally encoded protein. For example, one can use antibodies against structural proteins such as the envelope glycoprotein and gag protein, and/or against tat, rev, nef, vpu and/or vpx regulatory proteins. In one preferred embodiment, one would use an antibody cocktail (i.e. mixture of antibodies) to target a variety of the viral target proteins. Another preferred target includes oncogenes such as trans-membrane growth factor receptors, receptors, growth factors, membrane associated guanine nucleotide binding proteins, etc.

DETAILED DESCRIPTION OF THE INVENTION

Figure 1A:
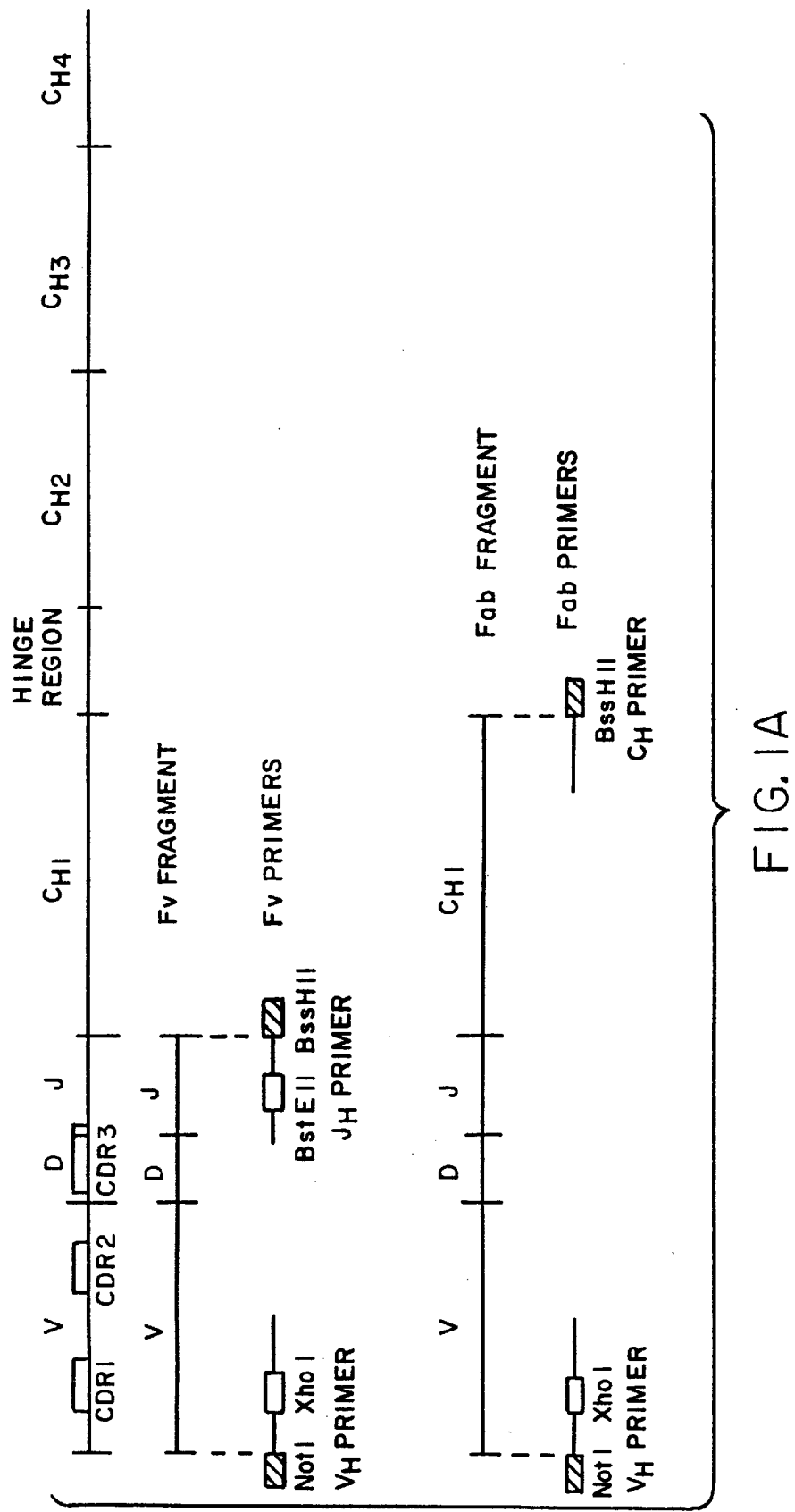
FIGS. 1A & 1B show the location of PCR primers for cloning of variable and constant regions of immunoglobulin heavy and light chain genes.

The present invention is directed to a method of targeting a particular molecule (target molecule), preferably a protein such as an undesired protein. This method comprises the intracellular expression of an antibody which is capable of binding to a specific target (e.g. a target protein), wherein the antibody preferably does not contain sequences coding for its secretion. Such antibodies will bind the target intracellularly. As used herein, the term antibody refers to at least that portion of an immunoglobulin capable of selectively binding to a target such as a protein. The antibody is expressed from a DNA sequence which contains a sufficient number of nucleotides coding for the portion of an antibody capable of binding to the target, referred to herein as the antibody gene. The gene is operably linked to a promoter that will permit expression of the antibody in the cell(s) of interest. Promoters are well known in the art and can readily be selected depending on what cell type you wish to target. Furthermore, the use of inducable promoters, which are also well known in the art, in some embodiments are preferred. Such as when the function of a target protein is a result of its overexpression. Then by "turning the promoter on" one can selectively obtain the expression of the antibody. The entire sequence of antibody gene and promoter is described herein as an antibody cassette. The cassette is delivered to the cell by any of a number of means described below, which permit intracellular delivery of a gene.

The cassette results in the intracellular expression of the antibody. The expressed antibody can then bind to the target antigen. This permits a wide variety of useful applications.

Almost any kind of biologic molecule can serve as an antigen, for example, intermediate metabolites, sugars, lipids, autacoids, and hormones as well as macromolecules such as complex carbohydrates, phospholipids, nucleic acids such as RNA and DNA, and proteins. The skilled artisan can generate antibodies that will specifically bind to both the small molecules and macromolecules. For example, with small molecules one commonly attaches the small molecule (sometimes referred to as a hapten) to a macromolecule (sometimes referred to as a carrier) before immunization. The hapten-carrier complex acts as an immunogen. Thus antibodies that will specifically bind to a wide range of targets are known. The preferred target molecules include proteins, RNA, DNA and haptens. More preferably, the targets are proteins, RNA and DNA. Still more preferably, the target is a protein.

Overexpression of a number of oncogenes has been reported to be associated with malignant cellular transformation. For example, amplification of myc has been reported in COLO 320 colon carcinoma cell cultures, the SKBR3 breast carcinoma cell line and in lung carcinoma cell lines. Amplification of N-myc has been reported in neuroblastoma cell lines and retinoblastoma. Amplification of c-abl, c-myb, and other oncogenes have also been reported to be associated with malignant transformation. See, ch 12 "Human Oncogenes" pp 487–543, RNA Tumor Viruses, Molecular Biology of Tumor Viruses, 2nd Ed., Weiss, R. et al., Ed. (Cold Spring Harbor Laboratory (1985)).

High levels of various oncogenes has also been reported to effect the risk of recurrence of the tumor. For example, a correlation between the level of neu/c-erbB-2 and the cause and course of human breast cancer has been reported. See, Paterson, M. C., et al., *Cancer Research* 51:556–567 (1991); high levels of myc, int-2 and hst-1 have also been associated with breast cancer. Similarly, elevated levels of the receptor for EGF, EGF-R have been shown to be associated with breast cancer. Grimaux, M., et al., *Int. J. Cancer* 45:255–262 (1990). The overexpression of these and other oncogenes have also been reported as being associated with other cancers.

Many oncogenes show some homology to genes involved in cell growth. For example, see the table below.

TABLE[1]

| CATEGORY | ONCOGENE | HOMOLOGOUS CELLULAR GENE |
|---|---|---|
| Growth Factors | sis | PDGF-/2 |
|  | int-2 | FGF-like |
| Transmembrane growth factor receptors | erbB | EGF receptor |
|  | neu (erbB-2, HER-2) |  |
|  | fms | M-CSF receptor |
|  | ros, kit, and others |  |
| Membrane-associated tyrosine kinases | abl |  |
| Membrane associated guanine nucleotide binding proteins | src family[2] |  |
|  | fes.fps[3] |  |
|  | K—, N—and H-ras |  |
| Cytoplasmic serine-threonine kinases | raf/mil |  |
|  | mos |  |
| Cytoplasmic hormone receptors | erbA | Thyroid hormone receptor |
| Nuclear factors | c-myc |  |
|  | N-myc |  |
|  | L-myc, |  |
|  | fos |  |
|  | jun |  |
|  | myb, ets, ski, and others |  |
| Antioncogenes | RB |  |
| Others | bcl-2 |  |
|  | bcl-1 |  |
|  | int-1 |  |

[1]Adapted from Druker, B.J., et al., N. Eng. J. of Mol. 321:1383–1392 (1989). PDGF denotes platelet-derived growth factor, FGF fibroblast growth factor, EGF epidermal growth factor, and M-CSF mononuclear-phagocyte growth factor.
[2]The family includes src, fgr, yes, lck, hck, fyn, lyn, and tkl.
[3]The subcellular location of these oncogene products is uncertain.

Antibodies to most of these oncogenes have been reported. In addition, to overexpression of oncogenes (sometimes referred to as oncs), some oncogenes undergo a mutation from a proto-onc (normal gene for normal protein) to an onc (gene whose protein can cause malignant transformation) which appears to result in malignant transformation of cells. For example, point mutations of the ras gene at the codons for the ras p21 at residue positions 12, 13 and 61 have resulted in mutant ras p21 proteins which are associated with various cancers. Antibodies specific to many of these ras mutants are known.

Similarly, expression of viral proteins can lead to diseases resulting in illness and even death. The virus can be either RNA or DNA viruses. For example, one type of RNA viruses, retroviruses are typically classified as being part of one of three subfamilies, namely oncoviruses, spumaviruses and lentiviruses. Infection by oncoviruses is typically associated with malignant disorders. The viral proteins encoded include the gag, pol, and envelope. In some instance the virus contains oncogenes which encode a protein capable of malignant transformation of a cell in culture. Lentiviruses result in infection which is generally slow and cause chronic debilitating diseases after a long latency period. In addition to genes encoding the gag, pol and envelope structural proteins, they also encode a variety of regulatory proteins. The virus's RNA and/or DNA can take over the cell machinery to produce the virally encoded protein.

For example, HTLV-1 is a retrovirus which is the etiological agent of adult T-cell leukemia-lymphoma (ATLL), an aggressive neoplasm of CD4+ T-cells [Poiesz, B. J., et al. Proc. Natl. Acad. Sci. 77:7415–7419 (1980)]. The viral proteins expressed by such virus result in the transformation of the cell. The tax and rex gene and gene products appear to be significant with respect to tumorgenicity. Thus, they are a preferred grouping of target molecules.

HIV constitutes a family of lentiviruses including HIV-1 and HIV-2, that are the etiological agents of immunodeficiency diseases such as the acquired immune deficiency syndrome (AIDS) and related disorders [Barre-Sinoussi, et al., Science 220:868–871 (1983); Gallo, et al., Science 224:500–503 ( ) 1984) ; Levy, et al., Science 225:840–842 (1984); Popovic, et al., Science 224:497–500 (1984)].

The Epstein-Barr Virus has been linked to a number of tumors such as selected outbreaks of Burkitt's lymphoma, nasopharygeal cancer and B-lymphomas in immunosuppressed individuals. [zur Hausen, H., Science 254:1167–1173 (1991)].

Hepatitis B virus has been linked to hepatocellular cancer [zur Hausen, supra]. In particular, the X open reading frame of the virus seems to be involved [Ibid]. Accordingly, an antibody that targets this region or expression products from this region would be preferable in the present method.

Papillomaviruses have been linked to anogenital cancer [Ibid]. in these viruses the E6 and E7 genes appear to be involved and would be good targets.

By intracellular binding to nucleic acid such as a DNA provirus one can prevent or inhibit the virus's integration into the cell. By binding to the RNA of the virus one can interfere with its expression of viral protein. Anti-nucleotide antibodies have been extensively studied [Van Es, J. H., et al., J. of Immun. 149:2234–2240 (1992); Brigido, M. M. et al. J. of Immun. 150:469–479 (1993); Stollar, B. D., et al., Proc. Natl. Acad. Sci. USA 83:4469–4473 (1986) ; Eilat, D., et al., J. of Immun. 141:1745–1753 (1988); Brigido, M. M., et al., J. of Immun. 146:2005–2009 (1991)] and the antibodies share the same basic features.

These antibodies can be produced and/or screened by standard techniques such as using a nucleotide sequence such as RNA to screen a library containing antibodies [Tsai, D. E., et al. J. of Immun. 150:1137–1145 (1993); Okano, Y., et al., J. of Immun. 149:1093–1098 (1992); Tsai, D. E., Proc. Natl. Acad. Sci. USA 89:8864–8868 (1992).

One can also preferably select and/or designs antibodies to target and interfere with an important nucleic acid binding site. For example, the TAR element of the primate immunodeficiency viruses. This nucleic acid sequence is present in the 5' LTR and is responsive to TAT resulting in enhanced expression of viral protein.

By intracellular binding to target proteins of these oncogenes and viruses it is possible to disrupt the normal functioning of such proteins reducing or avoiding the disruptive effect of the protein.

For example, binding to a protein that has to be further processed such as a receptor protein, a viral envelope protein, e.g. HIV gp160, can significantly reduce the cleavage of the protein into its active components. As another example, the capsid protein, e.g. the HIV capsid protein, is modified co-translationally by addition of the fatty acid, myristic acid. It appears that myristic acid is involved in the attachment of the capsid precursor protein to the inner surface of cells. In HIV proviruses, which have been altered so that they are not capable of adding this myristic acid, the provirus is not infectious. Studies of the process of myristylation reveal a requirement for glycine at position two from the amino terminus and also at amino acid residues within six to ten amino acids from the site of myristylation. Thus, antibody binding to the protein at and near these sites can disrupt myristylation.

Similarly, binding to a protein that has a significant external domain can hinder the effect of the protein.

In another embodiment, by binding to a dysfunctional receptor protein, one can block the undesired interactions that can result in cellular dysfunction such as malignant transformation.

For example, many proteins, such as surface receptors, transmembrane proteins, etc. are processed through the endoplasmic reticulum (sometimes referred to as ER)-Golgi apparatus. Examples of such proteins include neu, envelope glycoproteins such as those of the primate lentiviruses, e.g., HIV-1 or HIV-2. By using antibodies that can be delivered to such a region of the cell and be specific for a particular protein, one can disrupt the function of such protein without disrupting other cellular functions. For example, the PDGF-/2 and FGF-like factors produced by sis and int-2 pass through the ER. These factors are involved in many cancers. Thus, in addition to targeting the receptor, one can target the growth factors by using antibodies to them.

Growth factors are also expressed by many other malignant cells such as from carcinoid syndrome tumors and these would be another target.

One can also use this method to dirrupt a function that is undesirable at a particular time. For example, the MHC class I and class II molecules are important in the immune systems recognition of antigens. [Teyton, L., et al., *The New Biologist* 4:441–447 (1992); Cox, J. H., et al., *Science* 247:715–718 (1990); Peters, P. J., et al., *Nature* 349:669–676 (1991); Hackett, *Nature* 349:655–656 (1991)]. However, such immune recognition, particularly from MHC class II molecules can cause problems such as in organ transplants. [Schreiner, G. F., et al., *Science* 240:1032–1033 (1988)]. Thus, by targeting class II molecules with organ transplants you can down reguatee the host immune response. These molecules can preferably be targeted at different points in their processing pathway. Preferably, one would use an inducable promoter for the antibody gene.

Thus, by taking into account the particular target many variations of this method can be designed by the skilled artisan.

For instance, the HIV-1 envelope gene directs the synthesis of a precursor polyglycoprotein termed gp160. This protein is modified by addition of multiple N-linked sugars as it enters the endoplasmic reticulum [Allan, J. S., et al., *Science* 228:1091–1094 (1985); Robey, W. G., *Science* 228:593–595 (1985); DiMarzo-Veronese, F., et al., *Science* 229:1402–1405 (1985); Willey, R. L., *Cell Biol.* 85:9580–9584 (1988)]. The glycosylated envelope protein precursor is then cleaved within the Golgi apparatus to yield a mature envelope protein comprised of an exterior glycoprotein, gp120, and a transmembrane protein, gp41 [Willey, *Cell Biol*, supra; Stein, B. S., et al., *J. Biol. Chem.* 265:2640–2649 (1990); Earl, P. L., et al., *J. Virol.* 65:2047–2055 (1991)]. The envelope glycoprotein complex is anchored to the virion envelope and infects cell membranes by gp41 through non-covalent interactions [DiMarzo-Veronese, *Science supra*; Gelderblom, H. R., et al., *Lancet ii:*1016–1017 (1985)]. Following binding of the gp120 exterior glycoprotein to the CD4 receptor, the fusion of viral and host cell membranes allows virus entry [Stein, B. S., *Cell* 49:659–668 (1987)]. The fusogenic domain of the gp120/gp41 complex is thought to reside at the amino terminus of gp41 because this region exhibits sequence homology with a fusogenic domain of other viral proteins [Gallaher, W. R., *Cell* 50:327–328 (1987)]; Gonzalez-Scarano, F., *AIDS Res. Hum. Retrovir.* 3:245–252 (1987)] and because mutations in this region inactivate the virus and prevent viral fusion [Kowalski, M., et al., *Science* 237:1351–1355 (1987); Kowalski, M., et al., *J. Virol* 65:281–291 (1991); McCune, J. M., et al., *Cell* 53:55–67 (1988)].

While the processed gp120 and gp41 are transported to the cell surface and secreted as part of the virus' virion, sometimes referred to as viral particles, the uncleaved gp160 is delivered to lysosomes for degradation. The cleavage process normally is relatively inefficient. Thus, the method of using intracellular antibodies to bind to the newly synthesized gp160 in the lumen of the endoplasmic reticulum and inhibit its transport to the Golgi apparatus, greatly reduces the amount of protein available for cleavage to gp120 and gp41. Accordingly, the viral particles produced have greatly diminished amounts of gp120 and gp41 on their surface. Such particles are not considered as infectious. This discussion of the HIV-1 gp160/120/41 proteins is exemplary of other envelope proteins and processed proteins. The same techniques used herein can be adapted by known techniques based upon the present disclosure.

Additionally, the envelope protein of the immunodeficiency viruses has been implicated in the other aspects of the disease [DeRossi, A., et al., *Proc. Natl. Acad. Sci.* 83:4297–4301 (1986)].

For example, HIV infection of cell cultures typically generates an acute and/or chronic infection. In both cases, virus is produced and becomes released by budding at the cellular membrane. An acute infection is typically characterized by a cytopathic effect manifested by vacuolization of cells and formation of syncytia and consequently cell lysis [Laurent-Crawford, *Virol* 185:829–839 (1991)]. In tissue cultures, the cytopathic effects of HIV-1 consist of multinucleated giant cell (syncytium) formation and the lysis of single cells. [Popovic, M., *Science* 224:497–500 (1984); Somasundarin, M., et al., *J. Virol* 61:3114–3119 (1987)]. Syncytium formation is mediated solely by the HIV-1 envelope protein expressed on the infected cell surface [Sodroski, J., et al. *Nature* 322:470–474 (1986); Lifson, J. D., et al., *Nature* 323:725–728 (1986)]. The envelope binds to the CD4 receptor present on adjacent cells and then, via a fusion reaction agnalogous to that involved in virus entry, the apposed cell membranes are fused so that heterokaryons are formed.

Single cell lysis also depends on efficient membrane fusion induced by the envelope glycoproteins as some mutations in the gp41 amino terminus result in replication competent viruses that are attenuated for both syncytium formation and single cell lysis [Kowalski, M. L., et al., *J. Virol.* 65, *supra* (1991)]. It has also been reported that amino acid changes in gp120 which effect processing of the gp160 precursor can decrease single cell lysis [Stevenson, M., et al. *J. Virol* 64:3792–3803 (1990)] and that single cell lysis requires adequate levels of CD4 expression independent of the level of viral protein expression or viral DNA in the infected cell [De Rossi, A., et al., *Proc. Natl. Acad. Sco, USA, supra*].

In addition, the HIV envelope glycoprotein has been implicated by a number of other individuals in explaining the onset of the associated immunodeficiency infected individuals. Siliciano, R. F., et al., [*Cell* 54:561–575 (1988)] have shown that a subset of $CD4^+$ gp120-specific clone manifest cytolytic activity and lyse uninfected autologous $CD4^+$ T-cells in the presence of gp120 in a process that is strictly dependent upon CD4 mediated uptake of gp120 by T- cells. Since gp120 can be shed from infected cells, this CD4 dependent autocytolytic mechanism can contribute to the profound depletion of CD4+ T-cells in AIDS patients. Kion, T. A., et al., [*Science* 253:1138–1140 (1991)] and Hoffman, G. W., et al., [*Proc. Natl. Acad. Sci. USA* 88:3060–3064 (1991)] have shown that an autoimmune idiotypic network develops in HIV-1 infections which leads to the development of autoimmune antibodies that destroy $CD4^+$ T-cells. This autoimmune mechanism develops because of the sequence homologies between gp120 and class II MHC molecules [Young, J. A. T, *Nature* 333:215 (1988)]. The immunosuppresive effects of gp120 on the $CD4^+$ T-cell proliferation to antigenic stimulus have been demonstrated [Hoxie, J. A., et al., *Science* 234:1123–1127 (1986); Diamond, D. C., et al., *J. Immunol.* 141:3715–3717 (1988); Gurley, R. J., et al., *Proc. Natl. Acad. Sci. USA* 86:1993–1997 (1989); Crise, B., et al., *J. Virol.* 66:2296–2301 (1992)]. These studies suggest that immunodeficiency diseases such as HIV-1 may affect major histocompatibility complex II restricted antigen recognition independent of $CD4^+$ T-cell loss. In rodent neurons, gp120 has been shown to cause an increase in intracellular calcium and neuronal toxicity [Dreyer, E. B., et al., *Science* 248:364–367 (1990)], an effect which might be mediated by activation of the nuclear endonuclease. In addition, activation induced T-cell death, or apoptosis, has also been proposed as occurring in vivo and accounting for the progressive depletion of $CD4^+$ T-cells that leads to AIDS [Groux, H., et al., *J. Exp. Med.* 175:331–340 (1992); Meyaard, L., et al., *Science* 257:217–219 (1992)]. In vitro and in vivo soluble gp120 can interact with CD4 receptors on uninfected cells leading to an abortive cell activation and thus trigger apoptosis [Mcconkey, D. J., et al., *Immunol. Today* 11:120–121 (1990); Pinching, A. J., et al., *Immunol. Today* 11:256–259 (1990); Newell, M. K., et al., *Nature* 347:286–289 (1988)]. It has also been proposed that the envelope glycoprotein can act as a superantigen binding only the variable-β region of the T-cell antigen receptor, thereby inducing massive stimulation and expansion of such T-cells, followed by deletion or anergy. Pantaleo, G., et al., *N. Eng. J. of Med.* 238:327–335 (1993). Thus, by decreasing the amount of gp120, effects associated with AIDS can be alleviated and retarded.

As will be discussed in greater detail herein, we have established that intracellular expression of an antibody to its target, for example, the antibody to the envelope glycoprotein, results in an antibody that binds the target, e.g. envelope glycoprotein, in the cell and prevents further processing. The present method is highly specific and does not adversely affect cellular functioning. Thus, a mutant envelope protein that contains a single point mutation that abolishes the protein's ability to bind to this antibody will be processed normally in cells that constitutively express the protein. Similarly, single chain antibodies to other proteins will not affect the processing of the envelope protein. Thus, the present methodology permits using an antibody specific to a particular protein and results in a process that can be tailored for specific diseases. Additionally, the methodology can be used prophylatically. One could even have the antibody under the control of a promoter that will be specifically activated by the target (e.g. an HIV LTR) thereby only turning the antibody on when the target is present. Other types of inducible promoters are known in the art and can be selected and used based upon the present disclosure.

The use of the present antibodies do not affect the processing of other proteins. For example, the antibody to the HIV envelope glycoprotein does not bind other envelope glycoproteins and does not prevent processing of such a protein. For example, the processing of an unrelated envelope glycoproteins, such as Bunyavirus envelope glycoprotein, will not be affected. We have shown that cells that are subjected to the present method, for example by intracellular delivery of an antibody to the envelope protein to produce a cell that constitutively expresses that antibody, results in a 1,000 to 10,000 fold reduction in the activity of viral particles produced when compared to virus from parental cells.

Numerous other sites can be targeted. For example, targeting the cytoplasmic side of a membrane receptor. It is through the cytoplasmic tail that signal transduction occurs. [Luttrell, L. M. et al., *Science* 259:1453–1457 (1993); Epstein, R. J.,, et al., *Proc. Natl. Acad. Sci USA* 89:10435–10439 (1992)]. For example, using the neu/erbB-2 receptor or G protein receptor one can target the loop or cytoplasmic tail thereby preventing such signal transduction. For example, one preferably uses antibodies to activated receptors such as to phosphorylated amino acids. Thus, the pool of target receptors can be reduced.

The antibodies will bind specifically to the target, e.g. a protein, and can thus effectively compete with other molecules that will also form complexes with the protein. To insure that the antibodies of the present invention can compete successfully with other molecules, they must retain at least about 75% of the binding effectiveness of the complete antibody to that target, i.e. having constant as well as variable regions. More preferably, it has at least 85% of the binding effectiveness of the complete antibody. Still more preferably, it has at least 90% of the binding effectiveness of the complete antibody. Even more preferably, it has at least 95% of the binding effectiveness.

We have developed a method that is broadly applicable to a wide range of target molecules including proteins, RNA, DNA, haptens, phospholipids, carbohydrates, etc. as will be discussed below.

The target molecules can be present in a wide range of hosts. For example, animals, birds, and plants. Preferably, the target is animals including humans. More preferably, the species is one that has industrial importance such as fowl, pigs, cattle, cows, sheep, etc. Most preferably, the species is a human.

Although antibodies have the ability to recognize an almost limitless number of foreign molecules, in nature, antibodies recognize stuctures exterior to the cell. [Winter, G., et al., *Nature* 349:293 (1991)]. Once synthesized, antibodies are secreted into the surrounding fluid or remain bound to the outer cell membrane [Klein, *Immunology*, Blackwell Scientific Publications, Cambridge, Mass. 1990]). We have found a means to express antibodies which retaining the ability to specifically bind to a target intracellularly.

Thus, specificity for a particular target can be obtained by using the immune system, itself. One uses the target or an antigenic portion thereof or a hapten-carrier complex to generate an antibody. This can be accomplished by standard techniques.

For example, the antigen binding or variable regions is formed by the interaction of the variable heavy ($V_H$) and variable light ($V_L$) domains at the amino termini of the chains. The smallest fragment containing a complete binding site is referred to as Fv and is a heterodymer of the $V_H$ and $V_L$ domains. However, it is possible to obtain binding without a complete binding site. For example, one can obtain antigen binding activity using only a heavy chain binding domain (dAbs, also referred to as single domain antibodies). As aforesaid, in the present invention, one can use a gene coding for such an antibody fragment as long as it retains sufficient binding ability compared to the parent antibody. Preferably, one uses at least at least a $V_H$ and $V_L$ heterodimer (Fv).

Determination of the three-dimensional structures of antibody fragments by X-ray crystalography has lead to the realization that variable domains are each folded into a characteristic structure composed of nine strands of closely packed β-sheets. The structure is maintained despite sequence variation in the $V_H$ and $V_L$ domains [Depreval, C., et al., *J. Mol. Biol.* 102:657 (1976); Padlan, E. A., *Q. Rev. Biophys.* 10:35 (1977)]. Analysis of antibody primary sequence data has established the existence of two classes of variable region sequence. Hypervariable sequences and framework sequences [Kabat, E. A., et al., Sequences of Protein of Immunological Interests, 4th ed. U.S. Dept. Health and Human Services (1987)]. The framework sequences are responsible for the correct β-sheet folding of the $V_H$ and $V_L$ domains and for the interchain interactions that bring the domains together. Each variable domain contains three hypervariable sequences which appear as loops. The six hypervariable sequences of the variable region, three from the $V_H$ and three from the $V_L$ form the antigen binding site, are referred to as a complementarity determining region (CDRs).

By cloning the variable region genes for both the $V_H$ and $V_L$ chains of interest, it is possible to express these proteins in bacteria and rapidly test their function. One method is by using hybridoma mRNA or splenic mRNA as a template for PCR amplification of such genes [Huse, et al., *Science* 246:1276 (1989)]. Thus, one can readily screen an antibody to insure that it has a sufficient binding affinity for the antigen. The binding affinity ($K_d$) should be at least about $10^{-7}$ 1/M, more preferably at least about $10^{-8}$ 1/M.

Figure 1B:
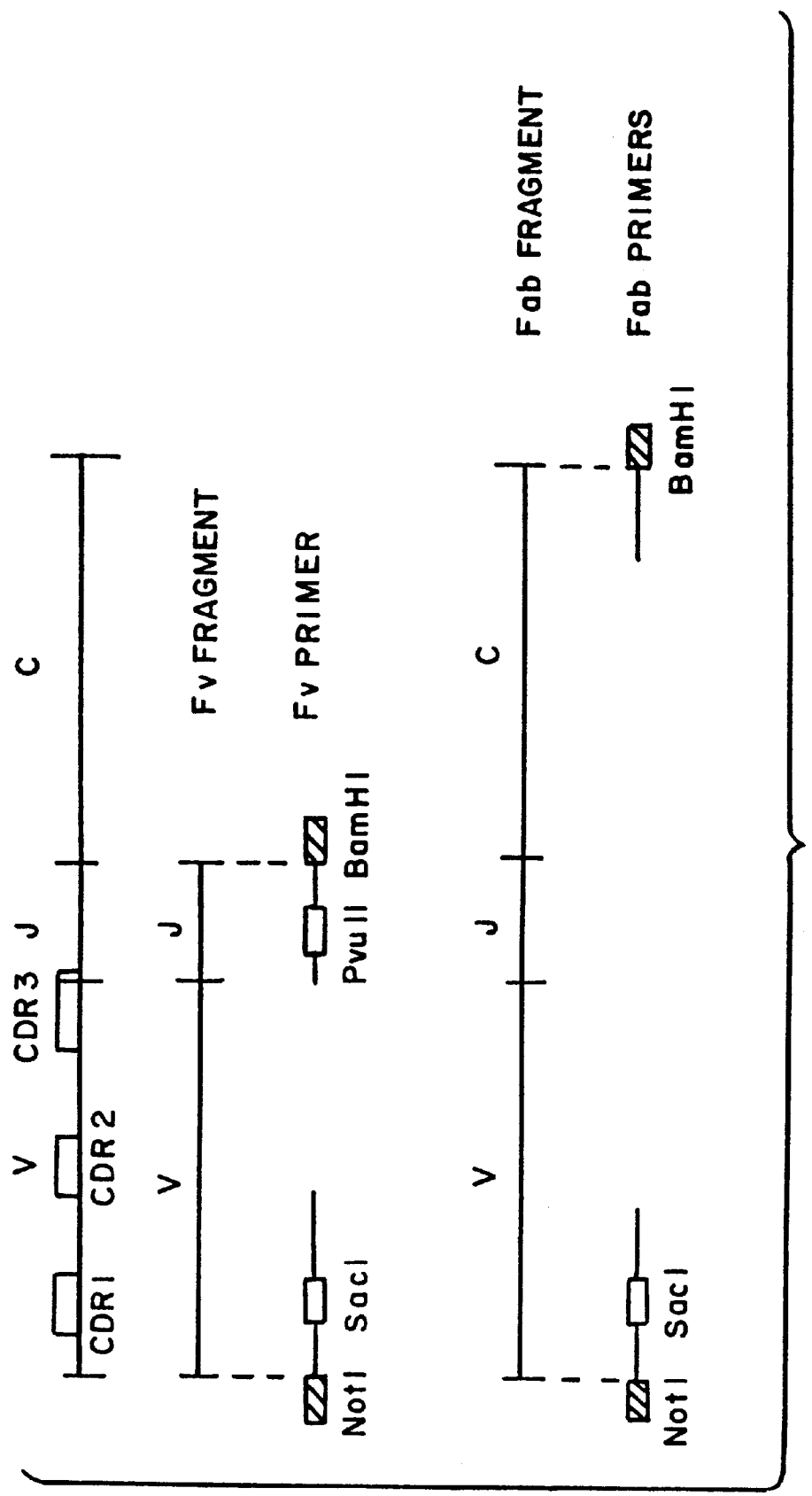

FIG. 1 shows the immunoglobulin genes and location of PCR primers. The light and heavy chain immunoglobulin genes are shown with V, D, and J segments noted as well as the constant regions. Also depicted are the CDR regions. The primers for PCR amplification can be RNA or genomic DNA as shown for both Fv and Fab gene amplification.

In one preferred embodiment, the genes encoding the light chain and heavy chain encode a linker to make a single chain antibody (sFv). The sFv will properly fold even under the reducing conditions sometimes encountered intracellularly. The sFv typically comprises a single peptide with the sequence $V_H$-linker-$V_L$ or $V_L$-linker-$V_H$. The linker is chosen to permit the heavy chain and light chain to bind together in their proper conformational orientation. See for example, Huston, J. S., et al., *Methods in Enzym.* 203:46–121 (1991), which is incorporated herein by reference. Thus, the linker should be able to span the 3.5 nm distance between its points of fusion to the variable domains without distortion of the native Fv conformation. The amino acid residues constituting the linker must be such that it can span this distance and should be 5 amino acids or larger. The amino acids chosen also need to be selected so that the linker is hydrophilic so it does not get buried into the antibody. Preferably, the linker should be at least about 10 residues in length. Still more preferably it should be about 15 residues. While the linker should not be too short, it also should not be too long as that can result in steric interference with the combining site. Thus, it preferably should be 25 residues or less. The linker (Gly-Gly-Gly-Gly-Ser)$_3$ (SEQ ID No:1) is a preferred linker that is widely applicable to many antibodies as it provides sufficient flexibility. Other linkers include Glu Ser Gly Arg Ser Gly Gly Gly Gly Ser Gly Gly GLy Gly Ser (SEQ ID NO:2), Glu Gly Lys Ser Ser Gly Ser Gly Ser Glu Ser Lys Ser Thr (SEQ ID NO:3), Glu Gly Lys Ser Ser Gly Ser Gly Ser Glu Ser Lys Ser Thr Gln (SEQ ID NO:4), Glu Gly Lys Ser Ser Gly Ser Gly Ser Glu Ser Lys Val Asp (SEQ ID NO:5), Gly Ser Thr Ser Gly Ser Gly Lys Ser Ser Glu Gly Lys Gly (SEQ ID NO:6), Lys Glu Ser Gly Ser Val Ser Ser Glu Gln Leu Ala Gln Phe Arg Ser Leu Asp (SEQ ID NO:7), and Glu Ser Gly Ser Val Ser Ser Glu Glu Leu Ala Phe Arg Ser Leu Asp (SEQ ID NO:8). Alternatively, you can take a 15-mer, such as the (Gly-Gly-Gly-Gly-Ser)$_3$ (SEQ ID NO:1) linker, although any sequence can be used and through mutagenesis randomize the amino acids in the linker, then with phage display vectors pull out the antibodies with the different linkers and screen for the highest affinity single chain antibody generated.

Preferably, the gene does not encode the normal leader sequence for the variable chains. It is preferable that the antibody does not encode a leader sequence. The nucleotides coding for the binding portion of the antibody preferably do not encode the antibody's secretory sequences (i.e. the sequences that cause the antibody to be secreted from the cell). Such sequences can be contained in the constant region. Preferably, one also does not use nucleotides encoding the entire constant region of the antibodies. More preferably, the gene encodes less than six amino acids of the constant region.

As discussed above, the immune system can prepare the antibody which will bind to a specific molecule such as a target protein by standard immunological techniques. For example, using the protein or an immunogenic fragment thereof or a peptide chemically synthesized based upon such protein. Any of these sequences can be conjugated, if desired, to keyhole limpet hemocyanin (KLH) and used to raise an antibody in animals such as a mice, rabbits, rats, and hamsters. Thereafter, the animals are sacrificed and their spleens are obtained. Monoclonal antibodies are produced by using standard fusion techniques for forming hybridoma cells. See, Kohler, G., et al. *Nature* 256:495 (1975). This typically involves fusing an antibody-producing cell (i.e., spleen) with an immortal cell line such as a myeloma cell to produce the hybrid cell.

Another method for preparing antibodies is by in vitro immunization techniques, such as using spleen cells, e.g., a culture of murine spleen cells, injecting an antigen, and then screening for an antibody produced to said antigen. With this method, as little as 0.1 micrograms of antigen can be used, although about 1 microgram/milliliter is preferred. For in vitro immunization, spleen cells are harvested, for example, mice spleen cells, and incubated at the desired amount, for example, $1 \times 10^7$ cells/milliliter, in medium plus with the desired antigen at a concentration typically around 1 microgram/milliliter. Thereafter, one of several adjuvants depending upon the results of the filter immunoplaque assay are added to the cell culture. These adjuvants include N-acetylmuramyl-L-alanyl-D-isoglutamine [Boss, *Methods in Enzymology* 121:27–33 (1986)]. Salmonella typhimurium mytogen [Technical Bulletin, Ribi ImmunoChem. Res. Inc., Hamilton, Mont.] or T-cell condition which can be produced by conventional techniques [See, Borrebaeck, C. A. K., *Mol. Immunol.* 21:841–845 (1984); Borrebaeck, C. A. K., *J. Immunol.* 136:3710–3715 (1986) or obtained commercially, for example, from Hannah Biologics, Inc. or Ribi ImmunoChem. Research Inc. The spleen cells are incubated with the antigen for four days and then harvested.

Single cell suspensions of the in vitro immunized mouse spleen cells are then incubated, for example on antigen-nitrocellulose membranes in microfilter plates, such as those available from Millipore, Corp. The antibodies produced are detected by using a label for the antibodies such as horseradish peroxidase-labeled second antibody, such as rabbit anti-mouse IgA, IgG, and IgM. In determining the isotype of the secreted antibodies, biotinylated rabbit anti-mouse heavy chain specific antibodies, such as from Zymed Lab., Inc. can be used followed by a horseradish peroxidase-avidin reagent, such as that available from Vector Lab.

The insoluble products of the enzymatic reaction are visualized as blue plaques on the membrane. These plaques are counted, for example, by using 25 times magnification. Nitrocellulose membrane of the microfilter plaques readily absorb a variety of antigens and the filtration unit used for the washing step is preferred because it facilitates the plaque assay.

One then screens the antibodies by standard techniques to find antibodies of interest. Cultures containing the antibodies of interest are grown and induced and the supernatants passed through a filter, for example, a 0.45 micromiter filter and then through a column, for example, an antigen affinity column or an anti-tag peptide column. The binding affinity is tested using a mini gel filtration technique. See, for example, Niedel, J., *Biol. Chem.* 256:9295 (1981). One can also use a second assay such as a radioimmunoassay using magnetic beads coupled with, for example, anti-rabbit IgG to separate free $^{125}$I-labeled antigen from $^{125}$I-labeled antigen bound by rabbit anti-tag peptide antibody. In a preferred alternative one can measure "on" rates and "off" rates using, for example, a biosensor-based analytical system such as "BIAcore" from Pharmacia Biosensor AB [See, *Nature* 361:186–187 (1993)].

This latter technique is preferred over in vivo immunization because the in vivo method typically requires about 50 micrograms of antigen per mouse per injection and there are usually two boosts following primary immunization for the in vivo method.

Alternatively, one can use a known antibody to the target protein. Thus, one can obtain antibodies to the desired target protein. Thereafter, a gene to at least the antigen binding portion of the antibody is synthesized as described below. The gene preferably will not contain the normal signal peptide sequences. In some preferred embodiments it will also encode an intracellular localization sequence such as one for the endoplasmic reticulum, nucleus, nucleolar, etc. When you want expression in the ER normal antibody secretory system such as the endoplasmic reticulum, golgi apparatus a leader sequence should be used. To retain such antibodies at a specific place, a localization sequence such as the KDEL sequence may be used. In some embodiments the antibody gene preferably also does not encode functional secretory sequences.

Antibody genes can be prepared based upon the present disclosure by using known techniques.

Using any of these antibodies, one can construct $V_H$ and $V_L$ genes. For instance, creating $V_H$ and $V_L$ libraries from murine spleen cells that have been immunized either by the above-described in vitro immunization technique or by conventional in vivo immunization and from hybridoma cell lines that have already been produced or are commercially available. One can also use commercially available $V_H$ and $V_L$ libraries. One method involves using the spleen cells to obtain mRNA which is used to synthesis by cDNA. Double stranded cDNA can be made by using PCR to amplify the variable region with a degenative N terminal V region primer and a J region primer or with $V_H$ family specific primers, e.g., mouse-12, human-7.

For example, the genes of the $V_H$ and $V_L$ domains of a broadly neutralizing antibody to the envelope glycoprotein of HIV-1 such as F105 [Olshevsky, et al., *J. Virol.* 64:5701–5707 (1990); Thali, et al., *J. Virol.* 65:6188–6193 (1991); and Posner, et al., *J. Immunol.* 146:4325–4332 (1991)) can be cloned and sequenced. The first strand cDNA can be synthesized from total RNA by using oligo dT priming and the Moloney murine leukemia virus reverse transcriptase according to known procedures. This first strand cDNA is then used to perform PCR reactions. One would use typical PCR conditions, for example, 25 to 30 cycles, to amplify the cDNA of the immunoglobulin genes. DNA sequence analysis is then performed. [Sanger, et al., *PNAS USA* 79:5463–5467 (1977)].

Heavy chain primer pairs consist of a forward $V_H$ primer and a reverse $J_H$ primer, each containing convenient restriction sites for cloning. One could use, for example, the Kabat data base on immunoglobulins [Kabat, et al., supra] to analyze the amino acid and codon distribution found in the seven distinct human $V_H$ families. From this, the 35 base pair universal 5' $V_H$ primer is designed. One could use a primer such as TTT<u>GCGGCCGC</u>TCAGGTGCA(G/A)CTG <u>CTCGAGTC</u>(T/C)GG (SEQ ID NO:9), which is degenerate for two different nucleotides at two positions and will anneal to the 5' end of FR1 sequences. A restriction site such as the 5' Not I site (left-underlined) can be introduced for cloning the amplified DNA and is located 5' to the first codon to the $V_H$ gene. Similarly, a second restriction site such as an internal XhoI site can be introduced as well (right-underlined).

Similarly, a 66-base pair $J_H$ region oligonucleotide can be designed for reverse priming at the 3' end of the heavy chain variable gene, e.g., AGATCCGCCGCCACCGCTCCCAC-CACC<u>TCCGGA</u>GCCACCGCCACCTGA <u>GGTGACC</u> GTGACC (A/G) (G/T) GGT (SEQ ID NO:10). This primer additionally contains a 45 nucleotide sequence that encodes a linker, such as the (Gly-Gly-Gly-Gly-Ser)$_3$ (SEQ ID NO:1) interchange linker. This primer contains two degenerate positions with two nucleotides at each position based on the nucleotide sequence of the six human $J_H$ region minigenes. Restriction sites can be used, for example, a BspEI site (left-underlined) is introduced into the interchange linker for cohesive end ligation with the overlapping forward $V_{kappa}$ primer. An internal BsTEII site (right-underlined) is introduced as well for further linker exchange procedures.

A similar strategy using the 45 nucleotide interchange linker is incorporated into the design of the 69 nucleotide human $V_{kappa}$ primer. There are four families of human $V_{kappa}$ genes. The 5' $V_{kappa}$ primer GGTGGCGGTGGC <u>TCCGGA</u>GGTGGTGGGAGCGGTGGCGGCGGATCT <u>GAGCTC</u>(G/C)(T/A)G(A/C)TGACCCAGTCTCCA (SEQ ID NO:11), which will anneal to the 5' end of the FR1 sequence is degenerate at 3 positions (2 nucleotides each). The interchange linker portion can contain a BspEI site for cohesive end cloning with the reverse $J_H$ primer, other restriction sites can also be used. An internal SacI site (right-underlined) can be introduced as well to permit further linker exchange procedures.

The reverse 47 nucleotide $C_{kappa}$ primer (Kabat positions 109–113) GGG <u>TCTAGACTCGAGGATCCTTATTA</u> ACGCGTTGGTGCAGCCACAGT (SEQ ID NO:12) is designed to be complementary to the constant regions of kappa chains (Kabat positions 109–113). This primer will anneal to the 5' most end of the kappa constant region. The primer contains an internal MluI site (right-underlined) proceeding two stop codons. In addition, multiple restriction sites such as Bam HI XhoI/XbaI (left-underlined) can be introduced after the tandem stop codons. A similar reverse nucleotide C-kappa primer such as a 59 nucleotide primer can also be designed that will contain a signal for a particular intracellular site, such as a carboxy terminal endoplasmic reticulum retention signal, Ser-Glu-Lys-Asp-Glu-Leu (SEQ ID NO:13) (SEKDEL), GGG TCTAGACTCGAGGATCCTTATTACAGCTCGTCC-TTTTCGCTTGGTGCAGCCACAGT (SEQ ID NO:14). Similar multiple restriction sites (Bam HI XhoI/XbaI) can be introduced after the tandem stop codons.

After the primary nucleotide sequence is determined for both the heavy and kappa chain genes and the germ line genes are determined, a PCR primer can then be designed, based on the leader sequence of the $V_H$ 71–4 germ line gene. For example, the $V_H$ 71–4 leader primer TTTA CCATGGAACATCTGTGGTTC (SEQ ID NO:15) contains a 5' NcoI site (underlined). This leader primer (P-L) is used in conduction with a second $J_H$ primer for PCR amplification experiments. The 35 base pair $J_H$ region oligonucleotide is designed to contain the same sequence for reverse priming at the 3' end of the heavy chain variable gene, TTA GCGCGCTGAGGTGACCGTGACC(A/G)(G/T)GGT (SEQ ID NO:16). This primer contains two degenerate positions with two nucleotides at each position. A BssH II site (left-underlined) 3' to and immediately adjacent to the codon determining the last amino acid of the J region, allows convenient cloning at the 3' end of the $V_H$ gene. An internal BstE II site (right-underlined) is introduced as well. This sequence is used to amplify the $V_L$ sequence. The fragments amplified by the P-L (leader primer) and P linker (reverse primer) and P-K ($V_2$ primer) and P-CK primers (reverse CK primer) are then cloned into an expression vector, such as the pRc/CMV (Invitrogen) and the resultant recombinant contains a signal peptide, $V_H$ interchain linker and $V_L$ sequences under the control of a promter, such as the CMV promoter. The skilled artisan can readily choose other promoters that will express the gene in the cell system of choice, for example, a mammalian cell, preferably human cells.

This single chain antibody can be prepared based upon the present disclosure by any of a number of known means. For example, the $V_H/J_H$-ICL and ICL-$V_{kappa}/C_{kappa}$ PCR fragments are digested with Not I/Bsp EI and Bsp EI/Xba I, respectively and cloned into a plasmid such as pSL1180 (Pharmacia) using SURE bacteria (Strategy) as hosts. The resulting sFv is restriction enzyme digested and the Not I/Bgl II fragment is cloned into the Not I/Bam HI site that is located 3' to the pelB signal peptide in a pET expression vector. The resulting plasmid is then transformed into the appropriate host, such as BL21 (DE3). Plasmid fragments are obtained after suitable times, for example, 2 to 4 hours after induction at 24° with 0.2 mM IPTG and tested for its ability to bind its target, e.g., gp120 binding activity, by standard techniques, e.g., ELISA using gp120 (American Biotechnology, Inc.) coated ELISA plates (Dynatech Labs) and detection with alkaline phosphatase coupled affinity column purified goat anti-human kappa chain antibody. The sFv bound gp120 is blocked by soluble CD4 and is absorbed to and eluted from a gp120 affinity column (Affi-Gel, BioRad, Inc.)

The $V_H$ 71–4 leader and a $J_H$-BssH II primers are used to PCR amplify an intronless fragment containing the leader peptide and rearranged heavy chain gene. The fragment is blunt end cloned in the forward direction into an Eco RV site in a plasmid, for example, pSL1180. Subsequently, a Nco I/Bst EII fragment is obtained and combined with the Bst EII/Sph I fragment of e.g., F105 sFv from pSL1180 in a three piece ligation with Nco I/SpH I digested pSL1180 to produce the $V_H$ 71–4/SCA. A $V_H$ 71–4 SCA containing the carboxyl-terminal SEKDEL sequence can be constructed by using a ICL-$V_{kappa}$-SEKDEL PCR product that is blunt and cloned in the forward direction into an Eco RV site in pSL1180. The fragment is removed by Bsp E I/Xba I digestion and combined with the Nco I/Bsp EI fragment of $V_H$ 71–4/SCA in a three part ligation with Nco I/Xba I digested pSL1180 to produce $V_H$ 71–4/KDEL. Before cloning into pRC/CMV (Invitrogen)) a Eco RI to Hind III conversion linker is introduced into Eco RI digested pSL 1180 containing the two single chain antibodies. Subsequently, a Hind III/Xba I fragment from both single chain antibodies is obtained and cloned into Hind III/XBa I digested pRC/CMV to produce pRC/SCA and pRC/KDEL.

Figure 2:
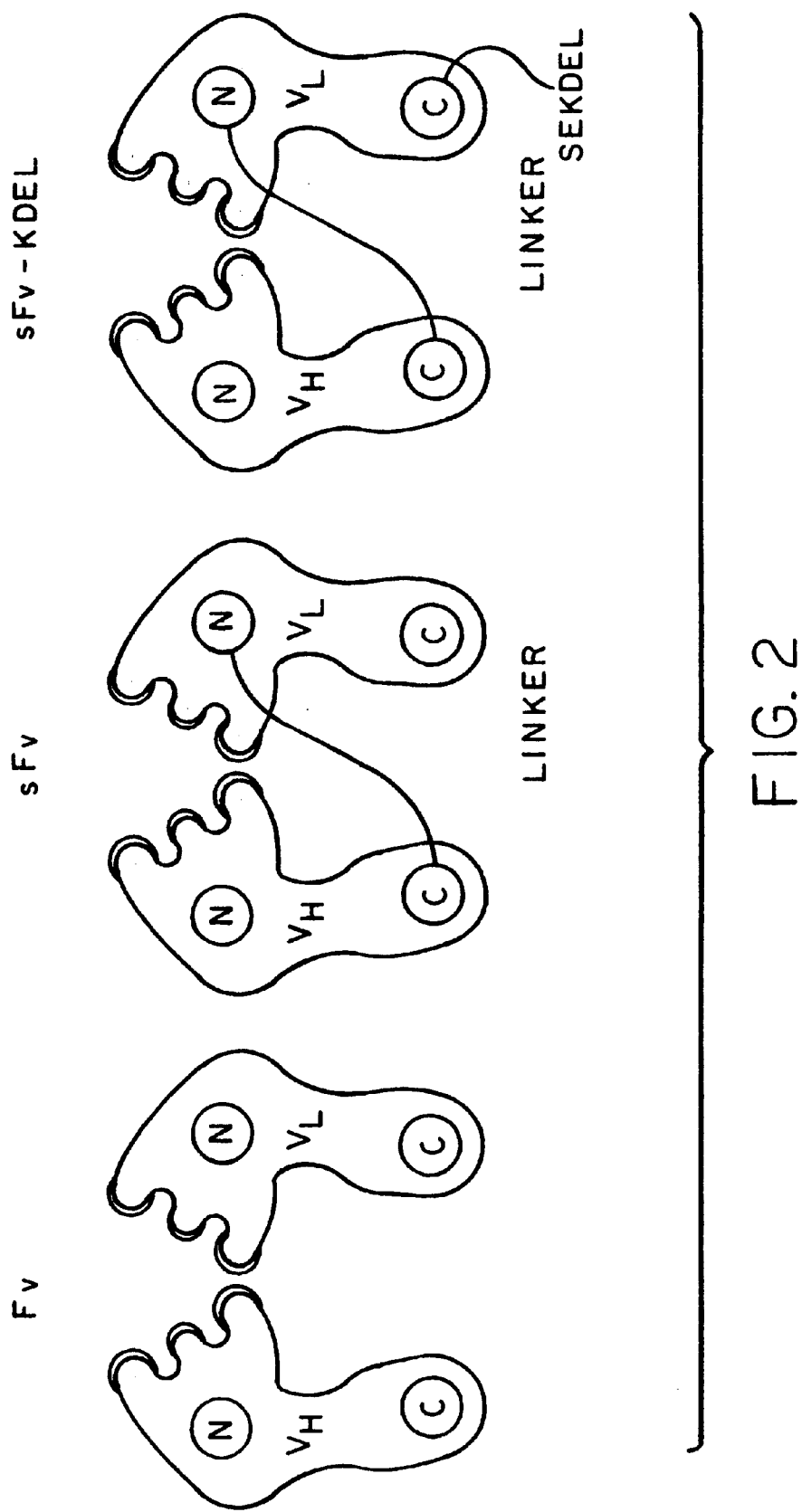
FIG. 2 is a diagram of the structures of Fv, sFv and sFv-KDEL of a broadly neutralizing antibody to envelope glycoprotein, F105. The three complementarity determining regions (CDRs) of each chain are shaded.

See, FIG. 2 which is a diagram of the structures of Fv, sFv and sFv-KDEL of one broadly neutralizing antibody, F105. The three complementarity determining regions (CDRs) of each chain are shaded.

Similar strategies can be used to prepare virtually any other antibodies. For example, using the combination of mRNA purification, single strand cDNA synthesis and PCR amplification using the $V_H$ and $J_H$ degenerative primers discussed above, an approximately 350 bp product can be obtained from spleen cells immunized against tat and anti-tat hybridoma cell lines. Using the same techniques, as described for heavy chains, a 320 bp $V_{kappa}$ gene product can be obtained from spleen cells immunized against tat and the anti-tat hybridoma cell lines using the $V_{kappa}$ and $J_{kappa}$ degenerative primers, discussed above. Once obtained, the $V_H$ and $V_L$ domains can be used to construct sFv, Fv or Fab fragments.

A preferred target is one processed by the endoplasmic reticulum, where proteins are typically made.

However, there are instances where a greater degree of intracellular specificity is desired. For example, with targeting nuclear proteins, RNA, DNA or cellular proteins or nucleic acids that are subsequently processed. For example, with virally encoded proteins such as lentiviruses structural proteins are typically cytoplasmically expressed, whereas regulatory proteins can be expressed in or near the nucleus. Thus, one preferably uses localization sequences for such targets. Our antibodies can be delivered intracellularly and can be expressed there and bind to a target protein.

Localization sequences have been divided into routing signals, sorting signals, retention or salvage signals and membrane topology-stop transfer signals. [Pugsley, A. P., Protein Targeting, Academic Press, Inc. (1989)]. For example, in order to direct the antibody to a specific location, one can use specific localization sequences. For example, signals such as Lys Asp Glu Leu (SEQ ID NO:17) [Munro, et al., Cell 48:899–907 (1987)] Asp Asp Glu Leu (SEQ ID NO:18), Asp Glu Glu Leu (SEQ ID NO:19), Gln Glu Asp Leu (SEQ ID NO:20) and Arg Asp Glu Leu (SEQ ID NO:21) [Hangejorden, et al., J. Biol. Chem. 266:6015 (1991), for the endoplasmic retriculum; Pro Lys Lys Lys Arg Lys Val (SEQ ID NO:22) [Lanford, et al. Cell 46:575 (1986)] Pro Gln Lys Lys Ile Lys Ser (SEQ ID NO:23) (Stanton, L. W., et al., Proc. Natl. Acad. Sci U.S.A. 83:1772 (1986); Gln Pro Lys Lys Pro (SEQ ID NO:24) [Harlow, et al., Mol. Cell Biol. 5:1605 1985], Arg Lys Lys Arg (SEQ ID NO:56), for the nucleus; and Arg Lys Lys Arg Arg Gln Arg Arg Arg Ala His Gln (SEQ ID NO:25), [Seomi, et al., J. Virology 64:1803 (1990)], Arg Gln Ala Arg Arg Asn Arg Arg Arg Arg Trp Arg Glu Arg Gln Arg (SEQ ID NO:26) [Kubota, et al., Biochem. and Biophy, Res. Comm. 162:963 (1989)], Met Pro Leu Thr Arg Arg Arg Pro Ala Ala Ser Gln Ala Leu Ala Pro Pro Thr Pro (SEQ ID NO:27) [Siomi, et al., Cell 55:197 (1988)] for the nucleolar region; Met Asp Asp Gln Arg Asp Leu Ile Ser Asn Asn Glu Gln Leu Pro (SEQ ID NO:28), [Bakke, et al., *Cell* 63:707–716 (1990)] for the endosomal compartment. See, Letourneur, et al., *Cell* 69:1183 (1992) for targetting liposomes. Myristolation sequences, can be used to direct the antibody to the plasma membrane. Table I, sets forth the amino-terminal sequences for known N-myristoylproteins and their subcellular location. In addition, as shown in Table I below, myristoylation sequences can be used to direct the antibodies to different subcellular locations such as the nuclear region. Localization sequences may also be used to direct antibodies to organelles, such as the mitochondria and the Golgi apparatus. The sequence Met Leu Phe Asn Leu Arg Xaa Xaa Leu Asn Asn Ala Ala Phe Arg His Gly His Asn Phe Met Val Arg Asn Phe Arg Cys Gly Gln Pro Leu Xaa (ID NO:29) can be used to direct the antibody to the mitochondrial matrix. (Pugsley, supra). See, Tang, et al., *J. Bio. Chem.* 207:10122, for localization of proteins to the Golgi apparatus. For example, it is known that tat is located in subnuclear and subnucleolar regions for infected cells. Thus, it is preferable that the tat antibody target the nuclear and/or nucleolar regions of the cell. Since this antibody is to be synthesized in the cytoplasm, it does not have a leader sequence. To target the nuclear and/or nucleolar regions it does need a localization sequence. Preferred nuclear targeting sequences are SV40 and preferred nucleolar targeting regions are tat nucleolar signals. Preferably, with viruses, e.g. HIV, the structural proteins are targeted in the cytoplasm such as envelope, and gag, whereas the regulatory proteins such as tat and rev, are targeted in the nucleus and nucleolar regions. More preferably, one would target rev using the rev nucleolar sequence Arg Gln Ala Arg Arg Asn Arg Arg Arg Arg Trp Arg Glu Arg Gln Arg (SEQ ID NO:26). [Kubota, supra]. For example, tax of HTLV-1 or HTLV-2 is also preferably searched for in the nucleus or nucleolus. If possible, it is preferable to use the localization signals of the target protein to direct the antibody to the desired location. For example, HIV-1 tat protein has a nucleolar localization signal, which is preferably used.

We have shown that by using localization sequences one can have the antibodies expressed and/or retained at an intracellular region where they do not ordinarily appear. For example, after expression we retained a tat antibody in the ER. Similarly, we have expressed anti-HIV envelope and anti-tat antibodies in the cytoplasm.

To demonstrate that single chain antibodies can be expressed at an intercellular region where they do not normally appear, we have expressed antibodies in the cytoplasm. For example, using cytoplasmically-expressed antibodies which have been modified on the 3' end to include additional localization signals, for instance, the SV40 nuclear localization signal for expression in the nucleus or translocation in the nucleus. For example, the F105 single chain antibody, which is typically expressed in the ER, was reamplified, containing a new 5' primer that anneals to the framework 1 region of the antibody. It therefore does not contain the leader peptide but contains a strong initiation start signal with a extra methionine at the 5' end as a start codon. This primer has a HINDIII site at the 5' end, followed by the NcoI site containing the Met start codon. (SEQ ID NO:57)
TTT-AAG-CTT-ACC-ATG-GCC-CAG-GTG-CAG-CTG-CAG-GAG-TCG-GG and codes for (SEQ ID NO: 58) Met Ala Gln Val Gln Leu Gln Glu Ser Gly. In addition to that methionine, which is right in the middle of the NcoI site, there is an additional amino acid, Ala. At the carboxy end of the signal peptide for bacterial expression, there is an Ala-Met-Ala cleavage. The cleavage into the periplasm occurs right after the second Ala and before the first amino acid of the framework. So, this is a verstaile primer that can be used or modified and used in many situations. For example, one can start with the NcoI site by the appropriate endonuclease and clone it into a bacterial expression vector. The same primer can be reused to amplify or to take the amplified material that still has the HIND III site and digest it with HIND III. Thus, one has a single chain antibody with the additional methionine as well as an Ala on the 5' end, that can be cloned into a vector, such as the pRC/CMV expression vector, transfected with lipofection, radiolabelled with $S^{35}$ methionine and immunoprecipitated with anti-kappa antibody. We have used the technique and obtained expression of an antibody to envelope in the cytoplasm. One can use this basic strategy and modify the antibody to also have a localization signal to transport the expressed antibody to a desired target. For example, using a single chain antibody, such as the tat and have it reamplified on the 5' end with a primer that anneals to the framework 1 region of the variable region and has a methionine residue for a start codon and an HINDIII site for cloning. This antibody gene is then reamplified for cloning, and expression in pRC/CMV. In addition, that antibody is further modified so that, in addition to using that new 5' primer for cytoplasmic expression, the C-terminus contains the SV40 nuclear localization signal. Thus, the antibody can be expressed in the cytoplasm and where we also used, for instance, the SV40 nuclear localization signal, and tranported into the nucleus.

We have used these two forms of the antibody, as well as two negative controls. The negative controls include different kappa chains, that were amplified from the same myeloma. We have made various anti-tat single chain antibody constructs capable of being expressed in the cytoplasm. From the myeloma cell line, producing the anti-tat monoclonal antibody, two different single chain antibodies containing the different kappa chains were also amplified with the SV40 nuclear localization sequence. Thus we prepared single chain antibodies to be expressed in the cytoplasm with or without a nuclear localization signal. To show specificity of the antibody, the incorrect light chain was also used. All four forms of that antibody have been expressed in eukarayotic cells. In these experiments, the four different plasmids were transfected into COS cells, and these experiments were performed with and without co-expressing a tat expresser plasmid. The KDEL envelope antibody was unstable until ligand or gp120 bound to it, so we confirmed that the same thing could occur in the cytoplasm. All four antibodies expressed with and without tat. Immunoprecipitating those radiolabelled lysates from COS cells with a pool of rabbit anti-mouse immunoglobulins and by autoradiography, it appears that in the presence of tat protein, a stronger immunoprecipitation of the antibodies occurs than in the absence of tat.

The localization signals can be located anywhere on the antibody so long as the signal is exposed in the antibody and its placement does not disrupt the binding ability of the antibody. For example, it can be placed at the carboxy or amino terminus or even on the linker between the heavy and light chain of a sFv antibody, providing it satisfies the above conditions.

TABLE I

| Amino-terminal sequence[1] | Subcellular location[a] | Protein | Ref. |
|---|---|---|---|
| GCVCSSNP SEQ ID NO: 30 | PM | p56[USTRATCK] | Marchildon, G.A., et al. Proc. Natl. Acad. Sci. USA 81:7679–82 (1984) Voronova, A.F., et al. Mol. Cell. Biol 4:2705–13 (1984) |
| GQTVTTPL SEQ ID NO: 31 | PM | Mul.V gag | Henderson, L.E., et al. Proc. Natl. Acad. Sci. USA 80:339–43 (1983) |
| GQELSQHE SEQ ID NO: 32 | PM | M-PMV gag | Rhee, S.S., et al. J. Virol. 61:1045–53 (1987) Schultz, A., et al. J. Virol. 46:355–61 (1983) |
| GNSPSYNP SEQ ID NO: 33 | PM | BLV gag | Schultz, A., et al. J. Virol. 133:431–37 (1984) |
| GVSGSKGQ SEQ ID NO: 34 | PM | MMTV gag | Schultz, A., et al. J. Virol., supra |
| GQTITTPL SEQ ID NO: 35 | PM | FCL.V gag | Schultz, A., et al. J. Virol., supra |
| GQTLTTPL SEQ ID NO: 36 | PM | BaEV gag | Schultz, A., et al. J. Virol., supra |
| GQIFSRSA SEQ ID NO: 37 | PM | HTLV-I gag | Ootsuyama, Y., et al. Jpn J. Cancer Res. 76:1132–35 (1985) |
| GQIHGLSP SEQ ID NO: 38 | PM | HTLV-II gag | Ootsuyama, Y., et al. supra |
| GARASVLS 39 | PM | HIV (HTLV-III) gag | Ratner, L., et al. Nature 313:277–84 (1985) |
| GCTLSAEE SEQ ID NO: 40 | PM | bovine brain G$_o$ α-subunit | Schultz, A.M., et al. Biochem. Biophys. Res. Commun. 146:1234–39 (1987) |
| GQNLSTSN SEQ ID NO: 41 | ER | Hepatitis B Virus pre-S1 | Persing, D.H., et al. J. Virol. 61:1672–77 (1987) Persing, D.H., et al. Science 234:1388–92 (1986) |
| GAALTILV SEQ ID NO: 42 | N | Polyoma Virus VP2 | Streuli, C.H., et al. Nature 326:619–22 (1987) |
| GAALTLLG SEQ ID NO: 43 | N | SV40 Virus VP2 | Streuli, C.H., et al. supra |
| GAQVSSQK SEQ ID NO: 44 | S,ER | Poliovirus VP4 | Chow, M., et al. Nature, 327:482–86 (1987) Paul, A.V., et al. Proc. Natl. Acad. Sci. USA 84:7827–31 (1987) |
| GAQLSRNT SEQ ID NO: 45 | S,ER | Bovine Enterovirus VP4 | Paul, A.V., et al. supra |
| GNAAAAKK SEQ ID NO: 46 | G,S,N,C | cAMP-dependent kinase | Carr, S.A., et al., Proc. Natl. Acad. Sci. USA 79:6128–31 (1982). |
| GNEASYPL SEQ ID NO: 47 | S,C | calcincurin B | Aitken, A., et al. FEBS Lett. 150:314–18 (1982) |
| GSSKSKPK SEQ ID NO: 48 | PM,C | p60[SFC] | Schultz, A.M., et al., Science 227:427–29 (1985) |

[a]Abbreviations are PM, plasma membranes, G, Golgi; N, Nuclear; C, Cytoskeleton; s, cytoplasm (soluble); M, membrane.
[1]To assist the reader, the standard single letter amino acid code is used in the Table, the amino acid sequences using the three-letter code are set out in the sequence listing.

In order to keep these antibodies in the cell, it is preferable that the expressed antibody does not contain the entire constant region domains. We believe that it is in this region where there are specific sequences which help in the secretion of the antibody from the cell. For example, we have constructed a broadly neutralizing sFv antibody to an envelope glycoprotein that contains only six amino acids of the constant region which is not secreted in any large amount by the cell, whereas the unaltered Fab antibody to such protein is secreted. This type of design to leave out such sequences can readily be accomplished in the selection and omission of nucleotides coding for the antibody. Although a broadly neturalizing antibody was discussed in this example, the antibodies used do not have to be broadly neutralizing. Neutralization is not required, rather, the antibody needs to bind to the target. Thus, one preferably looks for a epitope on the molecule that is conserved and accessible.

Alternatively, where the secretory signal is retained, the use of intracellular retention sequences such as KDEL for the endoplasmic reticulum should keep most of the antibodies expressed within the cell.

We have found that the expressed sFv antibody will still bind to the BiP protein, which can assist in keeping the resultant antibody target complex within the cell.

In some embodiments one will use antibodies that will not be retained in a cell. For example, one can use a Fab to an envelope glycoprotein such as F105 Fab. The Fabs will bind to the envelope glycoprotein at various locations in and outside the cell as they are secreted. Accordingly, if the target molecule, in this example the envelope glycoprotein is not all bound at one location, the use of such a secretable antibody permits targetting of the protein at multiple locations. We have found that using cells such as COS cells stably transformed by the F105 Fab antibody gene we have been able to obtain constitutive expression of F105 Fabs. These cell lines secrete the Fabs at about 1–3 μg/ml. This amount can be changed as desired by the skilled artisan by using different enhancers and promoters. As aforesaid the secreted Fab can target the molecule at different intracellular locations as it is secreted. In addition, the Fab can also target any molecule that might have escaped from the cell, extracellularly. For example, as well as targeting envelope glycoprotein as it is being processed, thereby greatly reducing the amount of processed protein, it can also bind to gp120 on the free virion and stop it from infecting another CD4 receptor or an uninfected cell. For example, the use of these F105 Fabs in HIV infected COS cells has inhibited synctia formation.

As the term is used herein the gene for the antibody can encompass genes for the heavy chain and light chain regions. In addition, the gene is operably linked to a promoter or promters which results in its expression. Promoters that will permit expression in mammalian cells are well known and include CMV, a viral LTR such as the rous sarcoma virus LTR, HIV-LTR, HTLV-1 LTR, the SV40 early promoter, *E. coli* lac UV5 promoter and the herpes simplex tk virus promoter. This DNA sequence is described as the antibody cassette.

The antibody cassette is delivered to the cell by any of the known means. See for example, Miller, A. D., *Nature* 357:455–460 (1992); Anderson, W. F., *Science* 256:808–813 (1992); Wu, et al, *J. of Biol. Chem.* 263:14621–14624 (1988). For example, a cassette containing these antibody genes, such as the sFv gene, can be targeted to a particular cell by a number of techniques. In the discussion below we will discuss the sFv genes coding for HIV antibodies, which would be preferably introduced into $CD4^+$ T-cells. However, the techniques described can readily be used to introduce the antibody genes into other cells, preferably human cells. For example, using a mammalian expression vector, such as a Herpes vector, an adenovirus vector or a pox vector, a retroviral vector, a plasmid bound to an antibody, etc. These vectors can be used to transduce cells by standard techniques well known to the skilled artisan. Preferably, this cassette is introduced in the cell by using an HIV viral vector, which is defective in packaging HIV sequences, but will preferentially target HIV susceptable cells. In addition, one can use a promoter that will differentially express the gene in the desired target cell. For example, using an HIV-LTR as a promoter where the target is HIV infected cells. In such a case, the HIV viral proteins in the cell such as tat can result in enhanced expression of the antibody when compared to uninfected cells. In another embodiment one can transduce cells that are at greater risk for viral infection such as CD4 cells.

The intracellular expression of the antibody permits it to bind the target. This disrupts the functioning of the target, e.g., a protein, including the undesired functioning. For instance, expressing the sFv of a broadly neutralizing antibody to envelope glycoprotein can intracellularly block the transport and interaction with the CD4 molecules of the HIV-1 glycoprotein, as well as the cleavage of the protein. We cloned both the sFv without any targeting signal and that sFv antibody with an endoplasmic retriculum retention signal (KDEL). These were then intracellularly inserted into mammalian cells, for example, by using a mammalian cell expression vector, although a retroviral vector is preferred with this antibody construct. As another example, using an antibody specific for neu which is targeted to breast tissue can help keep the neu protein in the cell.

The expression of these antibodies should not harm the cells. In fact, if the "ligand" target antibody is not present the antibody can be designed so that it will degrade. For example, the antibody to envelope glycoprotein with a KDEL retention sequence was degraded soon after synthesis unless HIV-1 envelope glycoprotein was present to form an antibody-ligand complex. In contrast, the single chain antibody to the envelope glycoprotein expressed without the retention signal was not similarly degraded but rather could be detected after radiolabeling an immunoprecipitation with polyclonal antibody to human immunoglobulin K-chain or heavy chain in the transfected cells. In both instances, the transformed cells appear to have normal morphology and growth rates. See, for example, FIG. 4, which shows transformed COS cells, which were established by neomycin selection expressing either the single chain antibody or the single chain with the KDEL sequence, which is retained in the endoplasmic retriculum. This antibody bound to the HIV-1 gp160 protein and could be coprecipitated with either anti-K or anti-gp120. Very little gp120 was detected even in a four hour chase sample from the sFv transformed cell while a fraction of gp120 was detected in the vector transformed cells and in a lesser portion in sFv KDEL transformed cells (See, FIG. 5). Thus, showing that the expressed sFv antibody binds to the protein gp160 and prevents the gp160 protein from further processing. In a preferred embodiment, an antibody to gp41 would also be delivered to such a cell to target any gp160 protein that was cleaved.

An alternative strategy is to have the expression of the antibody under the control of an inducible promoter. Preferably, the promoter will be inducible by an effect of the target. For example, one can use a viral LTR such as an HIV LTR as a promoter. The HIV virus produces proteins, e.g. tat, which "turn on" the promoter.

As explained above the sFv-KDEL product although rapidly degraded without target present, did not appear to be rapidly degraded when the HIV-1 glycoprotein was present. Thus, an sFv-KDEL band became visable in a polyacrylmide gel after radiolabeling and immunoprecipitation. This protein also coprecipitated with the HIV-1 glycoprotein although a small portion of gp120 was detected, which suggests an incomplete block to the glycoprotein transport possibly due to the rapid degredation of newly synthesized antibody before binding to the ligand. Immunofluorescence staining for sFv-KDEL in the transformed cells, co-expressing HIV-1-glycoprotein showed an endoplasmic reticulum staining pattern suggesting that the antibody became stable after binding to its ligand and remained in the endoplasmic reticulum.

The presence of target protein also assists the antibody to fold to the correct conformational state. These antibody-ligand complexes as aforesaid, prevent the target from operating in its typical manner. For instance, cytopathic fusion mediated by the HIV-1 gp120/41 is inhibited in the cells. This is shown by cotransfecting $CD4^+$ Hela cells with the HIV-1 glycoprotein expresser pSVIII env and sFv or sFv-KDEL plasmid DNAs at a ratio of 1:5 or tranfecting the transformed cells with pSVIII. Cells having the intracellular antibody showed a significant reduction of synctium formation while no significant reduction of synctium formation was observed in cells transformed or transfected with the vector that did not express the antibody, which indicates that the intracellular antibody can inhibit the cytopathic fusion by blocking the transport of the HIV glycoprotein to the plasmid membrane and/or the interaction of the HIV-1 glycoprotein with the CD4 molecules on adjacent cells even if the sFv-gp120 complexes were able to reach the cell surface.

Furthermore, very few infectious HIV-1 particles were produced from these intracellular antibody-containing cells. The cells expressing the intracellular antibody were transfected with infectious HIV-1 proviral DNA and the supernatants from the transfected cells can be used to infect the CD4 human lymphocyte SupT1. A dramatically slower kinetics of infections is observed in such cells when compared with that from vector-transformed cells, although comparable amounts of p24 activity from the supernatants of all these cells were observed which may indicate that non-infectious HIV-1 particles can be produced in the absence of HIV-1 glycoprotein.

This demonstrates that one can use the present method to intervene in a viral infection such as an HIV-1 infection using an intracellularly expressed antibody such as an engineered single chain antibody and that by binding to the dysfunctional or undesired gene products, the undesirable effects could be alleviated. Using the same basic strategy one should be able to intervene in other viral and metabolic diseases such as infections by DNA virus such as herpes simplex and RNA viruses such as HTLV-1 and 2. Preferably, this method would be used against viruses that are of long duration, and/or not readily susceptible to other forms of treatment.

The present method permits a wide range of approaches, even against the same disease. For example, antibodies against reverse transcriptase can interfere with template binding functions of the protein [DeVico, A. L., et al. *J. of Biol. Che.* 266:6774–6779 (1991)]. Antibodies to this protein are known and include C2003 which binds to a sequence in the C-terminal portion of the p66 component [Ibid]. This antibody also binds to HIV-2 [DeVico, A. L., *AIDS Res & H. Retro* 5:51–60 (1989)]. Such antibodies can be screened for from patient sera [Neumuller, M., et al., * We need the CITE*] and antibodies cloned as described above.

Another approach is to target a critical nucleic acid sequence in the virus such as the TAR element. The tar element, which is responsive to tat, is located at the 5' end of messenger viral RNA. Tat binding to this tar element has been shown to result in a derepression of tar inhibition of translation in vitro. In addition, the tar element increases transcription, initiation and also acts as an anti-attenuator of transcription elongation. By directing an antibody against the tar sequence, inhibition of tat binding will occur and there will be a dramatic decrease in transcription efficiency. This will ultimately result in an inhibition or reduction of virus production. A similar approach can be used to produce antibodies against the rev responsive element (RRE). Rev controls the synthesis of viral structural proteins, including the capsid protein, replicative enzymes and the envelope glycoprotein. The rev protein controls virion protein expression by controlling the cytoplasma accumulation of RNA species. In the absence of rev activity, small multiply spliced viral RNA species accumulate, in the presence of rev, full-length and partially spliced envelope glycoprotein messenger RNA's accumulate. Antibodies directed against the RRE should inhibit rev binding to RRE and therefore, inhibit the major biological effect of rev. In summary, the rev protein regulates the synthesis of capsid, replicative enzymes, and envelope glycoprotein production by regulating the accumulation of messenger RNA species from which they are made. Structural protein messenger RNA's require binding of rev protein to the folded RNA structure called RRE for translocation from the nucleus to the cytoplasm. Inhibition of rev binding by an anti-rev antibody should prevent virus expression from infected cells. Such TAR or RRE antibodies can be synthesized using known technology based upon the disclosure. For example, one can screen an RNA library with an antibody to obtain the desired antibody.

It has been proposed that tumor formation and metastasis is dependent upon angiogenis (i.e., formation of new capillary blood vessels). [Folkman, et al., Origins of Human Cancer: A Comprehensive Review, Cold Spring Harbor Laboratory Press (1991)]. For example, human melanoma has been found to produce several proteins with angiogenic activity, including fibroblast growth factor (bFGF), transforming growth factor alpha (TGFa), and transforming growth factor beta. [Herlyn, et al., *Lab. Invest.* 56:461 (1987)]. By using such proteins as targets for intracellular antibodies, tumor formation and metastasis may be limited.

It has been suggested that alterations at positions 12, 13 or 61 of the ras p21 proteins result in tumor formation. Using the mutant protein as a target for an intracellular antibody, which can distinguish the oncogenic ras from proto-ras, should limit tumor formation. Antibodies capable of such specific binding are known in the art.

It is preferable to use a "cocktail" approach (i.e. mixture of antibodies) in dealing with undesired viral proteins, thereby targeting a variety of viral proteins at one time and making it more difficult for mutants to evolve which will produce functional target protein capable of avoiding the antibody. For example, a cocktail of antibodies to at least envelope glycoprotein and tat is preferred. Other cocktails include antibodies to reverse transcriptase, TAR, RRE, etc. Such "cocktails" can be administered together or by co-transfections. It is preferred that no more than about three proteins in the same intracellular region are targeted, preferably no more than about two. For example, targeting gp160 and gp41 at the endoplasmic reticulum. As long as another intracellular target is in a different cellular region, i.e. nucleus vs endoplasmic reticulum, it can also be targeted without having a detrimental effect on antibody production. One preferred cocktail of antibodies would be antibodies for at least one structural viral protein such as capsid or envelope and one for regulatory proteins such as HIV rev, tat, HTLV-1 or tax or for a nucleic acid sequence such as TAR or RRE.

Another preferred cocktail would be of antibodies to the same target, but at various intracellular locations. This could be done using different localization sequences. Thus, if some target is not bound to the antibody at one location and, for instance, is further processed, it can be targeted at a subsequent location. For example, with the envelope glycoprotein one could use localization sequences to target the protein at a number of points in its processing path. Alternatively, one could use multiple antibodies to target different epitopes of molecules. For example, using one antibody to target the CD4 binding region of an envelope glycoprotein and a second antibody to target the fusogenic domain of gp41.

For HIV encoded proteins one preferred vector would be to have at two antibodies to capsid or envelope proteins and at least one to a regulatory protein. For example, to gp160, gp41, tat and rev. Another cocktail would include antibodies to both the viral mRNA and the protein it encodes.

Other preferred HIV encoded target proteins are nef, vpr and for HIV-1 vpu, and for HIV-2 vpx. More preferably, nef and vpu. For example, the nef protein exists in the cytoplasm as well as attached to the inner surface of the plasma membrane. The protein is modified co-translationally by addition of myristic acid to the penultimate glycine residue of the amino terminus. The vpr protein has been found incorporated into the capsid virus. The vpu protein is located within the cytoplasm of cells and may be associated with sub-cellular organelles. Antibodies to these proteins can be made by the methodology described herein. Further, these proteins can be more specifically targeted by the skilled artisan based upon this disclosure by selection of appropriate localization sequences.

Thus, using the above-described methodology, one can treat mammals, preferably humans, suffering from an ailment caused by the expression or overexpression of specific proteins. One can use this method to treat viral and metabolic diseases. Individuals infected by viral diseases such as HIV, HTLV-1, HTLV-2, herpes can be treated. Similarly, individuals having malignant tumors or susceptible to malignant cellular transformation caused by a high level of a protein or proteins, an altered protein or proteins or a combination thereof can be treated. For example, one can target at least one of the antigens with an antibody that will specifically bind to such antigen. One delivers an effective amount of a gene capable of expressing the antibody under conditions which will permit its intracellular expression to cells susceptible to expression of the undesired target antigen. This method can be used as a prophylactic treatment to prevent or make it more difficult for such cells to be adversely effected by the undesired antigen, for example, by preventing processing of the protein, interaction by the undesired protein with other proteins, integration by the virus into the host cell, etc. Where a number of targets exist, one preferred target is proteins that are processed by the endoplasmic reticulum. Intracellular delivery of any of the antibody genes can be accomplished by using gene therapy techniques such as described above. The antibody can be any of the antibodies as discussed above. We discuss herein the use of this system to deliver antibody genes to a virally infected mammal, for example, a human infected with the HIV virus, but it should be understood that based upon the present disclosure, one can readily adapt such an approach to other systems, for example, an individual with malignantly transformed cells.

HIV infects CD4 positive human lymphocytes and other immune cells. By targeting such cells with an antibody that will bind to at least one HIV encoded target molecle, e.g. a protein, it is possible to treat an individual infected with the virus, slow and/or retard the spread of infection or prophylactically treat such cells to make it more difficult for them to become infected.

One can use any of the known forms of gene therapy to deliver genes to CD4 positive lymphocytes. For example, using a cell-specific gene transfer mechanism, which uses receptor-mediated endocytosis to carry RNA or DNA molecules into cells (See, for example, Wu & Wu, *J. Biol. Chem.* 262:4429–4432 (1987). A protein acting as a ligand is coupled to a poly-L-lysine, which then combines with RNA or DNA (the gene) to form soluble complexes by strong electrostatic interaction, whereby one can deliver the genes (i.e. the RNA or DNA) to the cells of interest such as CD4 cells. For example, using an antibody against gp120 or CD4 as the ligand, one can specifically target such cells. Indeed, such a method of in vivo gene transfer in addition to serving as a vector to deliver a therapeutic gene into HIV infected cells or cells susceptible of HIV infection, would also maintain its neutralizing activity. We have found that the internalization of antibodies after binding the gp120 or CD4 expressed on the cell surface is highly efficient.

The antibodies that are used to target the cells can be coupled to the polylysine to form an antibody-polylysine conjugate by ligation through disulfide bonds after modification with a reagent such as succinimidyl-3-(2-pyridyldithio) proprionate (SPDP). The antibody-polylysine-gene complexes are produced by mixing the antibody polylysine conjugates with a moiety carrying the antibody cassette i.e. the DNA sequence containing the antibody operably coupled to a promoter such as a plasmid or vector (FIG. 14). Preferably, one will use polylysines having an average chain length of about 60 to 500 lysine monomers. More preferably, the polylysine has an average chain length of about 90 to 450 lysine monomers.

As aforesaid, ligation with the antibodies can be accomplished using SPDP. First dithiopyridine groups will be introduced into both antibody or polylysine by means of SPDP and then the groups in the polylysine can be reduced to give free sulfhydryl compounds, which upon mixing with the antibodies modified as described above, react to give the desired disulfide bond conjugates. These conjugates can be purified by conventional techniques such as using cation exchange chromatography. For example, a Pharmacia Mono S column, HR 10/10. See, for example, FIG. 15. These conjugates are then mixed with the antibody cassette under conditions that will permit binding. For example, incubating for one hour at 25° C. and then dialyzation for 24 hours against 0.15 M saline through a membrane with a molecular weight limit as desired. Such membranes can be obtained, for example, from Spectrum Medical Industries, Los Angeles, Calif.

To treat the targeted cells, these vectors can be introduced to the cells in vitro with the transduced cells injected into the mammalian host or the vector can be injected into a mammalian host such as a human where it will bind to with the CD4 cell and then be taken up. To increase the efficiency of the gene expression in vivo, the antibody cassette can be part of an episomal mammalian expression vector. For example, a vector which contains the human Pappova virus (BK) origin of replication and the BK large T antigen for extra-chromosomal replication in mammalian cells, a vector which contains an Epstein-Barr (EB) virus origin of replication and nuclear antigen (EBNA-1) to allow high copy episomal replication. Other mammalian expression vectors such as herpes virus expression vectors, or pox virus expression vectors can also be used. Such vectors are available from a wide number of source, including Invitrogen Corp. The antibody cassette is inserted into the expression vectors by standard techniques, for example, using a restriction endonuclease and inserting it into a specific site in such mammalian expression vector. These expression vectors can be mixed with the antibody polysine conjuates and the resulting antibody-polysine-expression vector containing antibody cassette complexes can readily be made based upon the disclosure contained herein. One would inject a sufficient amount of these vectors to obtain a serum concentration ranging between about 0.05 $\mu$g/ml to 20 $\mu$g/ml of antibody conjugate. More preferably between about 0.1 $\mu$g/ml to 10 $\mu$g/ml. Still more preferably, between about 0.5 $\mu$g/ml to 10 $\mu$g/ml.

These vectors can be administered by any of a variety of means, for example, parenteral injection (intramuscular (I.M.), intraperitoneal (I.P.), intravenous (I.V.), intracranial (I.C.) or subcutaneous (S.C.)), oral or other known routes of administration. Parenteral injection is typically preferred.

The materials can be administrered in any means convenient, for example, it can be mixed with an inert carrier such as sucrose, lactose or starch. It can be in the form of tablets, capsules and pills. For parenteral administration, it will typically be injected in a sterile aqueous or non-aqueous solution, suspension or emulsion in association with a pharmaceutically-acceptable parenteral carrier such as physiological saline.

The present invention is further illustrated by the following examples. These examples are provided to aid in the understanding of the invention and are not construed as a limitation thereof.

EXAMPLES

A. Construction and Expression of a Broadly Neutralizing Antibody to the Envelope Glycoprotein 1. cDNA Synthesis and PCR Amplification of F105 Immunoglobulin Genes.

The F105 hybridoma was derived by fusion of EBV transformants with the HMMA2.11TG/0 cell line, a non-secreting human-mouse myeloma analogue [Posner, et al., *J. Immunol.* 146:4325–4332 (1991)]. First strand cDNA was synthesized in a 25-ul reaction from 5 ug of total RNA by using oligo(dT) priming and the Moloney murine-leukemia virus reverse transcriptase according to published protocols [Gusler, et al., *Gene* 25:263–269(1983)]. Five to ten percent of the first strand cDNA was used to perform the PCR reactions. The temperatures used for the PCR are: Melt 94° C., 1 min.; primer anneal 52° C., 2 min; primer extension 72°, 2 min. One min. ramp times were used except a 2 min. ramp time was used between annealing and extension.

25–30 thermal cycles were preformed. Ethidium bromide stained 2% agarose gels were used to separate the PCR fragments. The appropriate band was excised, gene cleaned (Bio 101, La Jolla, Calif.), Klenow repaired, restriction enzyme digested and used for cloning. At least three separate transformants of each PCR fragment were sequenced using both forward and reverse sequencing primers. DNA sequence analysis was performed by the method of Sanger [Sanger, et al., *J. Mol. Biol.* 183:161–178(1980)].

2. PCR Primer Design.

The heavy chain primer pair consists of a forward $V_H$ primer and a reverse $J_H$ primer, each containing convenient restriction sites for cloning. The Kabat database on immunoglobulins was used to analyze the amino acid and codon distribution found in the six distinct human $V_H$ families [Kabat, et al., supra]. Based on this analysis, the 35 base pair universal 5' $V_H$ primer was designed TTTGCGGCCGCTCAGGTGCA(G/A)CTG CTCGAGTC(T/C)GG (SEQ ID NO:9) that is degenerate for two different nucleotides at two positions and will anneal to the 5' end of FR1 sequences. A 5' Not I site (left-underlined) has been introduced for cloning the amplified DNA and is located 5' to the first codon of the $V_H$ gene. An internal Xho I site has been introduced as well (right-underlined).

Similarly, a 66 base pair $J_H$ region oligonucleotide has been designed for reverse priming at the 3' end of the heavy chain variable gene, AGATCCGCCGCCACCGCTC-CCACCACCTCCGGAGCCACCGCCACCTGA GGTGACCGTGACC(A/G) (G/T)GGT (SEQ ID NO:10). This primer additionally contains a 45 nucleotide sequence that encodes the (Gly-Gly-Gly-Gly-Ser)$_3$ (SEQ ID NO:1) interchain linker. Based on the nucleotide sequence of the six human $J_H$ region minigenes, this primer contains two degenerate positions with two nucleotides at each position. A BspE I site (left-underlined) has been introduced into the interchain linker for cohesive end ligation with the overlapping $V_{kappa}$ primer. An internal BstEII site (right-underlined) has been introduced as well for future linker exchange experiments.

A similar strategy, using the 45 nucleotide interchain linker, has been incorporated into the design of the 69 nucleotide human $V_{kappa}$ primer. There are four families of human $V_{kappa}$ genes. The 5' $V_{kappa}$ primer GGTGGCG-GTGGC TCCGGAGGTGGTGGGAGCGGTGGCGGCGGATCT GAGCTC(G/C)(T/A)G(A/C)TGACC CAGTCTCCA (SEQ ID NO:11), which will anneal to the 5' of the FR1 sequences, is degenerate at three positions (two nucleotides each). The interchain linker portion contains a BspE I site for cohesive end cloning with the reverse $J_H$ primer. An internal Sac I site (right-underlined) has been introduced as well for future linker exchange experiments.

The reverse 47 nucleotide $C_{kappa}$ primer (Kabat positions 109–113) GGGTCTAGACTCGAGGATCCTTATTA ACGCGTTGGTGCAGCCACAGT (SEQ ID NO:12) was designed to be complementary to the constant region of kappa chains (Kabat positions 109–113) (Kabat). This primer will anneal to the most 5' end of the kappa constant region. The primer contains an internal Mlu I site (right-underlined) preceeding two stop codons. In addition, multiple restriction sites (Bam HI/XhoI/XbaI) (left-underlined) were introduced after the tandem stop codons. A similar reverse 59 nucleotide $C_{kappa}$ primer was also designed that contains a carboxy-terminal endoplasmic reticulum retention signal Ser-Glu-Lys-Asp-Glu-Leu (SEQ ID NO:13) (SEKDEL) GGGTCTAGACTCGAGGATCCTTATTA-CAGCTCGTCCTTTTCGCTTGGTGCAGCCACAGT (SEQ ID NO:14). Similar multiple restriction sites (Bam HI/XhoI/XbaI) (underlined) were introduced after the tandem stop codons.

After the primary nucleotide sequence was determined for both the F105 heavy and kappa chain genes and the gene line genes were identified, a PCR primer was designed based on the leader sequences of the $V_H$ 71–4 (Lee, et al., *J. Mol. Biol.* 195:761–768 (1987) germ line gene. The $V_H$ 71–4 leader primer TTTACCATGGAACATCTGTGGTTC (SEQ ID NO:15) contains a 5' Nco I site (underlined). This leader primer was used in conjunction with a second $J_H$ primer for PCR amplification experiments. The 35 base pair $J_H$ region oligonucleotide was designed to contain the same sequence for reverse priming at the 3' end of the heavy chain variable gene, TTAGCGCGCTGA GGTGACCGTGACC(A/G)(G/T)GGT (SEQ ID NO:16). This primer contains two degenerate positions with two nucleotides at each position. A BssH II site (left-underlined) 3' to and immediately adjacent to the codon determining the last amino acid of the J region allows convenient cloning at the 3' end of the $V_H$ gene. An internal BstEII site (right-underlined) has been introduced as well.

3. Construction and Bacterial Expression of F105 Single Chain Antibodies

For construction of the initial F105 sFv for bacterial expression, the $V_H/J_H$-ICL and ICLV$_{kappa}$/C$_{kappa}$ PCR fragments were digested with NotI/BspEI and BspEi/XbaI, respectively, and cloned into plasmid pSL1180 (Pharmacia LKB, Biotech. Inc., Piscataway, N.J.) using SURE bacteria (Stratagenem, La Jolla, Calif.) as hosts. The resulting F105 sFv was restriction enzyme digested and the NotI/BglII fragment was cloned into the NotI/BamHI site that is located 3' to the pel B signal peptide in a pET expression vector. The resulting pETpelB F105sFv plasmid was transformed into BL21 (DE3) hosts. The sFv 105 protein is recognized by antiserum to both the human heavy and light kappa chains. The protein binds to purified gp120 as determined using an ELISA assay in which gp120 is fixed to a plastic surface. Periplasm fractions were obtained 2–4 hrs after induction at 24° with 0.2 mM IPTG and tested for gp120 binding activity by ELISA using gp120 (American Biotechnology, Inc.) coated ELISA plates (Dynatech Labs, Inc., Chantilly, Va.) and detection with alkaline phosphatase coupled affinity column purified goat anti-human kappa chain antibody (Fisher Scientific). The F105 sFv bound gp120, was blocked by soluble CD4, thereby showing that CD4 competes, and was absorbed to and eluted from a gp120 affinity column (Affi-Gel, BioRad, Inc.).

4 Construction and Eukaryotic Expression of F105 Single Chain Antibodies with and without SEKDEL Endoplasmic Retention Signal.

The $V_H$ 71–4 leader and $J_H$/BssHII primers were used to PCR amplify an intronless fragment containing the leader peptide and rearranged heavy chain gene. The fragment was blunt end cloned in the forward direction into an EcoRV site in pSL1180. Subsequently, a NcoI/BstEII fragment was obtained and combined with the BstEII/SphI fragment of F105 sFv from pSL1180 in a three piece ligation with NcoI/SphI digested pSL1180 to produce $V_H$ 71–4/SCA. For construction of the $V_H$ 71–4 SCA containing the carboxy-terminal SEKDEL sequence a ICL-V$_{kappa}$-SEKDEL PCR product was blunt end cloned in the forward direction into a EcoRV site in pSL1180. The fragment was removed by BspEI/XbaI digestion and combined with the NcoI/BspEI fragment of $V_H$ 71–4/SCA in a three piece ligation with NcoI/XbaI digested pSL1180 to produce $V_H$ 71–4/KDEL. Before cloning into pRC/CMV (Invitrogen) a EcoRI to HindIII conversion linker was introduced into EcoRI digested pSL1180 containing the two single chain antibodies. Subsequently, an HindIII/XbaI fragment from both single chain antibodies was obtained and cloned into HindIII/XbaI digested pRC/CMV to produce pRC/SCA and pRC/KDEL.

See, FIG. 2, which is a diagram of the structures of Fv, sFv and sFv-KDEL. The three complementarity determining regions (CDRs) of each chain are shaded.

5. Construction and Expression of other Envelope Antibodies

Two other broadly neutralizing single chain antibodies to the envelope glycoprotein were produced and expressed using the same basic procedure. These PCR primers go forward for the $V_H$ and reverse for $V_{kappa}$ and as a result an inner chain linker that now has 24 amino acids of $J_H$, 24 nucleotides and 24 base pairs of V-kappa is amplified.

One such antibody was a single chain antibody derived from the 1.7b human monoclonal antibody that is directed against a CD4 enhancing epitope on gp120. Our genetic analysis had determined that that the rearranged heavy chain of the 1.7b monoclonal antibody was derived from the $V_H1263$ germ line gene. A heavy chain primer directed against the leader sequence of the $V_H1263$ leader peptide was used. This primer, (SEQ ID NO. 59) TTT-AAG-CTT-ACC-ATG-GAC TGG-ACC-TGG-AGG was used in conjunction with a blunt-ended heavy chain $J_H$ primer for the 3' end, (SEQ ID NO:60) TGA-GGT-GAC-CGT-GAC-CAG-GGT to amplify the rearranged heavy chain including its leader sequence. The kappa-chain was similarly amplified. Using the method of overlap extension described above, we assembled a single chain antibody against the CD4 enhancing site on gp120.

In addition, we have used a leader primer directed against the leader sequence of the DP-35 germ line gene. This rearranged germ line gene is used by the monoclonal antibody 21H, that is also directed against the CD4 binding site on gp120.

The 21H leader primer was used in conjunction with the $J_H$ primer. The $J_H$ blunt end primer (SEQ ID NO:61) TTT-AAG-CTT-ACC-ATG-GAG-TTT-GGG-CTG-AGC-TGG was used to amplify the rearranged heavy chain of the 21H monoclonal antibody. In addition, appropriately designed lambda light chain primers were used to amplify the rearranged light chain of the 21H monoclonal antibody. The two purified PCR products were used for overlap extension with an appropriate inner chain linker that has been modified to contain the lambda sequence for assembly of the 21H single chain antibody to be expressed in eukaryotic cells. (SEQ ID NO:62) CTG-CGT-CAA-CAC-AGA-CTG-AGA-TCC-GCC is the foward primer that was used for amplification of the 21H lambda chain. (SEQ ID NO:63) CGA-GGG-GGY-RGC-CTT-GGG-CTG is the reverse primer directed against the most proximal constant lambda region, i.e. the 3' primer for the 21H lambda chain. (SEQ ID NO:64) TTT-TCT-AGA-TCY-TMT-GAA-CTG-ACT-CAG is the primer used to reamplify the inner chain linker of F105 to put a lambda variable region on it in place of the kappa variable region.

Namely, as shown in the prior example, we put a leader peptide, a leader primer and a blunt end JH primer to amplify the rearranged heavy chains that have the leader peptide at one end and the JH blunt end segment on the other end. The leader peptide had a HIND III site.

The rearranged heavy chain along with the inner chain linker was created by using primers (SEQ ID NO:65) GGA-ACC-CTG-GTC-ACG-GTC-ACC-TCA on the 5' end and (SEQ ID NO:66) TGG-AGA-CTG-CGT-CAT-CTC-GAG-TTC on the 3' end. This rearranged heavy chain was used in conjunction with the kappa chain in the case of the 1.7b to produce the single chain antibody with the leader sequence. The primers used for the 1.7b are (SEQ ID NO: 67) GAA-CTC-GAG-WTG-ACG-CAG-TCT-CCA, which anneal to the $V_{kappa}$ region and (SEQ ID NO: 68) GG-GTC-TAG--ACT-CGA-GGA-TCC-TTA-TTA-ACG-CGT-TGG-TGC-AGC-CAC-AGT, which will anneal to the most constant portion of the kappa chain.

After the three pieces are added together and assembled by overlap extension, the single chain antibodies have on the 5' end a HIND III cloning site and on the 3' end the XbaI cloning site. You digest the PCR assembled fragment by use of appropriate restriction enzymes according to manufacturers instructions and then clone it directly into the plasmid, such as pRC/CMV.

6. Construction and Expression of Mutant Antibodies

Using any of these broadly neutralizing antibodies, mutant antibodies can be generated. One can use standard mutagenisis techniques to result in cDNA coding for different amino acids in the variable regions of the heavy chain such as the CDR3 region.

The F105 single-chain antibody, which contained the immunoglobulin heavy chain leader peptide, was initially cloned into pSL1180 cloning vector as described above. To prepare this antibody for CDR3 replacement, the following methodology was performed. Because the antibody had been cloned into a NcoI/SphI site, removal of some stuffer DNA was required. Thus, the vector was digested with SpeI and NheI to remove the Not I site. Following self-ligation, colonies were selected that had this stuffer DNA removed by screening. The resultant plasmid contained the F105 single chain antibody with the leader peptide in reverse orientation with two unique restriction sites that flanked the heavy chain CDR3 region. On the 5' end of CDR3, a unique EagI site existed (SEQ ID NO:69) ACG-GCC-GTG-TAT-TAC TGT-GCG CGA) and on the 3' end of the heavy chain CDR3, a Bst EII site is present (SEQ ID NO:70) TGG GGC CAG GGA ACC-CYG-GTC ACS GTN WCC. The vector was digested with Eag I and Bst EII and a library of CDR3 regions were cloned in. The resultant transformants were digested with PVU2 and mutant antibodies were distinguished from wild type by the change in pattern after PVU2 digestion. A unique PVU2 site exists in heavy chain CDR3, therefore, in the mutant antibodies, that site is destroyed. Thus, the pattern would be different from wild type which contained wild type CDR3 that contained the PVU2 site.

For the construction of the synthetic CDR3, 3 primers were used. The 5' primer contains an Eag I site (SEQ ID NO:71) CGC-ACA-GTA-ATA-CAC. The 3' primer contains a Bst EII site (SEQ ID NO:72) GT-GAC-CGT-GAC-CGG-GGT). The CDR3 involves degenerative sequence of NNSx 15, wherein N is any nucleotide and S is C or G. This minimizes the number of stop codons and allow all 20 amino acids to be expressed at each of 15 positions (SEQ ID NO:73) G-GCC-GTG-TAT-TAC-TGT-GCG-CGA-NNS-TGG-GGC-CAG-GGA-ACC-CCG-GTC. Following kinasing of these three peptides as well as annealing by the methodology described above, the resultant peptide had double-strandedness on the framework nucleotides flanking the CDR3 and contained open restriction sites. The CDR3 itself remained single-stranded. Bacterial polymerase was allowed to fill in the gaps. See, Cwirla, S. E., et al. *Proc. Natl. Acad. Sci. USA* 87:6378–6382 (1990).

An alternative method by which this can be accomplished would be to PCR amplify this same oligo that we've created using the two short polymers as the annealing polymers to the long oligonucleotide that spans the CDR3 following amplification, the large oligonucleotide would be digested with EAGI and BstEII and then ligated in using a standard molecular biology techniques.

The unique CDR3 mutants were established by PVU2 digestion. Then the entire antibody cassette was removed by HINDIII-Xba I digestion, which removes the entire antibody cassette along with cloning sites. These mutant antibodies were then gel-purified, gene cleaned and cloned into pRC/CMV that had been digested with HIND III and Xba1. These resultant plasmids were then transfected by lipofection into COS cells as previously described. Thereafter, mutants having different binding affinities to the envelope glycoprotein were screened.

Using the above-described technique, six mutant sFv105 antibodies were produced in which the amino acids in the CDR 3 region of the heavy chain were replaced by random amino acids One of the six mutants designated R had a CDR3 region which coded for (SEQ ID NO:74) Leu-Thr-Leu-Ile-Ser-Ser-Arg-Leu-Arg-Leu-Ile-Ala-Val-Arg-Met.

These six mutants did not bind to the HIV-1 envelope protein.

7. Construction of Fab Neutralizing Antibody to Envelope Glycoprotein

Figure 3:
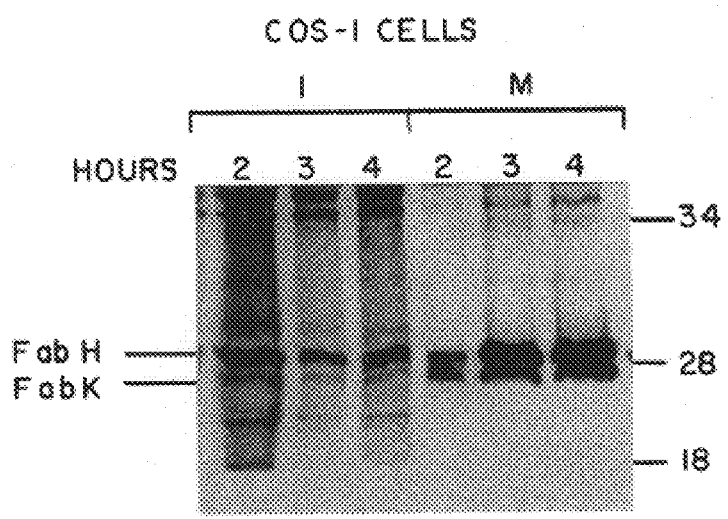
FIG. 3 are autoradiograms showing a pulse chase of COS-1 cells transfected with a plasmid expressing Fab fragments of a broadly neutralizing antibody to envelope glycoprotein.

A eukaryotic expression vector that is capable of producing high titers of human Fab fragments in COS-1 cells was also produced. This vector is based on the pRC/CMV vector described above, however, the Fd heavy chain and the light chain are cloned in tandem and each chain is under the control of a separate CMV promoter. The vector also conatins a neomycin gene for stable transfection. FIG. 3 shows pulse chase of COS-1 cells transfected with a plasmid expressing Fab fragments of F105 heavy (H) and light (L) chains. In FIG. 3, the first three lanes are the cell lysate and the second set of three lanes are from the cell medium. The lanes for each set are at 2, 3 and 4 hours of incubation. After 30 minutes labeling with $^{35}$S-Met, cell lysates (l) and medium (M) were harvested after the indicated times of incubation and radioimmunoprecipitates were obtained with a mixture of anti-human IgG$_1$ and anti-human kappa chain antibodies. The pulse chase experiment shown in FIG. 3 shows that high levels of Fab fragments of F105 are found in both intracellularly and in addition, the Fab fragments are actively secreted into the medium. Cell lysates and culture supernatants from these F105 Fab transfected COS-1 cells bind gp120 in an ELISA assay and both heavy and light chains can be readily immunoprecipitated with either anti-IgG$_1$ heavy chain (Fab H in FIG. 3) or anti-kappa chain antibody (Fab K in FIG. 3).

B. Construction and Expression of Anti-Tat Single Chain Antibodies

The same general methodology was used to express single chain antibodies to other antigens. A single chain antibody to the HIV-1 tat protein was generated as follows.

1. Heavy Chain Primer

The 5' forward V$_H$ primer consisted of a 55 base pair oligonucleotide with the following sequence:
CCC TCT AGA CAT ATG TGA ATT CCA CCA TGG CCC AGG T C/G A/C A A/G CTG CAG C/G AGTC A/T GG (SEQ ID NO:49).

The reverse murine J$_H$ primer beginning at the 5' end had the following sequence:
GGGGCGCGCTG A/C GGAGACGGTGACC A/G A/T GGT CCC T G/T C/G GCC CCAG (SEQ ID NO:50).

2. Murine Kappa Chain Primers

For PCR amplification of the murine kappa chain, containing the intrachain linker for the production of a single chain antibody, the following V$_{kappa}$ primer was produced.
TTTGGTCACCGTCTCCTCAGGTGGCG-GTGGCTCGGGCGGTGGTGGGTCGGGTG-GCGGCGGATCT G/C A A/C/T ATTCAGCTGAC C/A CA G/A T/A CTCCA (SEQ ID NO:51).

For use in conjunction with the above forward V$_{kappa}$ primer, two different reverse C$_{kappa}$ primers were produced. One was a 44 nucleotide primer having the following sequence:
GGGTCTAGACTCGAGGATCCTTATTATA-CAGTTGGTGCAGCATC (SEQ ID NO:52).

This primer will anneal from Kabat positions 110 to 115.

The second reverse C$_{kappa}$ primer was used for amplification of the C$_{kappa}$ chain that contains an SV40 nuclear localization signal at its 3' end. The primer had the following sequence.
GGGTCTAGACTCGAGGATCCTTAT-TAAACCTTACGTTTCTTCTTCGGCG-GAGTTACAGTTGGTGC AGCATC (SEQ ID NO:53).

This primer will anneal from Kabat positions 110 to 115 and is then followed by the SV40 nuclear localization signal having the following amino acid sequence:
Thr-Pro-Pro-Lys-Lys-Lys-Lys-Arg-Lys-Val (SEQ ID NO:54)

PCR Amplification

2–3 μg of total RNA isolated from anti-tat-III hybridomas was used to produce cDNA produced by random primer annealing in a 25 μg reaction. Five to ten percent of the single stranded cDNA was combined with the V$_H$ primer and V$_L$ primer and PCR was performed as described in Example 1. The annealing temperature for the PCR reaction was 56° C.

For PCR amplification of the light chain, V$_{kappa}$ primer containing the interchain linker was combined with either the C$_{kappa}$ primer alone, or the C$_{kappa}$ primer containing the SV40 nuclear localization signal. Annealing temperature for this reaction was 56° C.

For both light and heavy chain amplification, 30 rounds of PCR was used. These PCR products were gel purified on a 2% low melting point agarose gel. Because prior sequence analysis of the kappa chain showed an internal BstE-II site, a multistep cloning procedure was necessary. First, the heavy chain PCR product was Klenow kinase treated to repair the ends and assure that blunt ends were produced. The heavy chain fragment was then digested with XbaI. Likewise, the two different kappa chain constructs, with and without the SV40 nuclear localization signal, were Klenow kinase treated followed by digestion with XhoI. Equal molar amounts of these two fragments were mixed with the PSK+ vector that had been digested with XbaI and XhoI. This allowed for sticky end cloning at the extreme 5' and 3' ends, and blunt end cloning between the two PCR products.

Following successful cloning of the heavy and light chains, plasmid DNA was digested with BstE-II and the approximately 120 base pair BstE-II fragment was recovered and recloned into the same vector. This was necessary to remove extraneous nucleotides at the blunt end site. Several clones were obtained and the orientation of the BstE-II fragment was confirmed by PCR amplification using either the V$_H$, V$_{kappa}$ primers or V$_{kappa}$, C$_{kappa}$ primers set forth above.

For cloning into the eurkaryotic expression vector pRc/CMV (Invitrogen), an XbaII/ApaI fragment was obtained from the PSK+ vector and cloned into the PRC-CMV vector which had been digested with the same restriction enzymes.

To confirm the biological activity of the anti-tat single chain antibody obtained from this construct, the single chain antibody was reamplified with a new 3' primer to clone into the P-10-1 phagemid vector. Together with the original $V_H$ primer, a new reversed $C_{kappa}$ primer was used (ATT AGC GGC CGC TAC AGT TGG TGC AGC ATC) (SEQ ID NO:55).

The PRC-CMV anti-tat single chain antibody was transfected into COS cells using lypofection. Expression of the single chain antibody was found.

A second anti-tat sFv, which is similar to the above-described tat antibody except that it has a ER localization leader sequence was constructed as follows:

The genes of $V_H$ and $V_L$ domains of a murine anti-HIV-1 tat hybridoma cell line were cloned and DNA sequenced as described. A heavy chain leader primer (P-L) with the additional restriction enzyme site, (SEQ ID NO:75) 5'-TTTAAGCTTACCATGAACTTCGGGCTC-3', and reverse primer (P-J) corresponding to the 3' end of the heavy chain variable region, (SEQ ID NO:76) 5'TG(A/C) GGAGACGGTGACC(A/G)(A/T)GGTCCCT-3', were used to amplify the leader sequence and rearranged heavy chain sequences by polymerase chain-reaction as described above. A $V_L$ primer (P-K), corresponding to the 5' end sequence of the $V_L$, (SEQ ID NO:77) 5'-GAGCTCGTGCTCAC(C/A) CA(G/A)(T/A)CTCCA-3', and a reverse Ck primer (P-Ck) corresponding to the beginning of the constant region of kappa chain with a stop codon, (SEQ ID NO:78): 5'-GGGTCTAGACTCGAGGATCCTTATTATACAGTT-GGTGCAGCATC-3', were used to amplify the $V_L$ sequence. A 93 bp interchain linker was amplified using primers perfectly complementary to the (P-J) and (P-K) primers and containing the internal interchain linker sequence (Gly-Gly-Gly-Gly-Ser)$_3$. The three fragments were gel purified and the anti-tat sFv was produced by overlap extension by the methodology of Clackson, T., et al. [Nature 352:624 (1991)]. The assembled anti-tat sFv signal sequence was cloned into pRC/CMV and the DNA sequence was confirmed (Sanger, F., et al. Proc. Natl. Acad. Sci USA 74:5463 (1977)].

C. Inhibition of Function by Intracellular Antibody

1. Ability of Antibodies to be Expressed in Mammalial Cells.

The ability of these proteins to be expressed in mammalian cells was determined by transient transfection of COS-1 cells and a HeLa cell line that constitutively express the CD4 protein, HeLa-CD4 [Madden, P. J., et al., Cell 47:333–348 (1986); McDougal, J. S., et al., J. Immunol. 137:2937–2944 (1986)] as set forth below. It was found that whereas abundant amounts of the sFv105 protein are precipitated by anti-human heavy and light chain antibodies, very little of the sFv105-KDEL protein is detected in the transient expression assay.

Cells that constitutively express the sFv105 and sFv105-KDEL proteins (COS sFv105 and COS sFv105-KDEL) were made by transfection of COS-1 cells with the two plasmids followed by selection for neomycin resistance.

Figure 4:
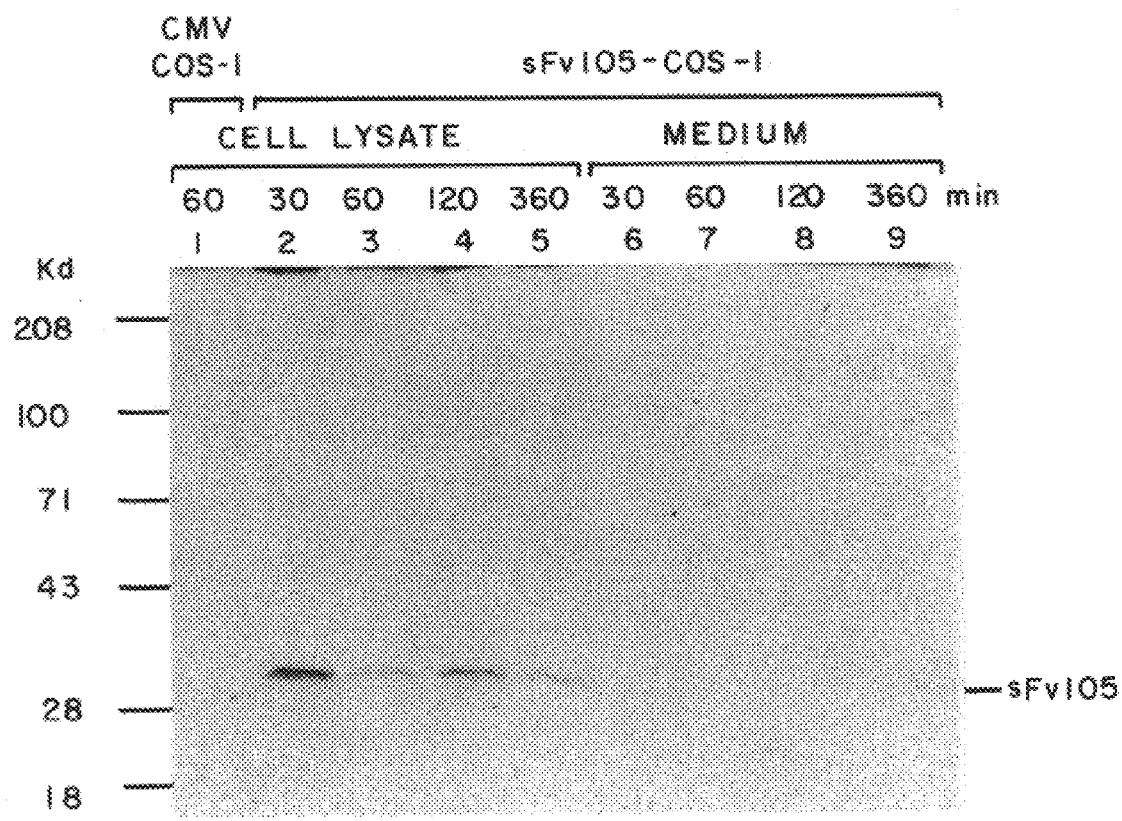
FIG. 4 is an autoradiograph of a 12.5% SDS-polyacrylamide gel showing proteins immunoprecipitated from cells lysate or culture medium.

COS-1 cells on 35 mm dishes were tranfected with 10 μg of pCMV-sFv or pCMV-sFv-KDEL or vector plasmid DNAs which contain neomycin resistance gene using lipofectin (BRL Corp) as described by Chen, S. Y., et al., J. Virol. 65:5902–5909 (1991). Two hours after transfection, 1.5 ml of Dulbecco's Modified Eagle's Medium (DMEM) supplemented with 10% fetal bovine serum were added to the cells and incubated for 48 hours. The transformed cells were selected in DMEM with 10% fetal bovine serum containing 500 μg/ml of G418 (BRL). The transformed cells were then grown on 6-well plates and metabolically labeled by incubation for 30 minutes in 0.5 ml cysteine-free containing 100 μci$^{35}$S-cysteine. The cells were then washed and incubated in DMEM containing 10 mM unlabeled cysteine. Proteins were immunoprecipitated from the cell lysates or medium and analyzed by electrophoresis. See, FIG. 4. These cells were pulse labeled for 30 minutes, chased and immunoprecipitated with anti-human immunoglobulin K-chain antibody from cell lysate or culture. The proteins were resolved by electrophoresis on a 12.5% SDS-polyacrylamide gel and visualized by autoradiography. (Laemmli, U.K., Nature 227:680–684 (1970)). Postion of the protein markers are shown in the figure. Lane 1, CMV-COS-1 cells, chase 60 minutes. Lanes 2–5 samples immunoprecipitated from cell lysates of COS sFv 105. Lanes 6–9 precipitated from the medium of sFv105-COS. Lanes 2 and 6 chase 30 minutes. Lanes 3 and 7 chase 60 minutes. Lanes 4 and 8 chase 120 minutes. Lanes 5 and 7 chase 360 minutes.

Immunofluorescent staining of the sFv or vector transformed cells was accomplished on 15 mM-diameter cover slips which were fixed in solution containing 95% ethanol and 5% acetic acid at −20° C. for 5 minutes. See, FIGS. 5A–D. The sFv 105 alone (A) or vector alone (D) transformed cells or sFv-KDEL transformed cells (B) cotransfected with 10 μg of the HIV-1 glycoprotein expresser plasmid pSVIII env described by Helseth, E. M., et al., J. Virol. 64:2416–2420 (1990) were stained with anti-human κ-chain antibody followed by incubation with fluorescein (FITC)-conjugated anti-rabbit IgG. For ER-staining, the vector-transformed cells were incubated with anti-BIP antibody followed by anti-mouse IgG-FITC (C). The vector transformed cells were incubated with anti-Bip antibody at 37° C. for 30 minutes followed by anti-rabbit IgG-FITC or anti-mouse IgG-FITC after washing with phosphate-buffered saline (PBS). After a final washing, the cells were mounted and observed on a Nikkon Microscopy with fluorescence optics at a magnification times 1100.

Figure 5A:
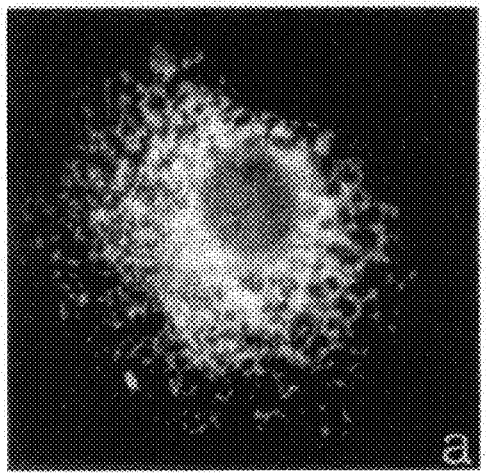
FIG. 5 shows immunofluorescent staining of transformed cells.
Figure 5B:
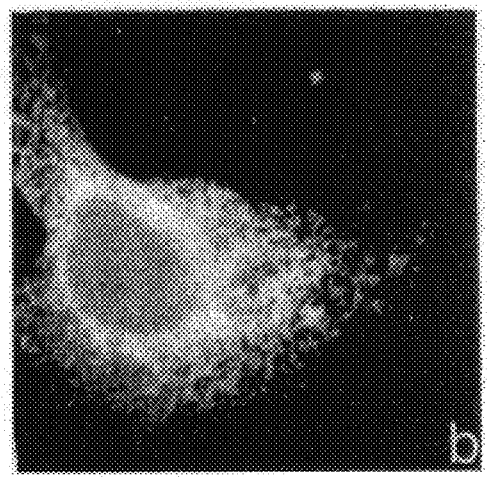
Figure 5C:
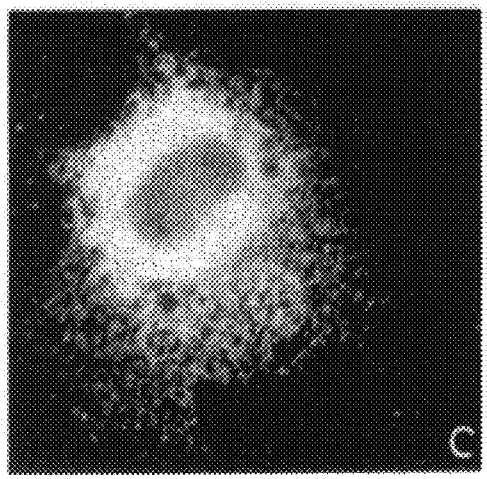
Figure 5D:
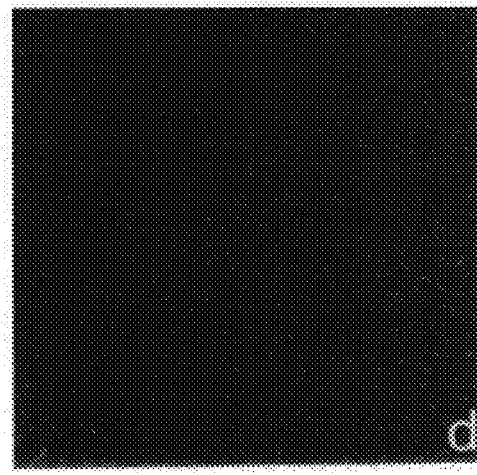

Thus, the location of the sFv105 protein within the cell could be determined. This antibody stains a tubular network throughout the cytoplasm typical of an ER resident protein (FIG. 5A). This pattern is the same as that obtained using an antibody to the ER resident protein immunoglobulin heavy chain-binding proteins, BiP [Wu, G. E., et al. Cell 33:77–83 (1983); Bole, D. G., et al., J. Cell Biol. 102:1558–1566 (1986); Dul, J. L, et al., Proc. Natl. Acad. Sci USA 87:8135–8139 (1990); Knittler, M. R., et al., The EMBO J. 11:1573–1581 (1992)] in the parental cell (FIG. 5c).

2. Ability of Antibody to Envelope Glycoprotein to Inhibit Envelope Protein Biosynthesis and Activity.

The ability of cell lines that constitutively express the sFv105 or sFv105-KDEL proteins to inhibit HIV-1 envelope protein biosynthesis and activity was determined by transfection of the COS sFv105 and COS sFv105-KDEL cells with a vector that expresses high levels of the envelope protein. Pulse chase analysis followed by immunoprecipitation of the envelope protein shows that a significant fraction of gp160 is cleaved to gp120 in the parental cell line during the four hour chase (FIG. 6). Although similar amounts of gp160 are made in the parental and COS sFv105 cells, very little gp120 is evident after the four hour chase (FIG. 6). The gp160 protein present in the COS sFv105 cells can be co-precipitated using an anti-human kappa chain antibody. This antibody does not precipitate the gp160 protein made in the parental COS-1 cell line. An antibody to the HIV-1 envelope glycoprotein also co-precipitates the sFv105 protein in cells that express gp160 (FIG. 6).

Figure 6A:
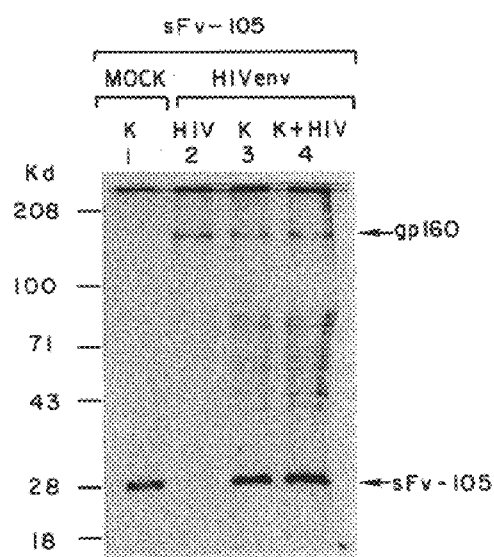
FIGS. 6A and B are autoradiograms of polyacrylamide gels showing sFv 105(A) or sFv 105-KDEL (B) coprecipitated with the HIV-1 glycoprotein.
Figure 6B:
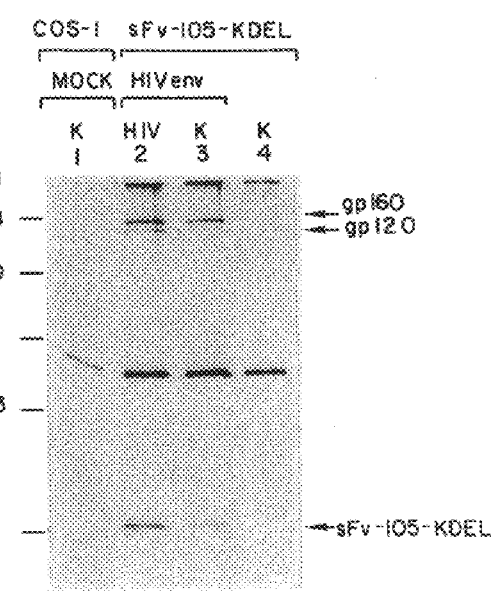

The transformed cells were transfected with 10 μg of pSVIIIenv plasma DNA and 2 μg of pSVIII tat expressing tat (See, Helseth, E. M., *J. Virol.* 64, *supra*) and pulse-labeled with $^{35}$S-cysteine for 30 minutes and chased for 4 hours. The cell lysates were immunoprecipitated with anti-K antibody or polyclonal sheep or rabbit anti-gp120 serum (AIDS Research and Reference Program). As described above, proteins were resolved by electrophoresis on 11% SDS-polyacrylamide gels and visualized by autoradiography as described above. See, FIG. 6. FIG. 6A shows cell lysates immunoprecipitated with polyclonal sheep, anti-gp120 serum and FIG. 6B shows cell lysates immunoprecipitated with rabbit anti-gp120 serum. FIG. 6A: Lane 1, mock transfected sFv105-COS-1 using anti-κ and anti-gp120 immunoprecipitated from HIV-1. Lanes 2–4, precipitated from the envelope transfected sFv105-COS-1. Lane 2, precipitated by anti-gp120. Lane 3, precipitated by chain antibody anti-κ. Lane 4, precipitated by anti-κ and anti-gp120 antibodies (AIDS Research and Reference Program). FIG. 6B, Lane 1, immunoprecipitated from mock transfected COS-1 using anti-κ2 chain and anti-gp120 protein antibodies. Lanes 2–3, precipitated from the envelope transfected sFv105-KDEL. Lane 2, precipitated by anti-gp120 antibody. Lane 3, precipitated by anti-κ chain antibody. Lane 4, precipitated from sFv105-KDEL cells using anti-κ chain and anti-gp120 antibodies.

Figure 8:
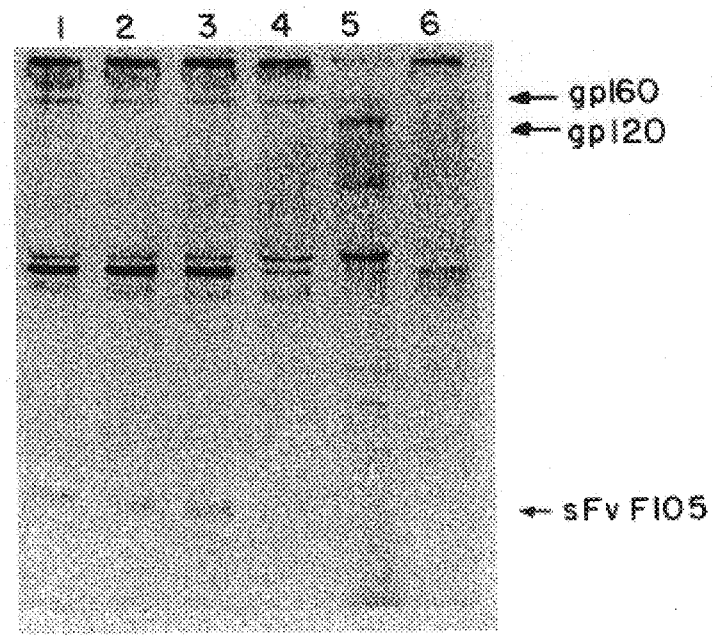
FIG. 8 are autoradiograms of a single chain antibody having a localization sequence showing specific binding to the HIV-1 glycoprotein in cells.

In the COS sFv105-KDEL cells, processing of gp160 to gp120 is partially inhibited (FIG. 8). FIG. 8 shows sFv105-KDEL specific binding to the HIV-1 glycoprotein in cells by autoradiograms of polyacrylamide gels showing that sFv105-KDEL protein is coprecipitated with the HIV-1 glycoprotein. Lane 1 shows lysates of mock transfected COS-1 cells precipitated with a mixture of anti-gp120 and anti-kappa chain antisera. Lanes 2–3 show lysates of COS sFv105-KDEL cells transfected with the envelope expressor plasmid pSVIIIENV. Lane 2 was precipitated with an anti-gp120 antiserum. Lane 3 was precipitated with an anti-kappa chain antiserum. Lane 4 shows lysate of COS sFv105-KDEL cells precipitated with a mixture of anti-gp120 and anti-kappa chain antisera. The amount of sFv105-KDEL protein precipitated by an anti-human kappa chain antibody is increased by the presence of gp160. The gp160 protein present in the COS sFv105-KDEL cells is also precipitated by an anti-kappa chain antibody. Antiserum that express gp160 is similar to the distribution of the sFv105 protein in COS sFv105 cells (FIG. 5B). Evidently, the sFv105-KDEL protein is stabilized by binding of gp160.

Co-immunoprecipitation experiments were performed with antiserum to the ER chaperone protein, BiP. The sFv105 protein is precipitated using an antiserum to the BiP protein. Although immunoglobulin heavy chains and light chains are known to bind to BiP (Wu, G. E., et al., *Cell* 33:77–83 (1983); Bole, D. G., et al., *J. Cell Biol.* 102:1558–1566 (1986); Dul, J. L., et al., *Proc. Natl. Acad. Sci. USA* 87:8135–8139 (1990); Knittler, M. R., et al., *The EMBO J.* 11:1573–1581 (1992)] several additional experiments were performed to exclude the possibility that inhibition of gp160 processing was due to non-specific activity of the sFv105 antibody.

Figure 9:
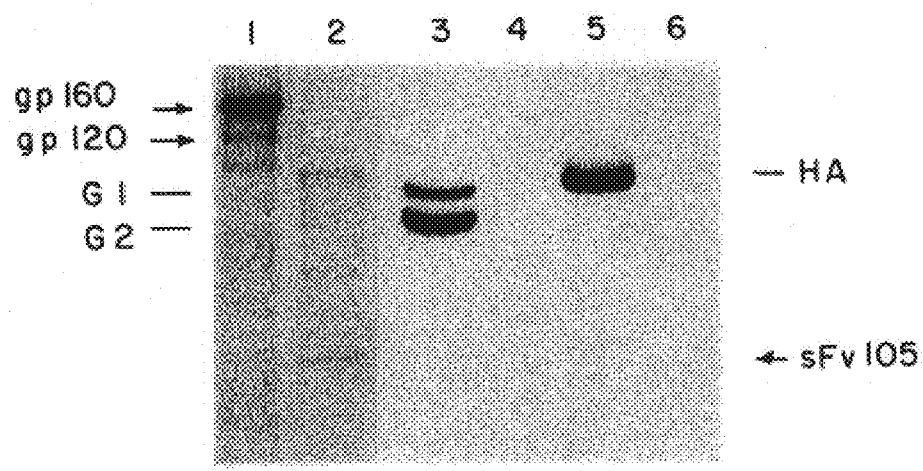
FIG. 9 are autoradiograms showing that a single chain antibody to a particular target is not coprecipitated with unrelated proteins.

The ability of cells that express a single chain antibody capable of binding sFv105 to inhibit processing of a mutant of the env protein was examined. For this purpose, the COS sFv105 cells were transfected with a plasmid that expresses a mutant of the envelope protein in which glutamic acid has been substituted with glutamine at position 370. This mutation has been previously shown to eliminate detectable binding of the envelope protein by the sFv105 parental antibody [Thali, M. C., et al., *J. Virol.* 66:5635–5641 (1992)]. The specificity of sFv105 binding to the HIV-1 envelope protein was also examined by transfecting the COS sFv105 cells with an envelope protein of the Punta Toro virus, a Bunyavirus or with the hemaglutinin of the WSN strain of the influenza A virus, an Orthomyxovirus. These two viral proteins have been previously shown to be processed in the ER and Golgi apparatus (Chen, S. Y., et al., *J. Virol.* 65:5902–5909 (1991); Hughey, P. G., et al., *J. Virol.* 66:5542–5552 (1992)]. Neither the Punta Toto nor the influenza virus proteins were precipitated with anti-human kappa chain antibodies which are shown to coprecipitate the sFv105 HIV-1 gp160 complex. FIG. 9, lanes 1 and 2 show that in contrast to the block in processing of the parental envelope protein in COS sFv105 cells, the mutant gp160 envelope protein is processed normally into gp120. Thus, FIG. 9 shows that sFv105 is not coprecipitated with unrelated proteins. The COS sFv cells were transfected with 10 μg of the mutant HIV-1 glycoprotein expresser 370E/D, which is not bound by F105 [Thali, M. C., et al. *J. Virol.* 66, supra], pulsed-labelled with $^{35}$S-cysteine for 30 minutes, and then chased for 4 hours. The proteins were immunoprecipitated either with anti-HIV-1 glycoprotein (lane 1) or anti-kappa chain antibody (lane 2). The COS-sFv cells were infected with 5 M.O.I of vaccinia virus encoding T7 polymerase for 2 hours and then transfected with 10 μg of plasmid DNAs PTV-G1-G2, which contains the genes of G1 and G2 glycoproteins of Punta Toro virus under the control of T7 promoter (Chen, S. Y., et al., *J. Virol.* 65, supra), or plasmid T7-HA, which contains the HA gene of the WSN strain of influenza A virus under the control of the T7 promoter [Chen, supra]. The cells were then pulse-labelled with $^{35}$S-cysteine for 30 minutes and chased for 4 hours. Lane 3 and 4: the lysates of PTV G1–G2 transfected cells immunoprecipitated with anti-PTV glycoprotein (Chen, supra) (Lane 3) or anti-kappa chain (Lane 4). FIG. 9 also shows that the processing of the Punta toto envelope protein is not affected by the expression of the sFv105 antibody (lanes 3–6).

Figure 10:
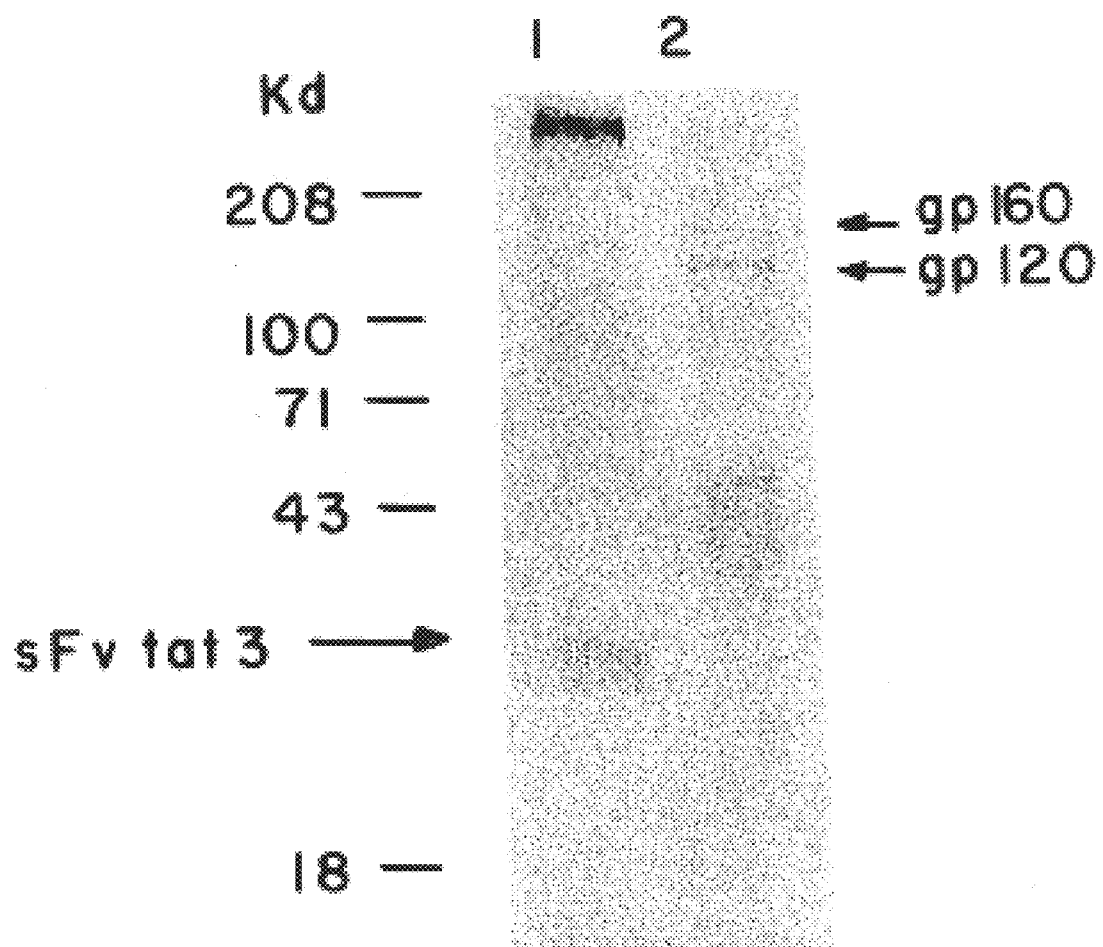
FIG. 10 are autoradiograms showing that an intracellularly retained anti-tat antibody does not bind HIV-1 glycoprotein.

The ability of other single chain antibodies that do not bind to gp160 to interfere with processing of the envelope protein was examined. Two different single chain antibodies were used. One such antibody is the single chain antibody derived from a murine monoclonal antibody that recognizes the HIV-1 tat protein. This anti-tat single chain antibody has been altered from the tat antibody's normal intracellular target to have a leader sequence which will target the ER. This antibody is also stably retained intracellulary in COS cells and is not secreted into the medium in a transient expression assay. The processing of gp160 to gp120 in COS cells was unaffected by cotransfection of a plasmid which expressed the HIV-1 glycoprotein with the plasmid that expressed the anti-tat sFv. Moreover, an anti-immunoglobulin antisera that precipitates the anti-tat sFv does not coprecipitate the HIV-1 envelope protein (See FIG. 10). FIG. 10 shows that an intracellularly retained anti-tat sFv does not bind HIV-1 glycoprotein. The COS cells were cotransfected with 10 μg of pSVIIIenv and 10 μg of pRC/CMV-sFvtat plasmid DNA, pulse-labelled with $^{35}$S-cysteine for 30 minutes and chased four hours. The proteins were immunoprecipitated with antimouse immunoglobulin antisera (Lane 1) or sheep anti-gp120 (Lane 2) and analyzed by SDS-PAGE. The six mutants of sFv105 produced in which all of the amino acids in the CDR3 region of the heavy chain were replaced by random amino acids and which do not bind the protein were also used. The processing of gp160 to gp120 in COS cells was unaffected by cotransfection of the plasmids that express these mutant proteins. The anti-immunoglobulin antisera did not coprecipitate the HIV-1 envelope protein.

Figure 7A:
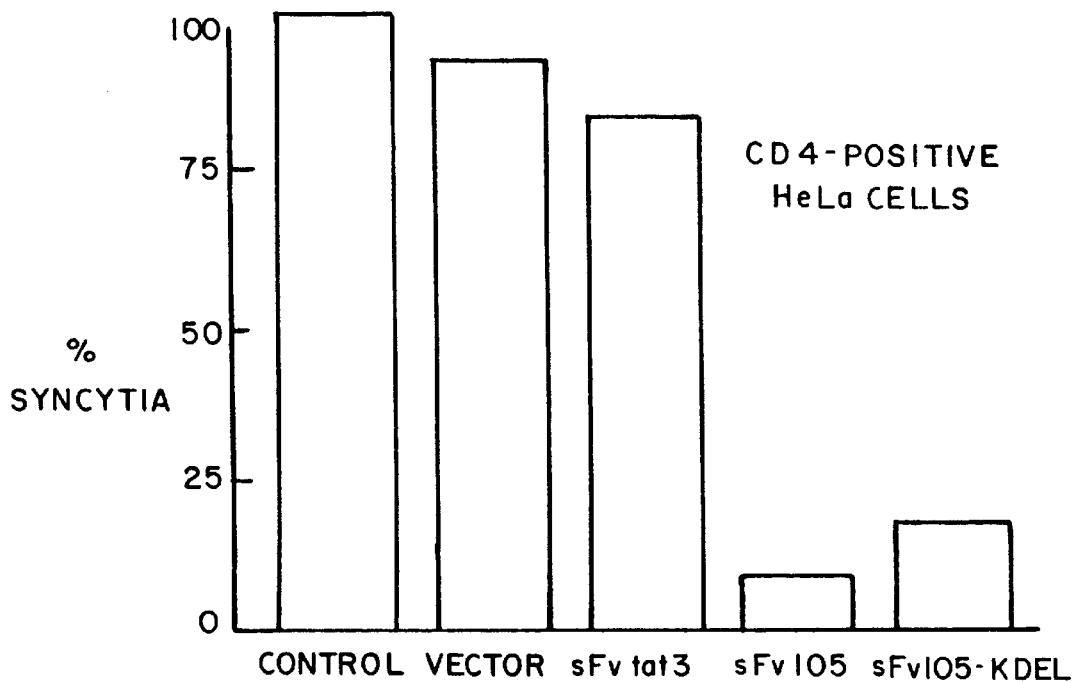
FIG. 7 shows the inhibition of the syncytium formation in cells expressing sFv or sFV-KDEL.
Figure 7B:
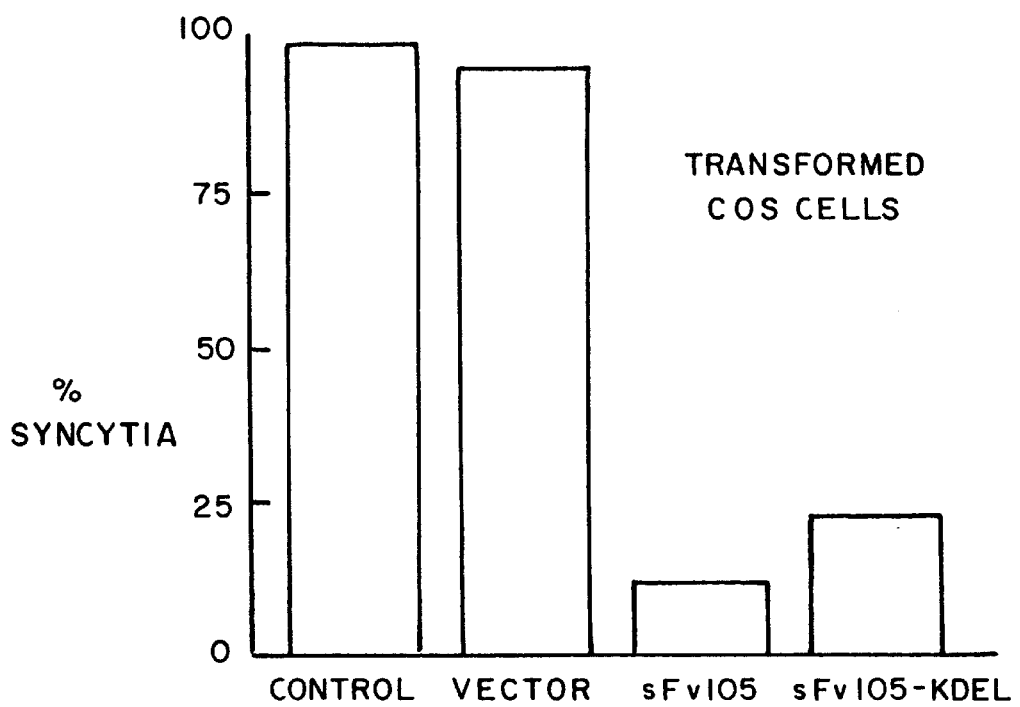

The ability of the sFv105 and sFv105-KDEL proteins to inhibit the function of the envelope protein was determined by measurement of the ability of cells transfected with the envelope gene to induce syncytium formation of CD4+ cells. In one set of experiments, the parental COS vector cells as well as the COS sFv105 and COS sFv105-KDEL cells were transfected with a plasmid that expresses a functional envelope glycoprotein. At two days post-transfection the cells were mixed at a ratio of about 1 to 10 with a human CD4+ T cell line, SupT1, that is susceptible to envelope mediated fusion. The extent of envelope mediated syncytium formation was reduced by 80–90% in cells which express either the sFv105 or sFv105-KDEL proteins (FIG. 7). Similar amounts of gp160 were made in all three lines as determined by metabolic labeling and precipitation of the transfected cultures. Reduction in syncytium formation was also observed upon co-transfection of the HeLa CD4+ cell line with a plasmid that expresses a functional envelope glycoprotein along with a second plasmid that expresses either the sFv105 or sFv105-KDEL proteins (FIG. 7). In contrast, there was no significant reduction in syncytium formation when the second plasmid that expresses the anti-tat sFv (FIG. 7).

CD4+Hela cells were cotransfected with 3 µg of pSFII-Ienv and 15 µg of vector or pCMV-sFv or pCMV-sFv-KDEL. Synctia were counted 30 hours post-tranfection. The transformed cells were transfected with 3 µg of pSVIIIenv which were incubated for 48 hours, then rinsed in PBS and incubated with 50 mM EDTA at 37° C. for 40 minutes. The cells were removed from the plate, washed with PBS, and resuspended in 2 ml of DMEM supplemented with 10% fetal calf serum. The cells were then added with about 2×10$^6$ SupT1 lymphocytes and incubated at 37° for 12 hours and synctia was scored. To examine the production of infectious HIV-1 by the transformed cells, COS, COS sFv105 and COS sFv105-KDEL cells were transfected with 5 µg infectious pSVIIIB DNA. The supernatants from the cells were harvested at day 4 of transfection and 1 ml of each of the supernatants was then inoculated with about 2×10$^6$ SupT1 cells for 12 hours. The SupT1 cells were then washed with DMEM twice and placed in the RPMI medium supplemented with 10% fetal bovine serum after 12 hours. The supernatants of the SupT1 cells were then harvested and the production of viral particles was measured by using a sensitive radioimmunoassay serum for the HIV-1 p24 capsid antigen protein (DuPont-NEN Inc.) following manufacturer's instructions. FIG. 7 shows a significant reduction of synctium formation in the CD4+ HeLa cells and the transformed COS cells expressing sFv or sFv-KDEL. The percentage of the values of synctia observed in the CD4+ HeLa cells or the vector transformed cells transfected with pSVIII env are shown.

To examine the ability of the sFv105 proteins to inhibit production of infectious virus, COS vector, COS sFv105, and COS sFv105-KDEL cells were transfected with a plasmid that contains a copy of the entire viral genome [Fisher, A. G., et al., *Nature* 316:262–265 (1985); Helseth, E. M., et al., *J. Virol.* 64:2416–2420 (1990)]. Four days post-transfection, the virus in the culture supernatant fluids was used to initiate infection of the sensitive indicator cell line SupT1. The supernatants of all three transfected cells lines were shown to contain similar amounts of the viral capsid protein, p24. Release of capsid proteins into the cell supernatant has previously been shown to occur in the absence of synthesis of the envelope glycoprotein as well as in the presence of envelope glycoproteins that contain processing defects and are therefore retained in the ER [McCune, J. M., et al., *Cell* 53:55–67 (1988); Ratner, L. N., et al., *AIDS Research and Human Retroviruses* 7:287–294 (1991)].

Figure 11:
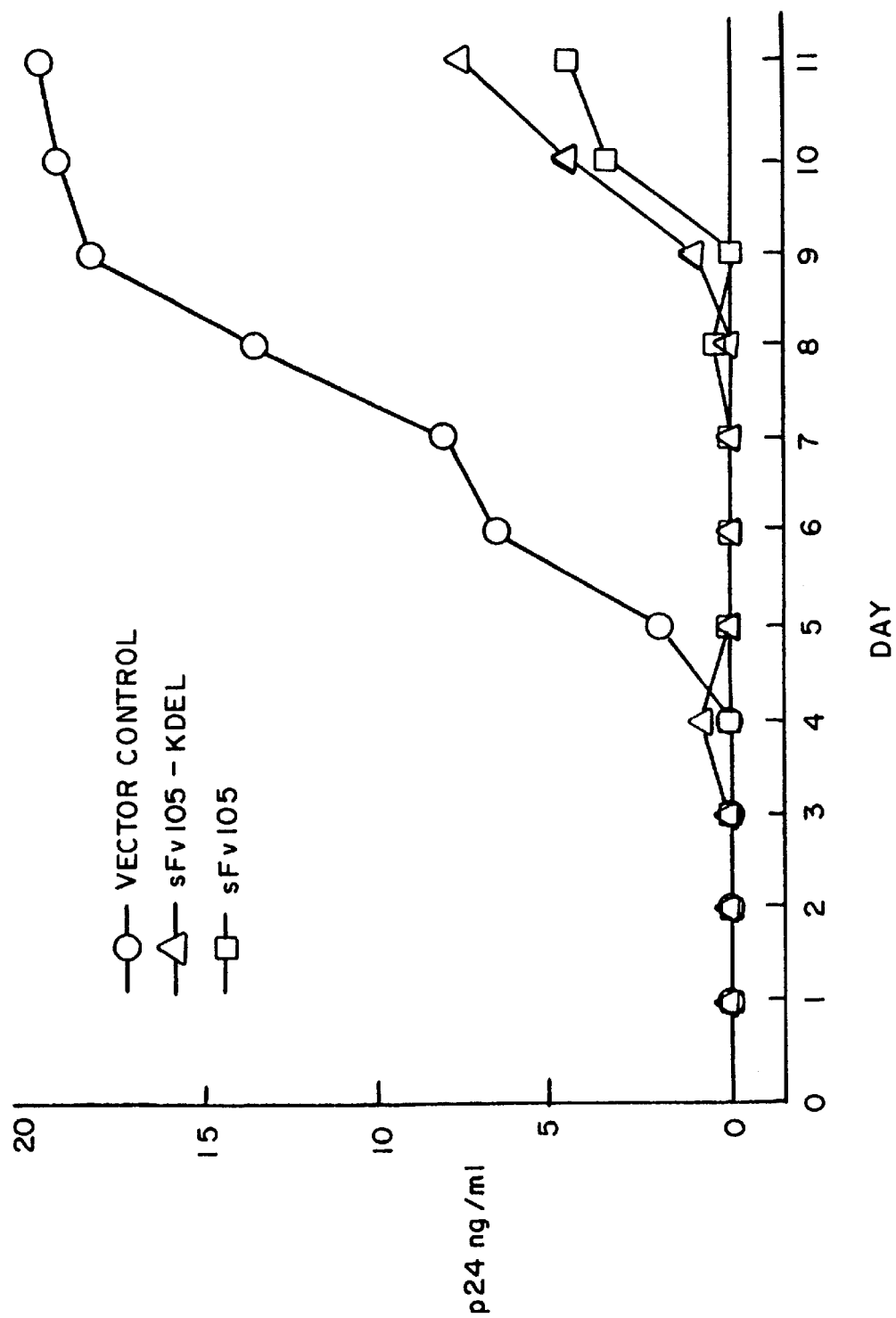
FIG. 11 shows the production of infectious HIV-1 in cells expressing sFv or sFv-KDEL.

FIG. 11 shows that virus replication in SupT1 cells initiated by supernatants from the transfected COS sFV105 or COS sFv105-KDEl cells is delayed about 5 days relative to that initated by supernatants from the tranfected COS sFv105 or COS sFV105-KDEL cells is delayed about 5 days relative to that initiated by virus produced by a control COS-1 cell line that contains the vector but not the sFV105 sequences. FIG. 11 shows virus yield by the infected SupT1 cells. The infectious pSVIIIB DNA is an infectious HIV-1 proviral DNA of the HXBc2 strain [Fisher, A. G., et al. *Nature* 315:262–265 (1985)]. The sFv105 or sFv105-KDEL or vector transformed cells were transfected with 5 µg of pSVIIIB plasmid DNA containing an infectious HIV-1 proviral DNA of the HXBc2 strain. After 4 days of transfection, the supernatants from the transfected cells were inoculated with SupTi cells for 16 hours and then washed, placed in fresh medium, monitored for concentration of viral capsid p24 protein by gag p24 activity in the culture medium. The medium amounts detected from the supernatants of transfected cells were 1.2 ng/ml (vector-COS), 1.0 ng/ml (COS sFv105), and 1.4 ng (COS sFv105-KDEL) respectively. The symbols in FIG. 11 represent the results obtained using supernatants harvested from the COS control cell line that contains the vector alone (O), a COS cell line that consitutively expresses the sFv105 protein (□), and a COS cell line that expresses the sFv105-KDEL protein (Δ).

Figure 12:
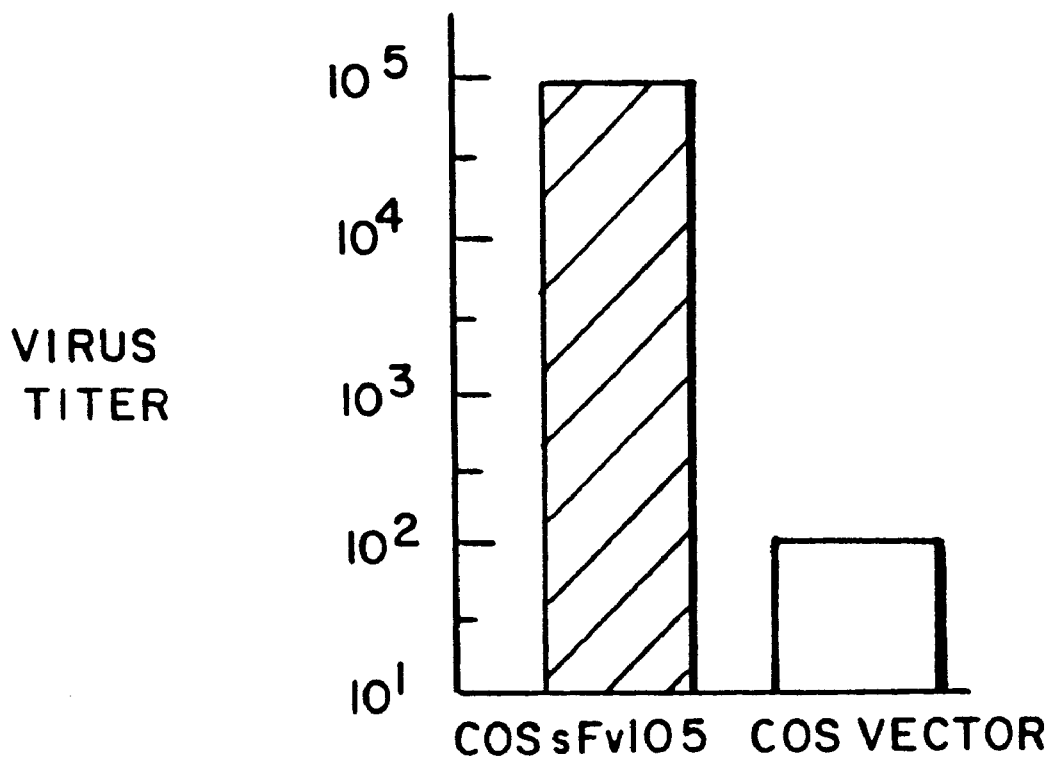
FIG. 12 shows virus titer by syncytium formation in SupT1 cells.

When serial dilution of the supernatants were used to infect SupT1 cells, there was a greater than 10$^3$ fold reduction in syncytium formation (FIG. 12). FIG. 12 shows virus titer by syncytium formation in SupT1 cells. The transformed COS vector and COS-sFv105 cells were transfected with 4 µg of pSVIIIB plasmid DNA containing an infectious HIV-1 proviral DNA of the HXBc2 strain [Ratner, supra]. After 48 hours of transfection, the supernatants from the transfected cells were harvested and used in serial dilutions to infect SupT1 cells for 16 hours and then washed. After 8 days, syncytia were counted. Data are number of wells positive for syncytia/number of wells counted. Five high power fields (HPF) were counted in each well. One or more syncytia in five HPF counts as (+) for the dilution. The delay in replication of virus produced by COS sFv105 cells and the decrease in infectious titer is attributed to low infectivity of the virus relative to that of virus produced by the control cell line. The results of these experiments demonstrate that cells can produce antibodies that function intracellularly. The antibody is stably expressed and retained in the endoplasmic reticulum and is not toxic to the cells. The antibody binds to the envelope protein within the cell and inhibits the maturation and function of this critical virus protein. The infectivity of the HIV-1 particles produced by cells that express the single chain antibody is substantially reduced.

4. Inducible Expression of Intracellular Antibody

Figure 13:
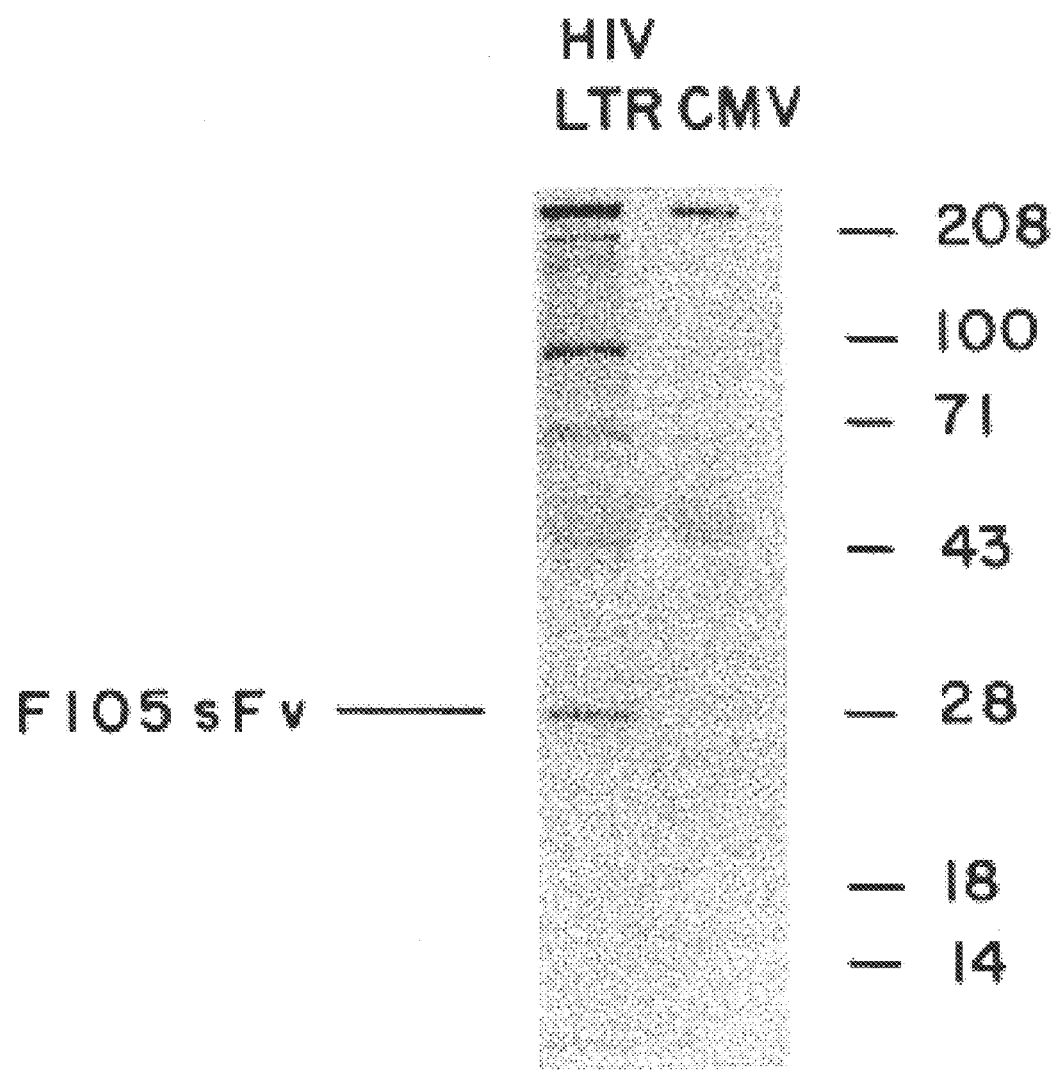
FIG. 13 are autoradiograms showing SupT cells stably transformed with a single chain antibody under the control of either an inducible promoter or a CMV promoter.
Figure 14:
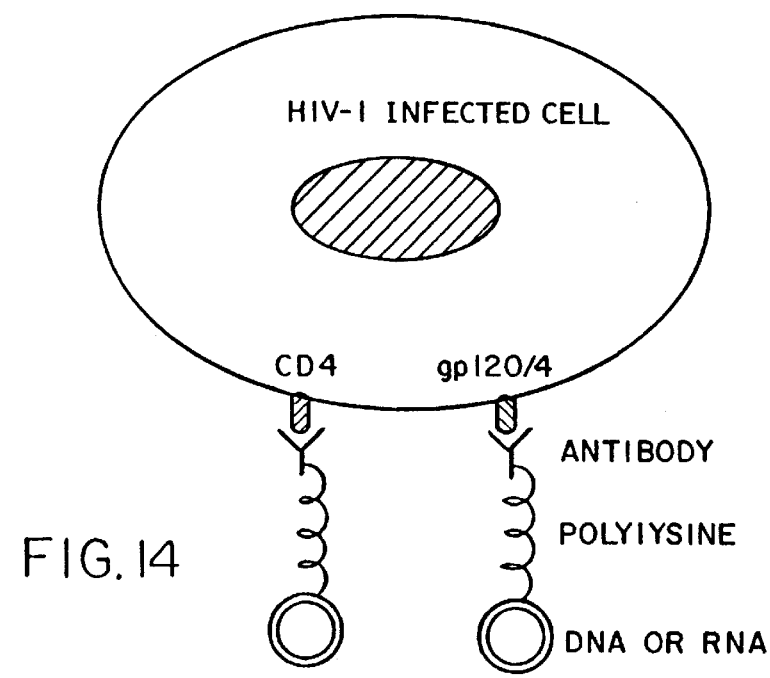
FIG. 14 shows the strategy of antibody-mediated gene transfer.
Figure 15:
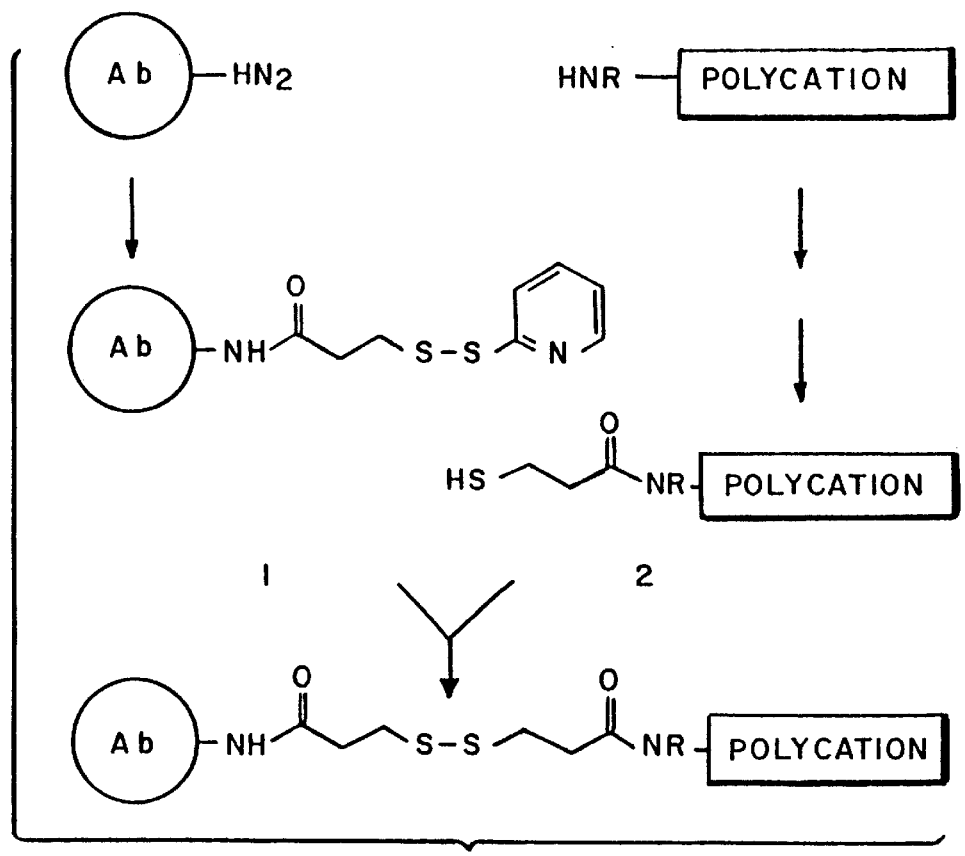
FIG. 15 shows the synthesis of antibody-polylysine conjugates.

We cloned the F105 sFv under the control of the HIV-1 5' LTR and have established stable cell lines in SupT cells. As can be seen in FIG. 13 lane 1, the F105 sFv is expressed following transfection of stable F105 sFv LTR SupT cells with the tat expressing plasmid pSVIIItat. FIG. 13 shows SupT cells stably transformed with pLTR F105 sFv (Lane 1) or pRC/CMV F105 sFv (Lane 2). SupT LTR F105 sFv cells were additionally transfected with pSVIIItat. Both cells were labelled with 35$^S$-Cys for 3 hours and cell lysates prepared. Radioimmunoprecipitation was with anti-human kappa chain antisera followed by 15% SDS-PAGE. No F105 sFv is seen in the absence of tat protein expression. The promoter and cell interdependence of this expression is shown in lane 2 of FIG. 13 where the CMV promoter is used. Many clones were screened and virtually non produced detectable antibody. Jurkat cells gave similar results.

Figure 16:
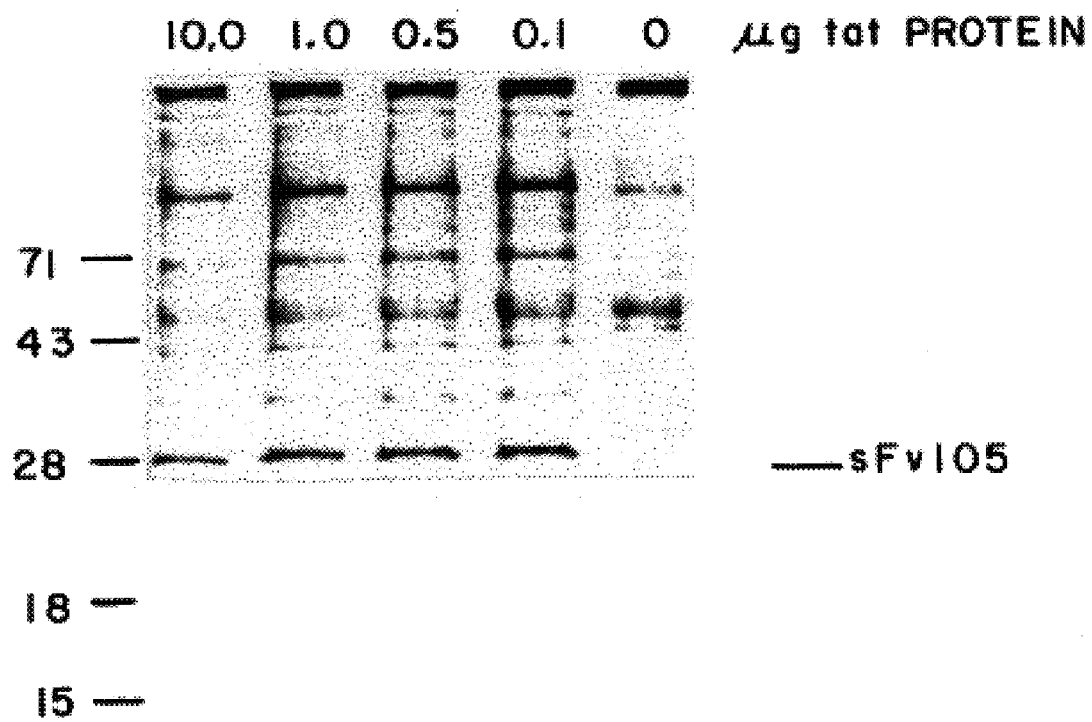
FIG. 16 are autoradiograms showing expression of the sFv F105 in SupT HIV-infected cells under varying concentration of tat protein.

The above-described stably-transformed SupT cells stably transformed with the F105 sFv under the control of the HIV-1 LTR were induced with varying concentrations of tat protein. FIG. 16 shows that the F105 sFv was inducibly-expressed with as little as 0.1 μg of tat protein. Lane 1 shows administration of 10 μg of tat protein; Lane 2 is 1 μg of tat protein; Lane 3 is 0.5 μg of protein; Lane 4 is 0.1 μg of protein and Lane 5 is 0 μg of protein. There is a marker to indicate the location of the sFv 105. The transformed SupT cells maintain normal morphology and replication rates and can be transduced to express high levels of the F105 sFv.

Figure 17A:
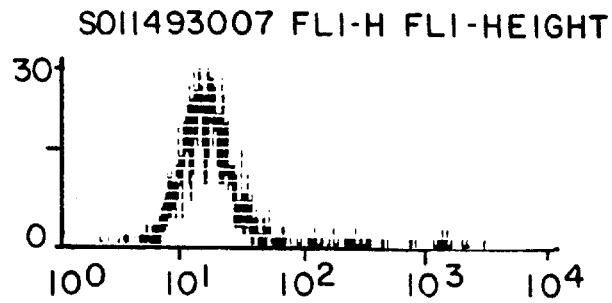
FIGS. 17 A–D show FACS analysis of gp120 expression in CD4 SupT cells infected with HIV-1 and stably transduced with the F105 sFv.
Figure 17B:
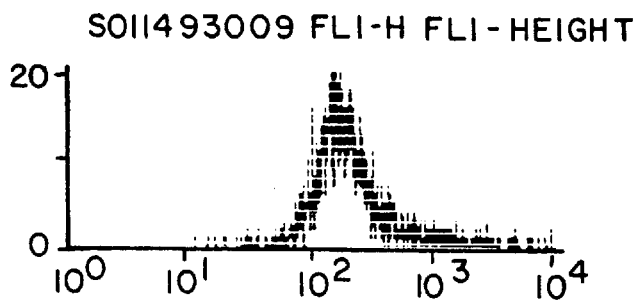
Figure 17C:
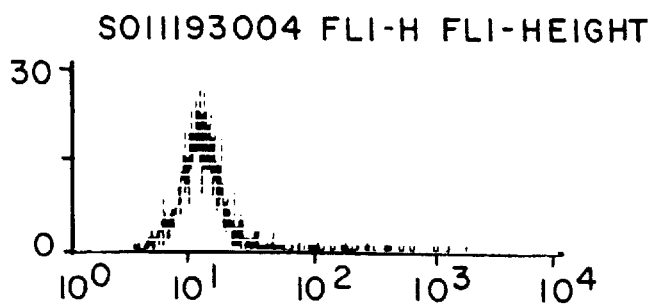

SupT cells were infected with HIV-1 as described above. They were then stably transduced with pLTR F105 sFv as described above. FIG. 17 is a FACS analysis of SupT cells. FIG. 17A is a negative control showing a SupT 1 cell that is not infected. FIG. 17B is a positive control of the SupT HIV infected cells that was not transduced. FIG. 17C is a FACS analysis of the SupT HIV-LTR-sFv 105 transduced HIV-infected SupT cells and FIG. 17D is the HIV-infected SupT cell mock infected with a vector containing the HIV-LTR but not the sFv 105 antibody gene.

Figure 17D:
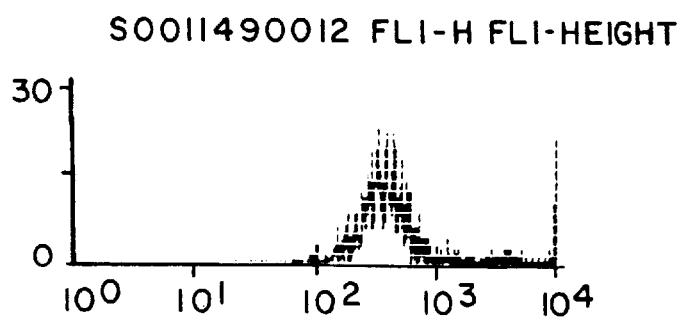

FIGS. 17B–D show surface staining of gp120 using FITC-anti-gp120 (ABT Inc.) eight days after infection with 20 M.O.I. HXB2 strain of HIV-1. As can be seen from the analysis, FIG. 17D shows the same general pattern of staining the SupT cells as the positive control (FIG. 17B). In contrast, the HIV-infected cell transduced with the antibody according to present invention (FIG. 17C) shows a background staining similar to the negative control (FIG. 17A), thereby demonstrating that surface gp120 expression is markedly diminished in SupT sFv 105 cells.

Figure 18A:
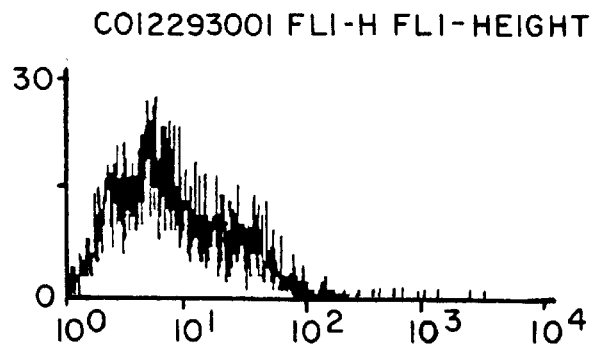
FIGS. 18 A–D show surface CD4 expression in HIV-1 infected SupT cells transduced with sFv F105.
Figure 18B:
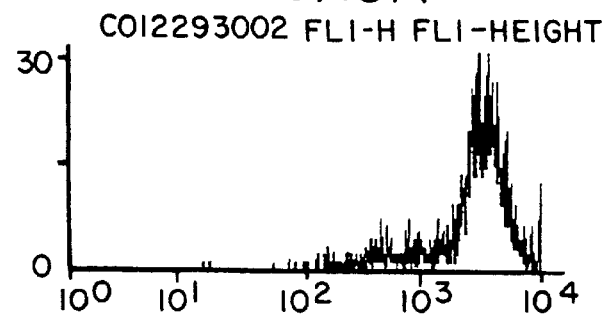
Figure 18C:
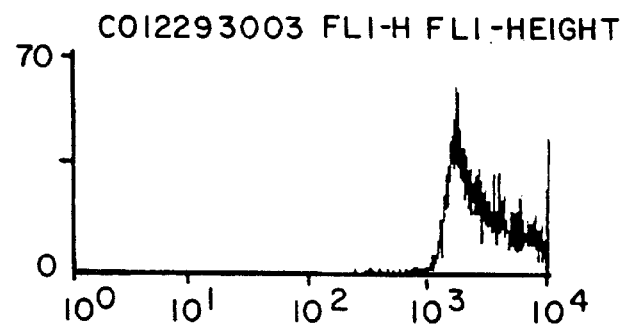
Figure 18D:
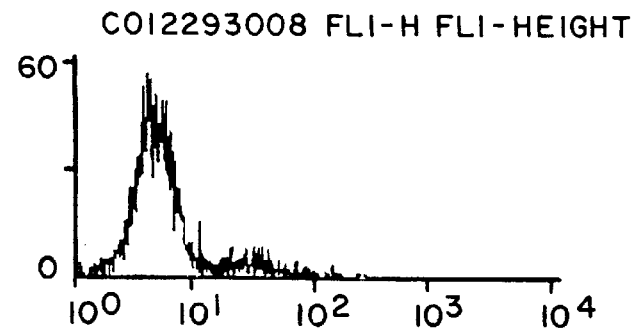

FIGS. 18A–D look at the surface CD4 expression in such cells. FIG. 18A shows background staining in a negative control, whereas FIG. 18B shows the surface staining of CD4 using FITC-anti-CD4 (ABT, Inc.) at eight days post-infection with 20 M.O.I. HXB2 strain of HIV-1 (the positive control). FIG. 18D shows the marked down-regulation of CD4 expression on SupT HIV-infected cells that are mocked-infected with the HIV-LTR vector eight days after such infection. In contrast, FIG. 18C shows that surface CD4 expression in the SupT HIV-infected cells transduced with sFv 105, under the control of the HIV-LTR, was nearly normal eight days after infection. Thus, these experiments demonstrate that surface CD4 expression was not significantly down-regulated in cells wherein HIV protein was targeted according to the present invention. The experiment further implies that the intracellular complexes of CD4-gp160, which are known to form in the ER, can be disrupted by the present method.

Figure 19:
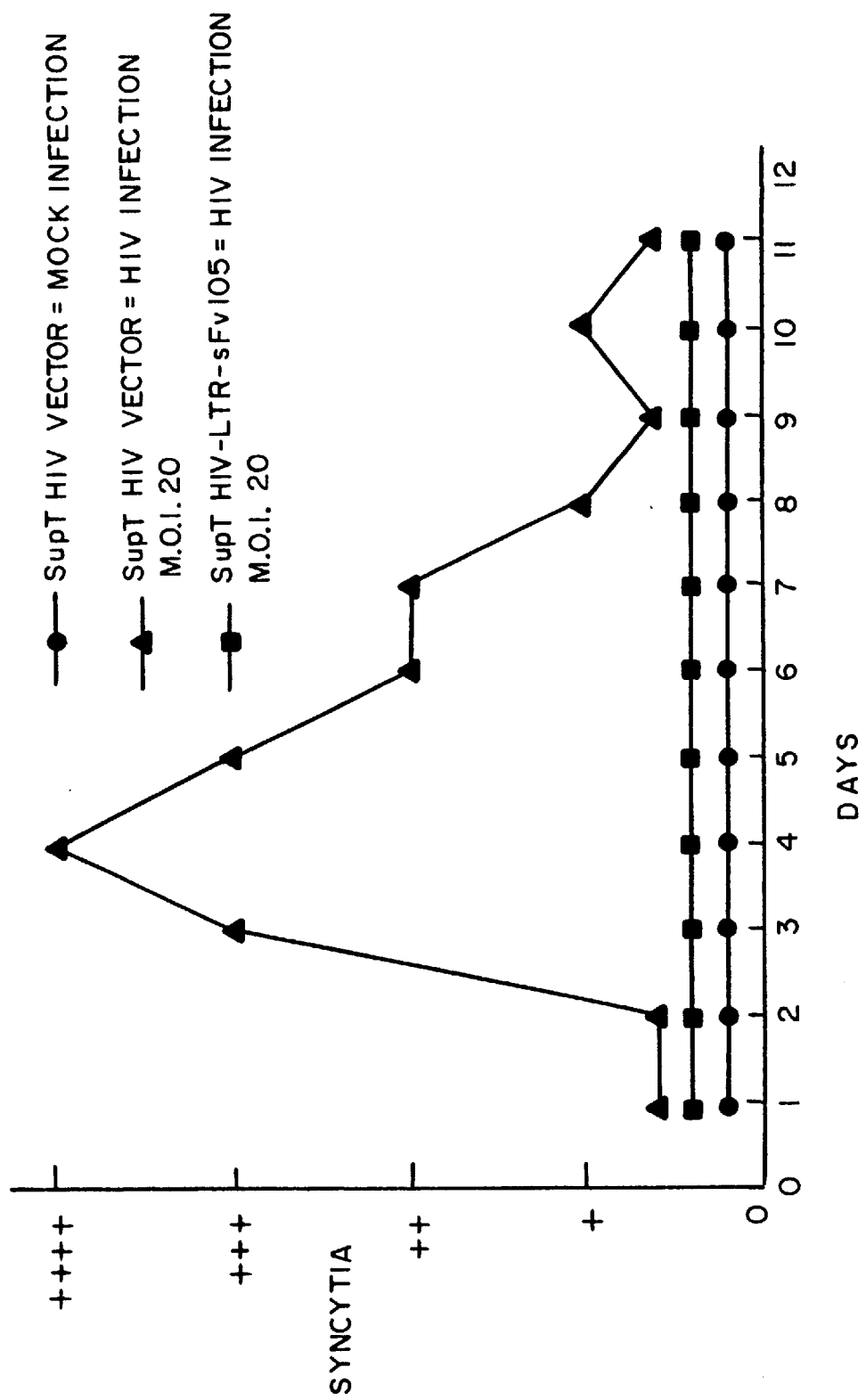
FIG. 19 shows the result of syncytia formation studies after infecting SupT svector cells or SupT sFv 105 cells with HIV-1.

FIG. 19 shows the cytopathic effects of HIV-1 virus inhibition in CD4 SupT HIV-infected cells expressing the F105 sFv. The (Θ) line shows a mock transfected SupT cell. The (Δ) is a positive control showing a SupT cell that has been infected with HIV under the above-described conditions. The (□) shows the SupT cell that has been infected under the above-described conditions and transduced with the sFv 105 antibody under the control of the HIV-LTR as discussed above. This figure shows results of syncytia formation after infecting the SupT vector cells or SupT sFv 105 cells with 20 M.O.I. of HXBC2 strain of HIV-1 as described above. After 11 days post infection there is virtually no syncytia formed in the SupT sFv 105 cells. In contrast, in the SupT cells, a peak of syncytia is seen after 4–5 days. These experiments are consistant with the lack of surface expression of gp120 discussed above suggesting that the present intercellular antibodies lead to resistance of the cytopathic effects of gp120.

The references cited throughout the specification are incorporated herein by reference.

This invention has been described in detail including the preferred embodiments thereof. However, it will be appreciated that those skilled in the art, upon consideration of this disclosure, may make modifications and improvements thereon without departing from the spirit and scope of the invention as set forth in the claims.

We claim:

1. An antibody, wherein the antibody contains a secretory signal and further contains an intracellular retention sequence.

2. The antibody of claim 1, wherein the intracellular retention sequence is an endoplasmic reticulum localization sequence.

3. The antibody of claim 1, wherein the antibody is a Fab' or single chain antibody.

4. The antibody of claim 1, wherein the antibody is a single chain antibody.

5. A single chain antibody, wherein the antibody does not contain a secretory signal, and wherein the single chain antibody contains an intracellular localization sequence.

* * * * *

SEQUENCE LISTING (1) GENERAL INFORMATION:

(iii) NUMBER OF SEQUENCES: 78

(2) INFORMATION FOR SEQ ID NO:1:

(i) SEQUENCE CHARACTERISTICS:
      (A) LENGTH: 15 amino acids
      (B) TYPE: amino acid
      (D) TOPOLOGY: linear (xi) SEQUENCE DESCRIPTION: SEQ ID NO:1:

```
Gly Gly Gly Gly Ser Gly Gly Gly Gly Ser Gly Gly Gly Gly Ser
1               5                   10                  15
```

(2) INFORMATION FOR SEQ ID NO:2:

(i) SEQUENCE CHARACTERISTICS:
      (A) LENGTH: 15 amino acids
      (B) TYPE: amino acid
      (D) TOPOLOGY: linear (xi) SEQUENCE DESCRIPTION: SEQ ID NO:2:

```
Glu Ser Gly Arg Ser Gly Gly Gly Ser Gly Gly Gly Ser
1               5                  10                 15
```

(2) INFORMATION FOR SEQ ID NO:3:

(i) SEQUENCE CHARACTERISTICS:
  (A) LENGTH: 14 amino acids
  (B) TYPE: amino acid
  (D) TOPOLOGY: linear (xi) SEQUENCE DESCRIPTION: SEQ ID NO:3:

```
Glu Gly Lys Ser Ser Gly Ser Gly Ser Glu Ser Lys Ser Thr
1               5                  10
```

(2) INFORMATION FOR SEQ ID NO:4:

(i) SEQUENCE CHARACTERISTICS:
  (A) LENGTH: 15 amino acids
  (B) TYPE: amino acid
  (D) TOPOLOGY: linear (xi) SEQUENCE DESCRIPTION: SEQ ID NO:4:

```
Glu Gly Lys Ser Ser Gly Ser Gly Ser Glu Ser Lys Ser Thr Gln
1               5                  10                 15
```

(2) INFORMATION FOR SEQ ID NO:5:

(i) SEQUENCE CHARACTERISTICS:
  (A) LENGTH: 14 amino acids
  (B) TYPE: amino acid
  (D) TOPOLOGY: linear (xi) SEQUENCE DESCRIPTION: SEQ ID NO:5:

```
Glu Gly Lys Ser Ser Gly Ser Gly Ser Glu Ser Lys Val Asp
1               5                  10
```

(2) INFORMATION FOR SEQ ID NO:6:

(i) SEQUENCE CHARACTERISTICS:
  (A) LENGTH: 14 amino acids
  (B) TYPE: amino acid
  (D) TOPOLOGY: linear (xi) SEQUENCE DESCRIPTION: SEQ ID NO:6:

```
Gly Ser Thr Ser Gly Ser Gly Lys Ser Ser Glu Gly Lys Gly
1               5                  10
```

(2) INFORMATION FOR SEQ ID NO:7:

(i) SEQUENCE CHARACTERISTICS:
  (A) LENGTH: 18 amino acids
  (B) TYPE: amino acid
  (D) TOPOLOGY: linear (xi) SEQUENCE DESCRIPTION: SEQ ID NO:7:

```
Lys Glu Ser Gly Ser Val Ser Ser Glu Gln Leu Ala Gln Phe Arg Ser
1               5                  10                 15
Leu Asp
```

(2) INFORMATION FOR SEQ ID NO:8:

(i) SEQUENCE CHARACTERISTICS:
  (A) LENGTH: 16 amino acids
  (B) TYPE: amino acid
  (D) TOPOLOGY: linear (xi) SEQUENCE DESCRIPTION: SEQ ID NO:8:

```
Glu Ser Gly Ser Val Ser Ser Glu Glu Leu Ala Phe Arg Ser Leu Asp
1               5                   10                  15
```

(2) INFORMATION FOR SEQ ID NO:9:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:9:

TTTGCGGCCG CTCAGGTGCA RCTGCTCGAG TCYGG                                        35

(2) INFORMATION FOR SEQ ID NO:10:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (xi) SEQUENCE DESCRIPTION: SEQ ID NO:10:

AGATCCGCCG CCACCGCTCC CACCACCTCC GGAGCCACCG CCACCTGAGG TGACCGTGAC    60

CRKGGT                                                                                      66

(2) INFORMATION FOR SEQ ID NO:11:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:11:

GGTGGCGGTG GCTCCGGAGG TGGGTGGGAG CGGTGGCGGC GGATCTGAGC TCSWGMTGAC    60

CCAGTCTCCA                                                                                              70

(2) INFORMATION FOR SEQ ID NO:12:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:12:

GGGTCTAGAC TCGAGGATCC TTATTAACGC GTTGGTGCAG CCACAGT                    47

(2) INFORMATION FOR SEQ ID NO:13:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:13:

```
Ser Glu Lys Asp Glu Leu
1               5
```

(2) INFORMATION FOR SEQ ID NO:14:

(i) SEQUENCE CHARACTERISTICS:
        (A) LENGTH: 59 base pairs (B) TYPE: nucleic acid
            (C) STRANDEDNESS: single
            (D) TOPOLOGY: linear (xi) SEQUENCE DESCRIPTION: SEQ ID NO:14:

GGGTCTAGAC TCGAGGATCC TTATTACAGC TCGTCCTTTT CGCTTGGTGC AGCCACAGT         59

(2) INFORMATION FOR SEQ ID NO:15:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:15:

TTTACCATGG AACATCTGTG GTTC                                              24

(2) INFORMATION FOR SEQ ID NO:16:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:16:

TTAGCGCGCT GAGGTGACCG TGACCRKGGT                                        30

(2) INFORMATION FOR SEQ ID NO:17:

(i) SEQUENCE CHARACTERISTICS:
            (A) LENGTH: 4 amino acids
            (B) TYPE: amino acid
            (D) TOPOLOGY: linear (xi) SEQUENCE DESCRIPTION: SEQ ID NO:17:

Lys Asp Glu Leu
1

(2) INFORMATION FOR SEQ ID NO:18:

(i) SEQUENCE CHARACTERISTICS:
            (A) LENGTH: 4 amino acids
            (B) TYPE: amino acid
            (D) TOPOLOGY: linear (xi) SEQUENCE DESCRIPTION: SEQ ID NO:18:

Asp Asp Glu Leu
1

(2) INFORMATION FOR SEQ ID NO:19:

(i) SEQUENCE CHARACTERISTICS:
            (A) LENGTH: 4 amino acids
            (B) TYPE: amino acid
            (D) TOPOLOGY: linear (xi) SEQUENCE DESCRIPTION: SEQ ID NO:19:

Asp Glu Glu Leu
1

(2) INFORMATION FOR SEQ ID NO:20:

(i) SEQUENCE CHARACTERISTICS:
            (A) LENGTH: 4 amino acids
            (B) TYPE: amino acid (D) TOPOLOGY: linear (xi) SEQUENCE DESCRIPTION: SEQ ID NO:20:

Gln Glu Asp Leu
1

(2) INFORMATION FOR SEQ ID NO:21:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:21:

Arg Asp Glu Leu
1

(2) INFORMATION FOR SEQ ID NO:22:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO:22:

Pro Lys Lys Lys Arg Lys Val
1               5

(2) INFORMATION FOR SEQ ID NO:23:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO:23:

Pro Gln Lys Lys Ile Lys Ser
1               5

(2) INFORMATION FOR SEQ ID NO:24:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:24:

Gln Pro Lys Lys Lys Pro
1               5

(2) INFORMATION FOR SEQ ID NO:25:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO:25:

Arg Lys Lys Arg Arg Gln Arg Arg Arg Ala His Gln
1               5                   10

(2) INFORMATION FOR SEQ ID NO:26:

(i) SEQUENCE CHARACTERISTICS:
        (A) LENGTH: 16 amino acids
        (B) TYPE: amino acid
        (D) TOPOLOGY: linear (xi) SEQUENCE DESCRIPTION: SEQ ID NO:26:

Arg Gln Ala Arg Arg Asn Arg Arg Arg Trp Arg Glu Arg Gln Arg
1               5                   10                  15

(2) INFORMATION FOR SEQ ID NO:27:

(i) SEQUENCE CHARACTERISTICS:
        (A) LENGTH: 19 amino acids
        (B) TYPE: amino acid
        (D) TOPOLOGY: linear (xi) SEQUENCE DESCRIPTION: SEQ ID NO:27:

Met Pro Leu Thr Arg Arg Arg Pro Ala Ala Ser Gln Ala Leu Ala Pro
1               5                   10                  15

Pro Thr Pro (2) INFORMATION FOR SEQ ID NO:28:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:28:

Met Asp Asp Gln Arg Asp Leu Ile Ser Asn Asn Glu Gln Leu Pro
1               5                   10                  15

(2) INFORMATION FOR SEQ ID NO:29:

(i) SEQUENCE CHARACTERISTICS:
        (A) LENGTH: 32 amino acids
        (B) TYPE: amino acid
        (D) TOPOLOGY: linear (xi) SEQUENCE DESCRIPTION: SEQ ID NO:29:

Met Leu Phe Asn Leu Arg Xaa Xaa Leu Asn Asn Ala Ala Phe Arg His
1               5                   10                  15

Gly His Asn Phe Met Val Arg Asn Phe Arg Cys Gly Gln Pro Leu Xaa
                20                  25                  30

(2) INFORMATION FOR SEQ ID NO:30:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:30:

Gly Cys Val Cys Ser Ser Asn Pro
1               5

(2) INFORMATION FOR SEQ ID NO:31:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:31:

Gly Gln Thr Val Thr Thr Pro Leu
1               5

(2) INFORMATION FOR SEQ ID NO:32:

(i) SEQUENCE CHARACTERISTICS:
            (A) LENGTH: 8 amino acids
            (B) TYPE: amino acid
            (D) TOPOLOGY: linear (xi) SEQUENCE DESCRIPTION: SEQ ID NO:32:

Gly Gln Glu Leu Ser Gln His Glu
    1               5

(2) INFORMATION FOR SEQ ID NO:33:

(i) SEQUENCE CHARACTERISTICS:
            (A) LENGTH: 8 amino acids
            (B) TYPE: amino acid
            (D) TOPOLOGY: linear (xi) SEQUENCE DESCRIPTION: SEQ ID NO:33:

Gly Asn Ser Pro Ser Tyr Asn Pro
1               5

(2) INFORMATION FOR SEQ ID NO:34:

(i) SEQUENCE CHARACTERISTICS:
            (A) LENGTH: 8 amino acids
            (B) TYPE: amino acid
            (D) TOPOLOGY: linear (xi) SEQUENCE DESCRIPTION: SEQ ID NO:34:

Gly Val Ser Gly Ser Lys Gly Gln
1               5

(2) INFORMATION FOR SEQ ID NO:35:

(i) SEQUENCE CHARACTERISTICS:
            (A) LENGTH: 8 amino acids
            (B) TYPE: amino acid
            (D) TOPOLOGY: linear (xi) SEQUENCE DESCRIPTION: SEQ ID NO:35:

Gly Gln Thr Ile Thr Thr Pro Leu
1               5

(2) INFORMATION FOR SEQ ID NO:36:

(i) SEQUENCE CHARACTERISTICS:
            (A) LENGTH: 8 amino acids
            (B) TYPE: amino acid
            (D) TOPOLOGY: linear (xi) SEQUENCE DESCRIPTION: SEQ ID NO:36:

Gly Gln Thr Ile Thr Thr Pro Leu
1               5

(2) INFORMATION FOR SEQ ID NO:37:

(i) SEQUENCE CHARACTERISTICS:
            (A) LENGTH: 8 amino acids
            (B) TYPE: amino acid
            (D) TOPOLOGY: linear (xi) SEQUENCE DESCRIPTION: SEQ ID NO:37:

Gly Gln Ile Phe Ser Arg Ser Ala
1               5

(2) INFORMATION FOR SEQ ID NO:38:

(i) SEQUENCE CHARACTERISTICS:

(A) LENGTH: 8 amino acids
            (B) TYPE: amino acid
            (D) TOPOLOGY: linear (xi) SEQUENCE DESCRIPTION: SEQ ID NO:38:

Gly Gln Ile His Gly Leu Ser Pro
1               5

(2) INFORMATION FOR SEQ ID NO:39:

(i) SEQUENCE CHARACTERISTICS:
            (A) LENGTH: 8 amino acids
            (B) TYPE: amino acid
            (D) TOPOLOGY: linear (xi) SEQUENCE DESCRIPTION: SEQ ID NO:39:

Gly Ala Arg Ala Ser Val Leu Ser
1               5

(2) INFORMATION FOR SEQ ID NO:40:

(i) SEQUENCE CHARACTERISTICS:
            (A) LENGTH: 8 amino acids
            (B) TYPE: amino acid
            (D) TOPOLOGY: linear (xi) SEQUENCE DESCRIPTION: SEQ ID NO:40:

Gly Cys Thr Leu Ser Ala Glu Glu
1               5

(2) INFORMATION FOR SEQ ID NO:41:

(i) SEQUENCE CHARACTERISTICS:
            (A) LENGTH: 8 amino acids
            (B) TYPE: amino acid
            (D) TOPOLOGY: linear (xi) SEQUENCE DESCRIPTION: SEQ ID NO:41:

Gly Gln Asn Leu Ser Thr Ser Asn
1               5

(2) INFORMATION FOR SEQ ID NO:42:

(i) SEQUENCE CHARACTERISTICS:
            (A) LENGTH: 8 amino acids
            (B) TYPE: amino acid
            (D) TOPOLOGY: linear (xi) SEQUENCE DESCRIPTION: SEQ ID NO:42:

Gly Ala Ala Leu Thr Ile Leu Val
1               5

(2) INFORMATION FOR SEQ ID NO:43:

(i) SEQUENCE CHARACTERISTICS:
            (A) LENGTH: 8 amino acids
            (B) TYPE: amino acid
            (D) TOPOLOGY: linear (xi) SEQUENCE DESCRIPTION: SEQ ID NO:43:

Gly Ala Ala Leu Thr Leu Leu Gly
1               5

(2) INFORMATION FOR SEQ ID NO:44:

(i) SEQUENCE CHARACTERISTICS:
            (A) LENGTH: 8 amino acids

```
            (B) TYPE: amino acid
            (D) TOPOLOGY: linear (xi) SEQUENCE DESCRIPTION: SEQ ID NO:44:

Gly Ala Gln Val Ser Ser Gln Lys
1               5

(2) INFORMATION FOR SEQ ID NO:45:

(i) SEQUENCE CHARACTERISTICS:
            (A) LENGTH: 8 amino acids
            (B) TYPE: amino acid
            (D) TOPOLOGY: linear (xi) SEQUENCE DESCRIPTION: SEQ ID NO:45:

Gly Ala Gln Leu Ser Arg Asn Thr
1               5

(2) INFORMATION FOR SEQ ID NO:46:

(i) SEQUENCE CHARACTERISTICS:
            (A) LENGTH: 8 amino acids
            (B) TYPE: amino acid
            (D) TOPOLOGY: linear (xi) SEQUENCE DESCRIPTION: SEQ ID NO:46:

Gly Asn Ala Ala Ala Ala Lys Lys
1               5

(2) INFORMATION FOR SEQ ID NO:47:

(i) SEQUENCE CHARACTERISTICS:
            (A) LENGTH: 8 amino acids
            (B) TYPE: amino acid
            (D) TOPOLOGY: linear (xi) SEQUENCE DESCRIPTION: SEQ ID NO:47:

Gly Asn Glu Ala Ser Tyr Pro Leu
1               5

(2) INFORMATION FOR SEQ ID NO:48:

(i) SEQUENCE CHARACTERISTICS:
            (A) LENGTH: 8 amino acids
            (B) TYPE: amino acid
            (D) TOPOLOGY: linear (xi) SEQUENCE DESCRIPTION: SEQ ID NO:48:

Gly Ser Ser Lys Ser Lys Pro Lys
1               5

(2) INFORMATION FOR SEQ ID NO:49:

(i) SEQUENCE CHARACTERISTICS:
            (A) LENGTH: 55 base pairs
            (B) TYPE: nucleic acid
            (C) STRANDEDNESS: single
            (D) TOPOLOGY: linear (xi) SEQUENCE DESCRIPTION: SEQ ID NO:49:

CCCTCTAGAC ATATGTGAAT TCCACCATGG CCCAGGTSMA RCTGCAGCAG TCAGG        55

(2) INFORMATION FOR SEQ ID NO:50:

(i) SEQUENCE CHARACTERISTICS:
            (A) LENGTH: 43 base pairs
            (B) TYPE: nucleic acid
```

(C) STRANDEDNESS: single
            (D) TOPOLOGY: linear (xi) SEQUENCE DESCRIPTION: SEQ ID NO:50:

GGGGCGCGCT GMGGAGACGG TGACCRWGGT CCCTKSGCCC CAG            43

(2) INFORMATION FOR SEQ ID NO:51:

(i) SEQUENCE CHARACTERISTICS:
            (A) LENGTH: 89 base pairs
            (B) TYPE: nucleic acid
            (C) STRANDEDNESS: single
            (D) TOPOLOGY: linear (xi) SEQUENCE DESCRIPTION: SEQ ID NO:51:

TTTGGTCACC GTCTCCCTCA GGTGGCGGTG GCTCGGGCGG TGGTGGGTCG GGTGGCGGCG    60

GATCTSAHAT TCAGCTGACM CARWCTCCA                                      89

(2) INFORMATION FOR SEQ ID NO:52:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (xi) SEQUENCE DESCRIPTION: SEQ ID NO:52:

GGGTCTAGAC TCGAGGATCC TTATTATACA GTTGGTGCAG CATC           44

(2) INFORMATION FOR SEQ ID NO:53:

(i) SEQUENCE CHARACTERISTICS:
            (A) LENGTH: 71 base pairs
            (B) TYPE: nucleic acid
            (C) STRANDEDNESS: single
            (D) TOPOLOGY: linear (xi) SEQUENCE DESCRIPTION: SEQ ID NO:53:

GGGTCTAGAC TCGAGGATCC TTATTAAACC TTACGTTTCT TCTTCGGCGG AGTTACAGTT    60

GGTGCAGCAT C                                                         71

(2) INFORMATION FOR SEQ ID NO:54:

(i) SEQUENCE CHARACTERISTICS:
            (A) LENGTH: 10 amino acids
            (B) TYPE: amino acid
            (D) TOPOLOGY: linear (xi) SEQUENCE DESCRIPTION: SEQ ID NO:54:

Thr Pro Pro Lys Lys Lys Lys Arg Lys Val
1               5                   10

(2) INFORMATION FOR SEQ ID NO:55:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:55:

ATTAGCGGCC GCTACAGTTG GTGCAGCATC                           30

(2) INFORMATION FOR SEQ ID NO:56:

(i) SEQUENCE CHARACTERISTICS:
         (A) LENGTH: 4 amino acids
         (B) TYPE: amino acid
         (D) TOPOLOGY: linear (xi) SEQUENCE DESCRIPTION: SEQ ID NO:56:

Arg Lys Lys Arg
1

(2) INFORMATION FOR SEQ ID NO:57:

(i) SEQUENCE CHARACTERISTICS:
         (A) LENGTH: 41 base pairs
         (B) TYPE: nucleic acid
         (C) STRANDEDNESS: single
         (D) TOPOLOGY: linear (xi) SEQUENCE DESCRIPTION: SEQ ID NO:57:

TTTAAGCTTA CCATGGCCCA GGTGCAGCTG CAGGAGTCGG G                    41

(2) INFORMATION FOR SEQ ID NO:58:

(i) SEQUENCE CHARACTERISTICS:
         (A) LENGTH: 10 amino acids
         (B) TYPE: amino acid
         (D) TOPOLOGY: linear (xi) SEQUENCE DESCRIPTION: SEQ ID NO:58:

Met Ala Gln Val Gln Leu Gln Glu Ser Gly
1               5                   10

(2) INFORMATION FOR SEQ ID NO:59:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (xi) SEQUENCE DESCRIPTION: SEQ ID NO:59:

TTTAAGCTTA CCATGGACTG GACCTGGAGG                                 30

(2) INFORMATION FOR SEQ ID NO:60:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (xi) SEQUENCE DESCRIPTION: SEQ ID NO:60:

TGAGGTGACC GTGACCAGGG T                                          21

(2) INFORMATION FOR SEQ ID NO:61:

(i) SEQUENCE CHARACTERISTICS:
         (A) LENGTH: 33 base pairs
         (B) TYPE: nucleic acid
         (C) STRANDEDNESS: single
         (D) TOPOLOGY: linear (xi) SEQUENCE DESCRIPTION: SEQ ID NO:61:

TTTAAGCTTA CCATGGAGTT TGGGCTGAGC TGG                             33

(2) INFORMATION FOR SEQ ID NO:62:

(i) SEQUENCE CHARACTERISTICS:

(A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:62:

CTGCGTCAAC ACAGACTGAG ATCCGCC                                              27

(2) INFORMATION FOR SEQ ID NO:63:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:63:

CGAGGGGGYR GCCTTGGGCT G                                                    21

(2) INFORMATION FOR SEQ ID NO:64:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:64:

TTTTCTAGAT CYTMTGAACT GACTCAG                                              27

(2) INFORMATION FOR SEQ ID NO:65:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:65:

GGAACCCTGG TCACGGTCAC CTCA                                                 24

(2) INFORMATION FOR SEQ ID NO:66:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:66:

TGGAGACTGC GTCATCTCGA GTTC                                                 24

(2) INFORMATION FOR SEQ ID NO:67:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:67:

GAACTCGAGW TGACGCAGTC TCCA                                                 24

(2) INFORMATION FOR SEQ ID NO:68:

(i) SEQUENCE CHARACTERISTICS:
        (A) LENGTH: 47 base pairs (B) TYPE: nucleic acid
        (C) STRANDEDNESS: single
        (D) TOPOLOGY: linear (xi) SEQUENCE DESCRIPTION: SEQ ID NO:68:

GGGTCTAGAC TCGAGGATCC TTATTAACGC GTTGGTGCAG CCACAGT                47

(2) INFORMATION FOR SEQ ID NO:69:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:69:

ACGGCCGTGT ATTACTGTGC GCGA                                         24

(2) INFORMATION FOR SEQ ID NO:70:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:70:

TGGGGCCAGG GAACCCYGGT CACSGTNWCC                                   30

(2) INFORMATION FOR SEQ ID NO:71:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:71:

CGCACAGTAA TACAC                                                   15

(2) INFORMATION FOR SEQ ID NO:72:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:72:

GTGACCGTGA CCGGGGT                                                 17

(2) INFORMATION FOR SEQ ID NO:73:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:73:

GGCCGTGTAT TACTGTGCGC GANNSTGGGG CCAGGGAACC CCGGTC                 46

(2) INFORMATION FOR SEQ ID NO:74:

(i) SEQUENCE CHARACTERISTICS:
        (A) LENGTH: 15 amino acids
        (B) TYPE: amino acid (C) STRANDEDNESS: single
(D) TOPOLOGY: linear (xi) SEQUENCE DESCRIPTION: SEQ ID NO:74:

```
Leu Thr Leu Ile Ser Ser Arg Leu Arg Leu Ile Ala Val Arg Met
1               5                   10                  15
```

(2) INFORMATION FOR SEQ ID NO:75:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:75:

TTTAAGCTTA CCATGAACTT CGGGCTC        27

(2) INFORMATION FOR SEQ ID NO:76:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:76:

TGMGGAGACG GTGACCRWGG TCCCT        25

(2) INFORMATION FOR SEQ ID NO:77:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:77:

GAGCTCGTGC TCACMCARWC TCCA        24

(2) INFORMATION FOR SEQ ID NO:78:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:78:

GGGTCTAGAC TCGAGGATCC TTATTATACA GTTGGTGCAG CATC        44